(12) United States Patent
Gershman et al.

(10) Patent No.: US 6,401,085 B1
(45) Date of Patent: Jun. 4, 2002

(54) MOBILE COMMUNICATION AND COMPUTING SYSTEM AND METHOD

(75) Inventors: Anatole Vitaly Gershman, Chicago; Kishore Sundaram Swaminathan, Downers Grove; James L. Meyers, Chicago; Andrew Ernest Fano, Evanston, all of IL (US)

(73) Assignee: Accenture LLP, Palo Alto, CA (US)

( * ) Notice: Subject to any disclaimer, the term of this patent is extended or adjusted under 35 U.S.C. 154(b) by 0 days.

(21) Appl. No.: 09/263,969

(22) Filed: Mar. 5, 1999

(51) Int. Cl.[7] ............................................. G06F 17/30
(52) U.S. Cl. ........................ 707/4; 707/3; 707/10; 705/2; 709/223; 709/226
(58) Field of Search ........................ 705/2, 14, 26; 701/201; 707/5, 3, 10, 4, 102, 104.1; 709/223, 226

(56) References Cited

U.S. PATENT DOCUMENTS

| | | | |
|---|---|---|---|
| 5,279,882 A | | 1/1994 | Daude et al. ............... 428/192 |
| 5,519,608 A | | 5/1996 | Kupiec .......................... 704/9 |
| 5,606,602 A | | 2/1997 | Johnson et al. ............. 379/115 |
| 5,640,193 A | | 6/1997 | Wellner ......................... 348/7 |
| 5,673,322 A | | 9/1997 | Pepe et al. .................... 705/52 |
| 5,732,074 A | | 3/1998 | Spaur et al. ................. 370/313 |
| 5,854,624 A | | 12/1998 | Grant .......................... 345/169 |
| 5,897,622 A | * | 4/1999 | Blinn et al. ................... 705/26 |
| 5,933,811 A | * | 8/1999 | Angles et al. ................. 705/14 |
| 5,948,040 A | * | 9/1999 | DeLorme et al. ........... 701/201 |
| 5,997,476 A | * | 12/1999 | Brown ......................... 600/300 |
| 6,101,478 A | * | 8/2000 | Brown ........................... 705/2 |
| 6,134,548 A | * | 10/2000 | Gottsman et al. .............. 707/5 |

FOREIGN PATENT DOCUMENTS

| | | |
|---|---|---|
| EP | 0883313 A2 | 12/1998 |
| EP | 0890907 A1 | 1/1999 |
| WO | WO 97/17815 | 5/1997 |
| WO | WO 97/40451 | 10/1997 |
| WO | WO 97/45814 | 12/1997 |
| WO | WO 98/03923 | 1/1998 |
| WO | WO 98/06055 | 2/1998 |
| WO | WO 98/10541 | 3/1998 |
| WO | WO 98/11744 | 3/1998 |
| WO | WO 98/12833 | 3/1998 |
| WO | WO 98/24036 | 6/1998 |
| WO | WO 98/24050 | 6/1998 |
| WO | WO 98/39909 | 9/1998 |
| WO | WO 98/40823 | 9/1998 |
| WO | WO 98/47295 | 10/1998 |
| WO | WO 98/49813 | 11/1998 |
| WO | WO 98/52371 | 11/1998 |
| WO | WO 98/57474 | 12/1998 |
| WO | WO 98/58476 | 12/1998 |
| WO | WO 99/01969 | 1/1999 |

OTHER PUBLICATIONS

Mary Carmen Cupito; Emerging technologies: Has Their time come? Enterprise Integration; Health Management Technology; Dec. 1998.

Toh Han Shih; Online life–line; Wired for Business; Singapore Business Times; Dec. 1998.

(List continued on next page.)

Primary Examiner—Jack Choules
Assistant Examiner—Cheryl Lewis
(74) Attorney, Agent, or Firm—Morrison & Foerster LLP

(57) ABSTRACT

A system is disclosed that facilitates web-based information retrieval and display system. A wireless phone or similar hand-held wireless device with Internet Protocol capability is combined with other peripherals to provide a portable portal into the Internet. The wireless device prompts a user to input information of interest to the user. This information is transmitted a query to a service routine (running on a Web server). The service routine then queries the Web to find price, shipping and availability information from various Web suppliers. This information is then available for use by application programs such as wordprocessors, e-mail, accounting, graphical editors and other user tools. The system provides an innovative collaborative interface to many popular user applications that are useful in a mobile environment.

6 Claims, 30 Drawing Sheets

OTHER PUBLICATIONS

Chris Bradley; Remote and Mobile Computing with TCP/IP; Enterprise Systems Journal; Jan. 1998.

Enhanced Services: Telecom customers will soon have one–stop, easy–to–use access to their services portfolio form anywhere, at any time, and in any way; EDGE, on & about AT&T; May 1997.

Nokia, Ericsson, Unwired Planet and Motorola unite to create an open common protocol for interactive wireless applications; Jun. 26, 1997.

Unisource in GSM trial of mobile electronic banking and shopping; Mobile Communications: Mar. 20, 1997.

Dynamic Mobile Data Announces Mobile Server Wireless Solution For Enterprise and Internet Access; Mar. 1999.

Philip R. Cohen, Adam Cheyer, Michelle Wang, Soon Cheol Baeg; An Open Agent Architecture; Software Agent Papers, AAAI Spring Symposium 1994.

Bob Emmerson; The Mobile Intranet: The next generation of GSM services will offer faster data rates and smarter messaging; May 1998; BYTE Magazine.

Timo Alanko, Markku Kojo, Mika Liljeberg; Mobile access to the Internet; a mediator–based solution; Internet Research; Electronics Networking Applications and Policy vol. 9, No. 1, pp. 58–65, 1999.

Andrezej Duda, Stephane Perret; A Network Programming Model for Mobile Applications and Information Access; Proceedings JENC7, No date.

Chu–Sing Yang, Kun–da Wu, Chun–Wei Tseng; Support an Efficient Connection for Mobile IP; Proceedings, Ninth International Workshop on Database and Expert Systems Applications; Aug. 1998, IEE, Computer Society.

Katia Sycara, Anandeep S. Pannu; The RETSINA Multi-agent System; Towards Integrating Planning, Execution and Information Gathering; Proceedings of the Second International Conference on Autonomous Agents, May 1998.

* cited by examiner

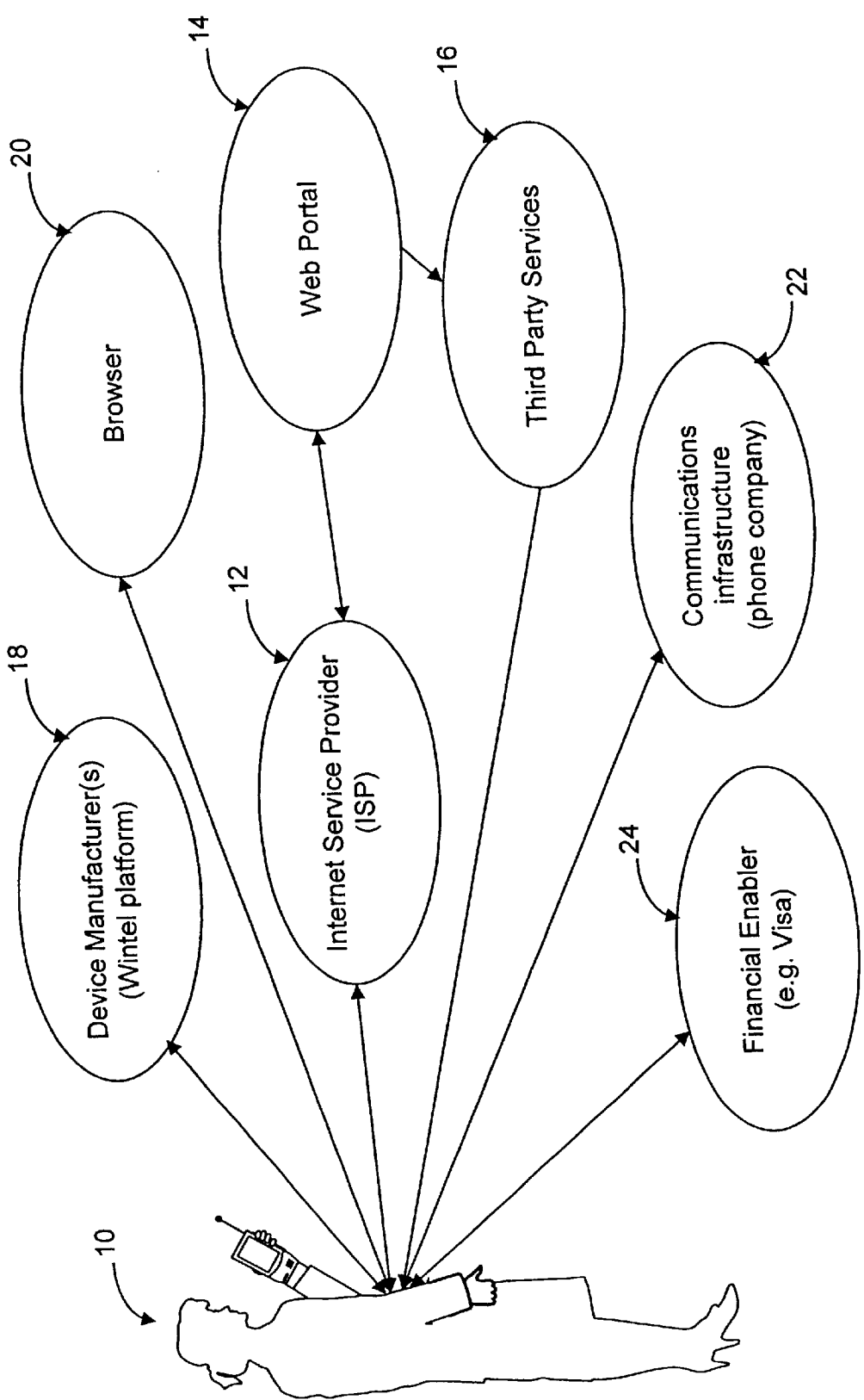
Prior Art Fig. 1A

MOBILE COMMUNICATION AND COMPUTING SYSTEM AND METHOD

CROSS-REFERENCE TO RELATED APPLICATION

The following applications are related to the present application in that they were filed on the same date while claiming different inventions, are assigned to the same assignee and, except for U.S. Pat. No. 6,199,099, are co-pending applications.

U.S. Pat. No. 6,199,099 B1, Issued on Mar. 6, 2001 titled "System, Method and Article of Manufacture For a Mobile Communication Network Utilizing A Distributed Communication Network" (Ser. No. 09/263,143 filed Mar. 5, 1999);

Ser. No. 091263,927, filed on Mar. 5, 1999, titled "Mobile Communication System and Method For A Shopper Agent", pending;

Ser. No. 09/263,251, filed on Mar. 5, 1999, titled "A System for Utilizing a Transaction Interface In A Mobile Communication Network", pending;

Ser. No. 09/263,926, filed on Mar. 5, 1999, titled "System, Method and Article of Manufacture For Advanced Mobile Health Care Processing", pending;

Ser. No. 09/263,252, filed on Mar. 5, 1999, titled "System, Method and Article of Manufacture For Mobile Communication Utilizing an Interface Support Framework", pending ;

Ser. No. 09/263,920, filed on Mar. 5, 1999, titled "Dynamic Configuration System and Method for a Mobile Communication Network", pending.

FIELD OF THE INVENTION

The present invention relates to agent based systems and more particularly to a mobile computing environment that accesses the Internet to obtain product information for a user and provides tools for collaborative computing.

BACKGROUND OF THE INVENTION

Computer assistance in all environments is increasingly necessary as computer technology becomes increasingly embedded in society. Mobile computing technology addresses this issue by allowing the individual to access computer related information at all times and in all environments.

One of the first major advances in mobile computer technology was the Personal Digital Assistant (PDA). A PDA allowed a user to access computer related information, yet fitted in the palm of the hand. Utilizing a PDA the user could organize personal affairs, write notes, calculate equations, and record contact numbers an address book. In addition, PDAs were usually capable of interfacing with a desktop computer, typically through a wire connection. The connection allowed the PDA to download information and upload information, with the desktop computer. Later developments gave the PDA wireless capabilities. The wireless capabilities allowed the PDA to interact with other computers that were not physically connected to the PDA.

Wireless PDAs could communicate with computers that were connected to the World Wide Web, and soon led to PDAs capable of Web browsing. One of the first companies to develop Web browsing capabilities for PDAs was Intercom. Intercom's Falcon Mobile Server allowed PDAs with Web functions to directly connect to a host computer. Just by installing the software onto the host server, PDA terminals were able to access information through the World Wide Web. Currently, more integration in mobile computing is desired. Nokia, an Irving Tex. company, has partially addressed the integration issue by developing the Nokia 9000 wireless voice phone. The Nokia 9000 includes a small keyboard, a specialized Web browser from microbrowser vendor Unwired Planet, Inc., and a small VGA monitor. Nokia worked with Ericsson Inc, Motorola Inc. and Unwired Planet to establish the Wireless Application Protocol (WAP), a standardized browser technology and server format. WAP gave manufacturers a standard way to put data capability into wireless phones, and allowed carriers to do more over-the-air management. For example, if a carrier wanted a field trial of a new data service, the carrier could implement the service on a server, deliver it to a phone through the microbrowser and adjust the service if they found the service unsatisfactory.

Prior Art FIG. 1A is a diagram of prior art mobile computing solutions based on web portal networks. In the Prior Art, the user 10 must deal separately with each participant of the network. In the Prior Art mobile computing solution, the user 10 utilizes an Internet service provider (ISP) 12 to gain access to a web portal 14. The web portal 14 accesses third party services 16 which provide information directly to the user 10. However, in addition to dealing with the Internet Service Provider 12, the user 10 must purchase the wireless device from the device manufactures or retailers 18. In most cases the user 10 would also have to purchase the browser from the browser provider 20. Generally, the user would have to pay the wireless communication cost, leading to the user needing to deal with the phone company 22. And finally, any web purchases would lead to the user 10 needing to deal with the credit card company 24. It is obvious that a coordinated and packaged service would be an ideal mobile computing solution. Furthermore, a coordinated and packaged service which made use of agents would be highly desired.

Agent based technology has become increasingly important for use with applications designed to interact with a user for performing various computer based tasks in foreground and background modes. Agent software comprises computer programs that are set on behalf of users to perform routine, tedious and time-consuming tasks. To be useful to an individual user, an agent must be personalized to the individual user's goals, habits and preferences. Thus, there exists a substantial requirement for the agent to efficiently and effectively acquire user-specific knowledge from the user and utilize it to perform tasks on behalf of the user.

The concept of agency, or the user of agents, is well established. An agent is a person authorized by another person, typically referred to as a principal, to act on behalf of the principal. In this manner the principal empowers the agent to perform any of the tasks that the principal is unwilling or unable to perform. For example, an insurance agent may handle all of the insurance requirements for a principal, or a talent agent may act on behalf of a performer to arrange concert dates.

With the advent of the computer, a new domain for employing agents has arrived. Significant advances in the realm of expert systems enable computer programs to act on behalf of computer users to perform routine, tedious and other time-consuming tasks. These computer programs are referred to as "software agents."

Moreover, there has been a recent proliferation of computer and communication networks. These networks permit a user to access vast amounts of information and services without, essentially, any geographical boundaries. Thus, a software agent has a rich environment to perform a large number of tasks on behalf of a user. For example, it is now possible for an agent to make an airline reservation, purchase the ticket, and have the ticket delivered directly to a user. Similarly, an agent could scan the Internet and obtain information ranging from the latest sports or news to a particular graduate thesis in applied physics. Current solutions fail to apply agent technology to provide targeted acquisition of information for a user's upcoming events.

SUMMARY OF THE INVENTION

A system is disclosed that facilitates web-based information retrieval and display system. A wireless phone or similar hand-held wireless device with Internet Protocol capability is combined with other peripherals to provide a portable portal into the Internet. The wireless device prompts a user to input information of interest to the user. This information is transmitted a query to a service routine (running on a Web server). The service routine then queries the Web to find price, shipping and availability information from various Web suppliers. This information is formatted and displayed on the hand-held device's screen. The user may then use the hand-held device to place an order interactively. The system provides an innovative collaborative interface to many popular user applications that are useful in a mobile environment.

DESCRIPTION OF THE DRAWINGS

The foregoing and other objects, aspects and advantages are better understood from the following detailed description of a preferred embodiment of the invention with reference to the drawings, in which:

Prior Art FIG. 1A is a diagram of Prior Art mobile computing solutions based on web portal networks;

DETAILED DESCRIPTION

Figure 1:
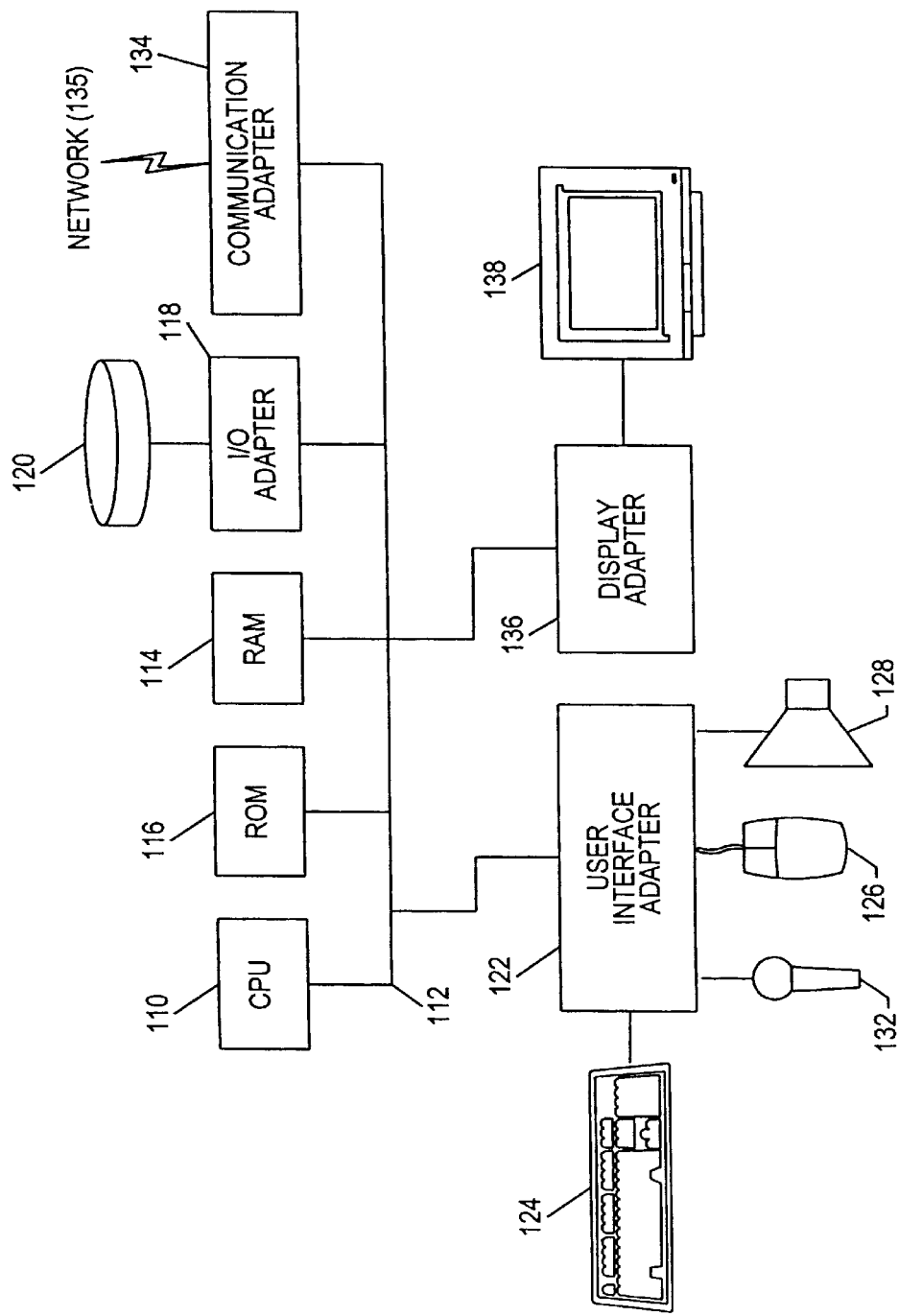
FIG. 1 is a block diagram of a representative hardware environment in accordance with a preferred embodiment.

A preferred embodiment of a system in accordance with the present invention is preferably practiced in the context of a personal computer such as an IBM compatible personal computer, Apple Macintosh computer or UNIX based workstation. A representative hardware environment is depicted in FIG. 1, which illustrates a typical hardware configuration of a workstation in accordance with a preferred embodiment having a central processing unit 110, such as a microprocessor, and a number of other units interconnected via a system bus 112. The workstation shown in FIG. 1 includes a Random Access Memory (RAM) 114, Read Only Memory (ROM) 116, an I/O adapter 118 for connecting peripheral devices such as disk storage units 120 to the bus 112, a user interface adapter 122 for connecting a keyboard 124, a mouse 126, a speaker 128, a microphone 132, and/or other user interface devices such as a touch screen (not shown) to the bus 112, communication adapter 134 for connecting the workstation to a communication network (e.g., a data processing network) and a display adapter 136 for connecting the bus 112 to a display device 138. The workstation typically has resident thereon an operating system such as the Microsoft Windows NT or Windows/95 Operating System (OS), the IBM OS/2 operating system, the MAC OS, or UNIX operating system. Those skilled in the art will appreciate that the present invention may also be implemented on platforms and operating systems other than those mentioned.

A preferred embodiment is written using JAVA, C, and the C++ language and utilizes object oriented programming methodology. Object oriented programming (OOP) has become increasingly used to develop complex applications. As OOP moves toward the mainstream of software design and development, various software solutions require adaptation to make use of the benefits of OOP. A need exists for these principles of OOP to be applied to a messaging interface of an electronic messaging system such that a set of OOP classes and objects for the messaging interface can be provided.

OOP is a process of developing computer software using objects, including the steps of analyzing the problem, designing the system, and constructing the program. An object is a software package that contains both data and a collection of related structures and procedures. Since it contains both data and a collection of structures and procedures, it can be visualized as a self-sufficient component that does not require other additional structures, procedures or data to perform its specific task. OOP, therefore, views a computer program as a collection of largely autonomous components, called objects, each of which is responsible for a specific task. This concept of packaging data, structures, and procedures together in one component or module is called encapsulation.

In general, OOP components are reusable software modules which present an interface that conforms to an object model and which are accessed at run-time through a component integration architecture. A component integration architecture is a set of architecture mechanisms which allow software modules in different process spaces to utilize each others capabilities or functions. This is generally done by assuming a common component object model on which to build the architecture.

It is worthwhile to differentiate between an object and a class of objects at this point. An object is a single instance of the class of objects, which is often just called a class. A class of objects can be viewed as a blueprint, from which many objects can be formed.

OOP allows the programmer to create an object that is a part of another object. For example, the object representing a piston engine is said to have a composition-relationship with the object representing a piston. In reality, a piston engine comprises a piston, valves and many other components; the fact that a piston is an element of a piston engine can be logically and semantically represented in OOP by two objects.

OOP also allows creation of an object that "depends from" another object. If there are two objects, one representing a piston engine and the other representing a piston engine wherein the piston is made of ceramic, then the relationship between the two objects is not that of composition. A ceramic piston engine does not make up a piston engine. Rather it is merely one kind of piston engine that has one more limitation than the piston engine; its piston is made of ceramic. In this case, the object representing the ceramic piston engine is called a derived object, and it inherits all of the aspects of the object representing the piston engine and adds further limitation or detail to it. The object representing the ceramic piston engine "depends from" the object representing the piston engine. The relationship between these objects is called inheritance.

When the object or class representing the ceramic piston engine inherits all of the aspects of the objects representing the piston engine, it inherits the thermal characteristics of a standard piston defined in the piston engine class. However, the ceramic piston engine object overrides these ceramic specific thermal characteristics, which are typically different from those associated with a metal piston. It skips over the original and uses new functions related to ceramic pistons. Different kinds of piston engines have different characteristics, but may have the same underlying functions associated with it (e.g., how many pistons in the engine, ignition sequences, lubrication, etc.). To access each of these functions in any piston engine object, a programmer would call the same functions with the same names, but each type of piston engine may have different/overriding implementations of functions behind the same name. This ability to hide different implementations of a function behind the same name is called polymorphism and it greatly simplifies communication among objects.

With the concepts of composition-relationship, encapsulation, inheritance and polymorphism, an object can represent just about anything in the real world. In fact, our logical perception of the reality is the only limit on determining the kinds of things that can become objects in object-oriented software. Some typical categories are as follows:

Objects can represent physical objects, such as automobiles in a traffic-flow simulation, electrical components in a circuit-design program, countries in an economics model, or aircraft in an air-traffic-control system.

Objects can represent elements of the computer-user environment such as windows, menus or graphics objects.

An object can represent an inventory, such as a personnel file or a table of the latitudes and longitudes of cities.

An object can represent user-defined data types such as time, angles, and complex numbers, or points on the plane.

With this enormous capability of an object to represent just about any logically separable matters, OOP allows the software developer to design and implement a computer program that is a model of some aspects of reality, whether that reality is a physical entity, a process, a system, or a composition of matter. Since the object can represent anything, the software developer can create an object which can be used as a component in a larger software project in the future.

If 90% of a new OOP software program consists of proven, existing components made from preexisting reusable objects, then only the remaining 10% of the new software project has to be written and tested from scratch. Since 90% already came from an inventory of extensively tested reusable objects, the potential domain from which an error could originate is 10% of the program. As a result, OOP enables software developers to build objects out of other, previously built, objects.

This process closely resembles complex machinery being built out of assemblies and sub-assemblies. OOP technology, therefore, makes software engineering more like hardware engineering in that software is built from existing components, which are available to the developer as objects. All this adds up to an improved quality of the software as well as an increased speed of its development.

Programming languages are beginning to fully support the OOP principles, such as encapsulation, inheritance, polymorphism, and composition-relationship. With the advent of the C++ language, many commercial software developers have embraced OOP. C++ is an OOP language that offers a fast, machine-executable code. Furthermore, C++ is suitable for both commercial-application and systems-programming projects. For now, C++ appears to be the most popular choice among many OOP programmers, but there is a host of other OOP languages, such as Smalltalk, common lisp object system (CLOS), and Eiffel. Additionally, OOP capabilities are being added to more traditional popular computer programming languages such as Pascal.

The benefits of object classes can be summarized, as follows:

- Objects and their corresponding classes break down complex programming problems into many smaller, simpler problems.
- Encapsulation enforces data abstraction through the organization of data into small, independent objects that can communicate with each other. Encapsulation protects the data in an object from accidental damage, but allows other objects to interact with that data by calling the object's member functions and structures.
- Subclassing and inheritance make it possible to extend and modify objects through deriving new kinds of objects from the standard classes available in the system. Thus, new capabilities are created without having to start from scratch.
- Polymorphism and multiple inheritance make it possible for different programmers to mix and match characteristics of many different classes and create specialized objects that can still work with related objects in predictable ways.
- Class hierarchies and containment hierarchies provide a flexible mechanism for modeling real-world objects and the relationships among them.

Libraries of reusable classes are useful in many situations, but they also have some limitations. For example:

- Complexity. In a complex system, the class hierarchies for related classes can become extremely confusing, with many dozens or even hundreds of classes.
- Flow of control. A program written with the aid of class libraries is still responsible for the flow of control (i.e., it must control the interactions among all the objects created from a particular library). The programmer has to decide which functions to call at what times for which kinds of objects.
- Duplication of effort. Although class libraries allow programmers to use and reuse many small pieces of code, each programmer puts those pieces together in a different way. Two different programmers can use the same set of class libraries to write two programs that do exactly the same thing but whose internal structure (i.e., design) may be quite different, depending on hundreds of small decisions each programmer makes along the way. Inevitably, similar pieces of code end up doing similar things in slightly different ways and do not work as well together as they should.

Class libraries are very flexible. As programs grow more complex, more programmers are forced to reinvent basic solutions to basic problems over and over again. A relatively new extension of the class library concept is to have a framework of class libraries. This framework is more complex and consists of significant collections of collaborating classes that capture both the small scale patterns and major mechanisms that implement the common requirements and design in a specific application domain. They were first developed to free application programmers from the chores involved in displaying menus, windows, dialog boxes, and other standard user interface elements for personal computers.

Frameworks also represent a change in the way programmers think about the interaction between the code they write and code written by others. In the early days of procedural programming, the programmer called libraries provided by the operating system to perform certain tasks, but basically the program executed down the page from start to finish, and the programmer was solely responsible for the flow of control. This was appropriate for printing out paychecks, calculating a mathematical table, or solving other problems with a program that executed in just one way.

The development of graphical user interfaces began to turn this procedural programming arrangement inside out. These interfaces allow the user, rather than program logic, to drive the program and decide when certain actions should be performed. Today, most personal computer software accomplishes this by means of an event loop which monitors the mouse, keyboard, and other sources of external events and calls the appropriate parts of the programmer's code according to actions that the user performs. The programmer no longer determines the order in which events occur. Instead, a program is divided into separate pieces that are called at unpredictable times and in an unpredictable order. By relinquishing control in this way to users, the developer creates a program that is much easier to use. Nevertheless, individual pieces of the program written by the developer still call libraries provided by the operating system to accomplish certain tasks, and the programmer must still determine the flow of control within each piece after being called by the event loop. Application code still "sits on top of" the system.

Even event loop programs require programmers to write a lot of code that should not need to be written separately for every application. The concept of an application framework carries the event loop concept further. Instead of dealing with all the nuts and bolts of constructing basic menus, windows, and dialog boxes and then making these things all work together, programmers using application frameworks start with working application code and basic user interface elements in place. Subsequently, they build from there by replacing some of the generic capabilities of the framework with the specific capabilities of the intended application.

Application frameworks reduce the total amount of code that a programmer has to write from scratch. However, because the framework is really a generic application that displays windows, supports copy and paste, and so on, the programmer can also relinquish control to a greater degree than event loop programs permit. The framework code takes care of almost all event handling and flow of control, and the programmer's code is called only when the framework needs it (e.g., to create or manipulate a proprietary data structure).

A programmer writing a framework program not only relinquishes control to the user (as is also true for event loop programs), but also relinquishes the detailed flow of control within the program to the framework. This approach allows the creation of more complex systems that work together in interesting ways, as opposed to isolated programs, having custom code, being created over and over again for similar problems.

Thus, as is explained above, a framework basically is a collection of cooperating classes that make up a reusable design solution for a given problem domain. It typically includes objects that provide default behavior (e.g., for menus and windows), and programmers use it by inheriting some of that default behavior and overriding other behavior so that the framework calls application code at the appropriate times.

There are three main differences between frameworks and class libraries:

Behavior versus protocol. Class libraries are essentially collections of behaviors that you can call when you want those individual behaviors in your program. A framework, on the other hand, provides not only behavior but also the protocol or set of rules that govern the ways in which behaviors can be combined, including rules for what a programmer is supposed to provide versus what the framework provides.

Call versus override. With a class library, the code the programmer instantiates objects and calls their member functions. It's possible to instantiate and call objects in the same way with a framework (i.e., to treat the framework as a class library), but to take full advantage of a framework's reusable design, a programmer typically writes code that overrides and is called by the framework. The framework manages the flow of control among its objects. Writing a program involves dividing responsibilities among the various pieces of software that are called by the framework rather than specifying how the different pieces should work together.

Implementation versus design. With class libraries, programmers reuse only implementations, whereas with frameworks, they reuse design. A framework embodies the way a family of related programs or pieces of software work. It represents a generic design solution that can be adapted to a variety of specific problems in a given domain. For example, a single framework can embody the way a user interface works, even though two different user interfaces created with the same framework might solve quite different interface problems.

Thus, through the development of frameworks for solutions to various problems and programming tasks, significant reductions in the design and development effort for software can be achieved. A preferred embodiment of the invention utilizes HyperText Markup Language (HTML) to implement documents on the Internet together with a general-purpose secure communication protocol for a transport medium between the client and the Newco. HTTP or other protocols could be readily substituted for HTML without undue experimentation. Information on these products is available in T. Berners-Lee, D. Connoly, "RFC 1866: Hypertext Markup Language—2.0" (November 1995); and R. Fielding, H, Frystyk, T. Berners-Lee, J. Gettys and J. C. Mogul, "Hypertext Transfer Protocol—HTTP/1.1: HTTP Working Group Internet Draft" (May 2, 1996). HTML is a simple data format used to create hypertext documents that are portable from one platform to another. HTML documents are SGML documents with generic semantics that are appropriate for representing information from a wide range of domains. HTML has been in use by the World-Wide Web global information initiative since 1990. HTML is an application of ISO Standard 8879:1986 Information Processing Text and Office Systems; Standard Generalized Markup Language (SGML).

To date, Web development tools have been limited in their ability to create dynamic Web applications which span from client to server and interoperate with existing computing resources. Until recently, HTML has been the dominant technology used in development of Web-based solutions. However, HTML has proven to be inadequate in the following areas:

Poor performance;

Restricted user interface capabilities;

Can only produce static Web pages;

Lack of interoperability with existing applications and data; and

Inability to scale.

Sun Microsystem's Java language solves many of the client-side problems by:

Improving performance on the client side;

Enabling the creation of dynamic, real-time Web applications; and

Providing the ability to create a wide variety of user interface components.

With Java, developers can create robust User Interface (UI) components. Custom "widgets" (e.g., real-time stock tickers, animated icons, etc.) can be created, and client-side performance is improved. Unlike HTML, Java supports the notion of client-side validation, offloading appropriate processing onto the client for improved performance. Dynamic, real-time Web pages can be created. Using the above-mentioned custom UI components, dynamic Web pages can also be created.

Sun's Java language has emerged as an industry-recognized language for "programming the Internet." Sun defines Java as: "a simple, object-oriented, distributed, interpreted, robust, secure, architecture-neutral, portable, high-performance, multithreaded, dynamic, buzzword-compliant, general-purpose programming language. Java supports programming for the Internet in the form of platform-independent Java applets." Java applets are small, specialized applications that comply with Sun's Java Application Programming Interface (API) allowing developers to add "interactive content" to Web documents (e.g., simple animations, page adornments, basic games, etc.). Applets execute within a Java-compatible browser (e.g., Netscape Navigator) by copying code from the server to client. From a language standpoint, Java's core feature set is based on C++. Sun's Java literature states that Java is basically "C++, with extensions from Objective C for more dynamic method resolution".

Another technology that provides similar function to JAVA is provided by Microsoft and ActiveX Technologies, to give developers and Web designers wherewithal to build dynamic content for the Internet and personal computers. ActiveX includes tools for developing animation, 3-D virtual reality, video and other multimedia content. The tools use Internet standards, work on multiple platforms, and are being supported by over 100 companies. The group's building blocks are called ActiveX Controls, small, fast components that enable developers to embed parts of software in hypertext markup language (HTML) pages. ActiveX Controls work with a variety of programming languages including Microsoft Visual C++, Borland Delphi, Microsoft Visual Basic programming system and, in the future, Microsoft's development tool for Java, code named "Jakarta." ActiveX Technologies also includes ActiveX Server Framework, allowing developers to create server applications. One of ordinary skill in the art readily recognizes that ActiveX could be substituted for JAVA without undue experimentation to practice the invention.

In accordance with a preferred embodiment, Background-Finder (BF) is implemented as an agent responsible for preparing an individual for an upcoming meeting by helping him/her retrieve relevant information about the meeting from various sources. BF receives input text in character form indicative of the target meeting. The input text is generated in accordance with a preferred embodiment by a calendar program that includes the time of the meeting. As the time of the meeting approaches, the calendar program is queried to obtain the text of the target event and that information is utilized as input to the agent. Then, the agent parses the input meeting text to extract its various components such as title, body, participants, location, time etc. The system also performs pattern matching to identify particular meeting fields in a meeting text. This information is utilized to query various sources of information on the web and obtain relevant stories about the current meeting to send back to the calendaring system. For example, if an individual has a meeting with Netscape and Microsoft to talk about their disputes, and would obtain this initial information from the calendaring system. It will then parse out the text to realize that the companies in the meeting are "Netscape" and "Microsoft" and the topic is "disputes." Then, the system queries the web for relevant information concerning the topic. Thus, in accordance with an objective of the invention, the system updates the calendaring system and eventually the user with the best information it can gather to prepare the user for the target meeting. In accordance with a preferred embodiment, the information is stored in a file that is obtained via selection from a link imbedded in the calendar system.

PROGRAM ORGANIZATION

A computer program in accordance with a preferred embodiment is organized in five distinct modules: BF.Main, BF.Parse, Background Finder.Error, BF.PatternMatching and BF.Search. There is also a frmMain which provides a user interface used only for debugging purposes. The executable programs in accordance with a preferred embodiment never execute with the user interface and should only return to the calendaring system through Microsoft's Winsock control. A preferred embodiment of the system executes in two different modes which can be specified under the command line sent to it by the calendaring system. When the system runs in simple mode, it executes a keyword query to submit to external search engines. When executed in complex mode, the system performs pattern matching before it forms a query to be sent to a search engine.

DATA STRUCTURES

The system in accordance with a preferred embodiment utilizes three user defined structures:

1. TMeetingRecord;
2. TPatternElement; and
3. TPatternRecord.

The user-defined structure, tMeetingRecord, is? used to store all the pertinent information concerning a single meeting. This info includes userID, an original description of the meeting, the extracted list of keywords from the title and body of meeting etc. It is important to note that only one meeting record is created per instance of the system in accordance with a preferred embodiment. This is because each time the system is spawned to service an upcoming meeting, it is assigned a task to retrieve information for only one meeting. Therefore, the meeting record created corresponds to the current meeting examined. ParseMeetingText populates this meeting record and it is then passed around to provide information about the meeting to other functions.

If GoPatternMatch can bind any values to a particular meeting field, the corresponding entries in the meeting record is also updated. The structure of tMeetingrecord with each field described in parentheses is provided below in accordance with a preferred embodiment.

| A.1.1.1.1.1 | Public Type tMeetingRecord |
| --- | --- |
| sUserID As String | (user id given by Munin) |
| sTitleOrig As String | (original non stop listed title we need to keep around to send back to Munin) |
| sTitleKW As String | (stoplisted title with only keywords) |
| sBodyKW As String | (stoplisted body with only keywords) |
| sCompany() As String | (companys identified in title or body through pattern matching) |
| sTopic() As String | (topics identified in title or body through pattern matching) |
| sPeople() As String | (people identified in title or body through pattern matching) |
| sWhen() As String | (time identified in title or body through pattern matching) |
| sWhere() As String | (location identified in title or body through pattern matching) |
| sLocation As String | (location as passed in by Munin) |
| sTime As String | (time as passed in by Munin) |
| sParticipants() As String | (all participants engaged as passed in by Munin) |
| sMeetingText As String | (the original meeting text w/o userid) |
| End Type | |

There are two other structures which are created to hold each individual pattern utilized in pattern matching. The record tAPattermRecord is an array containing all the components/elements of a pattern. The type tAPatternElement is an array of strings which represent an element in a pattern. Because there may be many "substitutes" for each element, we need an array of strings to keep track of what all the substitutes are. The structures of tAPatternElement and tAPattemRecord are presented below in accordance with a preferred embodiment.

Public Type tAPattemElement
    elementArray() As String
End Type
Public Type TPatternRecord
    patternArray() As tAPattemElement
End Type

COMMON USER DEFINED CONSTANTS

Many constants are defined in each declaration section of the program which may need to be updated periodically as part of the process of maintaining the system in accordance with a preferred embodiment. The constants are accessible to allow dynamic configuration of the system to occur as updates for maintaining the code.

Included in the following tables are lists of constants from each module which I thought are most likely to be modified from time to time. However, there are also other constants used in the code not included in the following list. It does not mean that these non-included constants will never be changed. It means that they will change much less frequently.

| CONSTANT | PRESET VALUE | USE |
| --- | --- | --- |
| MSGTOMUNIN_TYPE | 6 | Define the message number used to identify messages between BF and Munin |

-continued

| CONSTANT | PRESET VALUE | USE |
|---|---|---|
| IP_ADDRESS_ MUNIN | "10.2.100.48" | Define the IP address of the machine in which Munin and BF are running on so they can transfer data through UDP. |
| PORT_MUNIN | 7777 | Define the remote port in which we are operating on. |
| TIMEOUT_AV | 60 | Define constants for setting time out in inet controls |
| TIMEOUT_NP | 60 | Define constants for setting time out in inet controls |
| CMD_ SEPARATOR | "\" | Define delimiter to tell which part of Munin's command represents the beginning of our input meeting text |
| OUTPARAM_ SEPARATOR | "::" | Define delimiter for separating out different portions of the output. The separator is for delimiting the msg type, the user id, the meeting title and the beginning of the actual stories retrieved. |

For the Search Module (BF.Search):

| CONSTANT | CURRENT VALUE | USE |
|---|---|---|
| PAST_NDAYS | 5 | Define number of days you want to look back for AltaVista articles. Doesn't really matter now because we aren't really doing a news search in alta vista. We want all info. |
| CONNECTOR_AV_ URL | "+AND+" | Define how to connect keywords. We want all our keywords in the string so for now use AND. If you want to do an OR or something, just change connector. |
| CONNECTOR_NP_ URL | "+AND+" | Define how to connect keywords. We want all our keywords in the string so for now use AND. If you want to do an OR or something, just change connector. |
| NUM_NP_STORIES | 3 | Define the number of stories to return back to Munin from NewsPage. |
| NUM_AV_STORIES | 3 | Define the number of stories to return back to Munin from AltaVista. |

For the Parse Module (BF.Parse):

| CONSTANT | CURRENT VALUE | USE |
|---|---|---|
| PORTION_ SEPARATOR | "::" | Define the separator between different portions of the meeting text sent in by Munin. For example in "09::Meet with Chad::about life::Chad \| Denise::::::" "::" is the separator between different parts of the meeting text. |
| PARTICIPANT_ SEPARATOR | "\|" | Define the separator between each participant in the participant list portion of the original meeting text. Refer to example above. |

For Pattern Matching Module (BFPatternMatch): There are no constants in this module which require frequent updates.

General Process Flow

Figure 2:
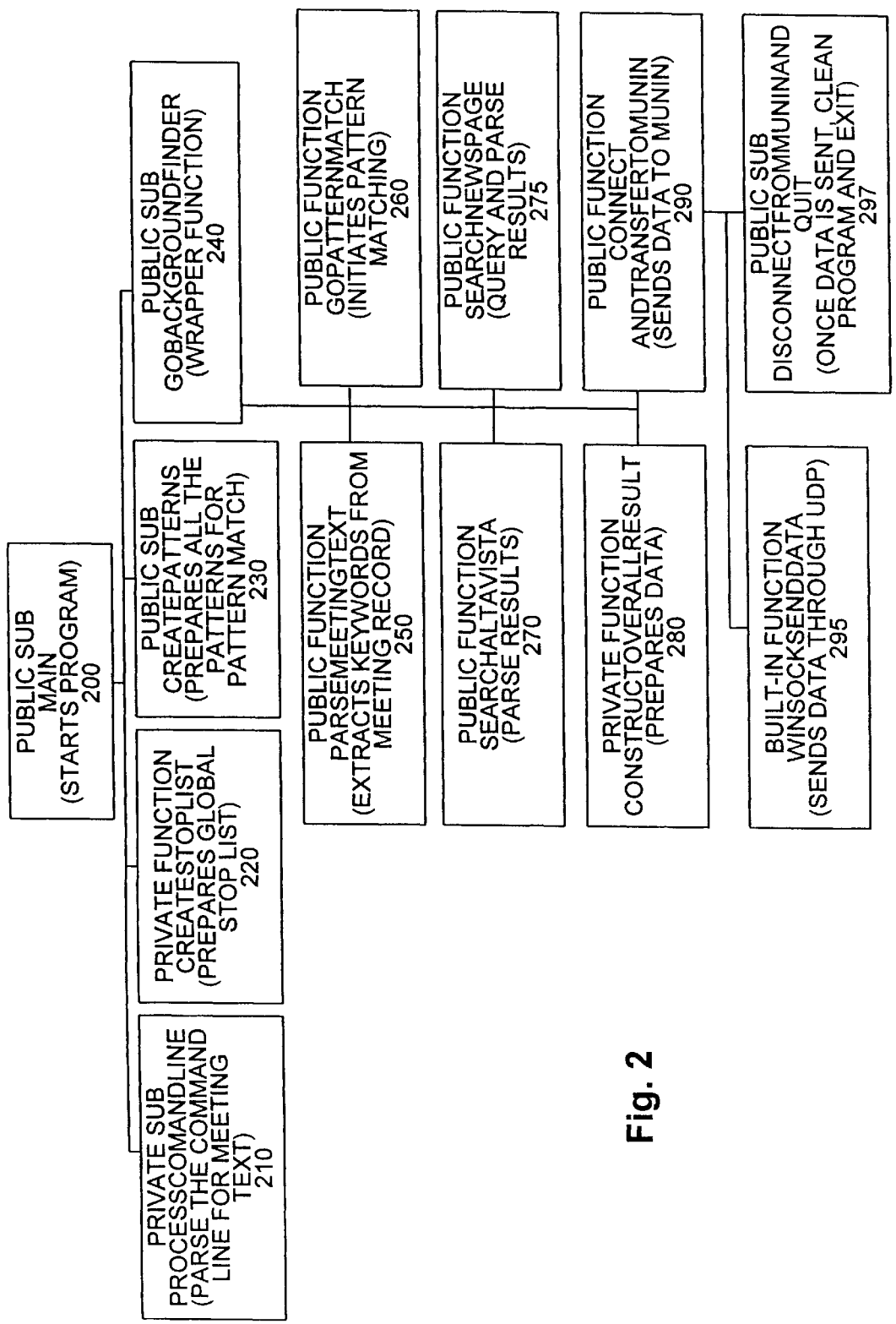
FIG. 2 is a flowchart of the system in accordance with a preferred embodiment.

The best way to depict the process flow and the coordination of functions between each other is with the five flowcharts illustrated in FIGS. 2 to 6. FIG. 2 depicts the overall process flow in accordance with a preferred embodiment. Processing commences at the top of the chart at function block 200 which launches when the program starts. Once the application is started, the command line is parsed to remove the appropriate meeting text to initiate the target of the background find operation in accordance with a preferred embodiment as shown in function block 210. A global stop list is generated after the target is determined as shown in function block 220. Then, all the patterns that are utilized for matching operations are generated as illustrated in function block 230. Then, by tracing through the chart, function block 200 invokes GoBF 240 which is responsible for logical processing associated with wrapping the correct search query information for the particular target search engine. For example, function block 240 flows to function block 250 and it then calls GoPatternMatch as shown in function block 260. To see the process flow of GoPattemMatch, we swap to the diagram titled "Process Flow for BF's Pattern Matching Unit."

One key thing to notice is that functions depicted at the same level of the chart are called by in sequential order from left to right (or top to bottom) by their common parent function. For example, Main 200 calls ProcessCommandLine 210, then CreateStopListist 220, then CreatePatterns 230, then GoBackgroundFinder 240. FIGS. 3 to 6 detail the logic for the entire program, the parsing unit, the pattern matching unit and the search unit respectively. FIG. 6 details the logic determinative of data flow of key information through BackgroundFinder, and shows the functions that are responsible for creating or processing such information.

DETAILED SEARCH ARCHITECTURE UNDER THE SIMPLE QUERY MODE

SEARCH ALTA VISTA (Function block 270 of FIG. 2)

The Alta Vista search engine utilizes the identifies and returns general information about topics related to the current meeting as shown in function block 270 of FIG. 2. The system in accordance with a preferred embodiment takes all the keywords from the title portion of the original meeting text and constructs an advanced query to send to Alta Vista. The keywords are logically combined together in the query. The results are also ranked based on the same set of keywords. One of ordinary skill in the art will readily comprehend that a date restriction or publisher criteria could be facilitated on the articles we want to retrieve. A set of top ranking stories are returned to the calendaring system in accordance with a preferred embodiment.

NEWS PAGE (Function block 275 of FIG. 2)

The NewsPage search system is responsible for giving us the latest news topics related to a target meeting. The system takes all of the keywords from the title portion of the original meeting text and constructs a query to send to the NewsPage search engine. The keywords are logically combined together in the query. Only articles published recently are retrieved. The Newspage search system provides a date restriction criteria that is settable by a user according to the user's preference. The top ranking stories are returned to the calendaring system.

Figure 3:
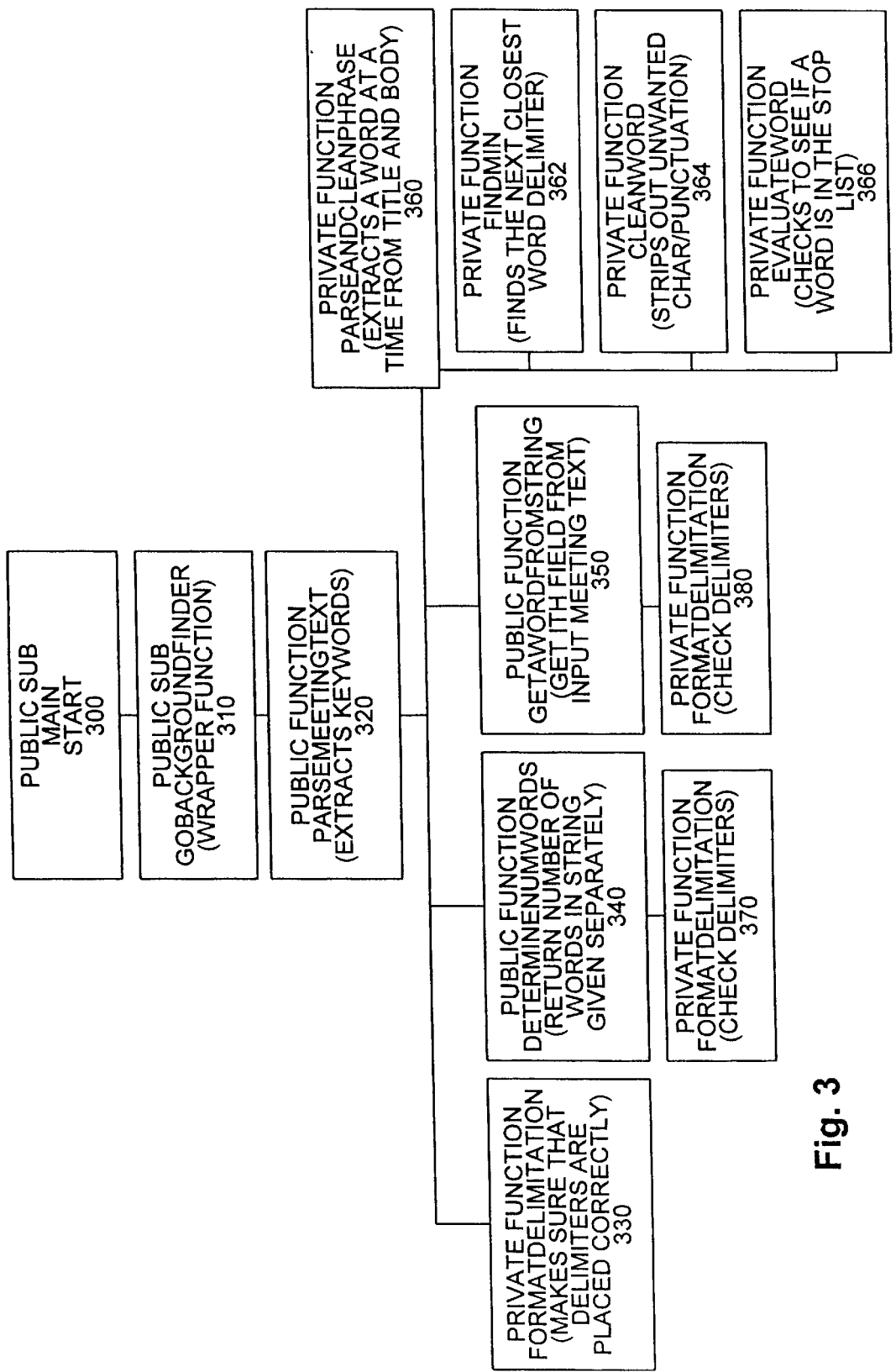
FIG. 3 is a flowchart of a parsing unit of the system in accordance with a preferred embodiment.

FIG. 3 is a user profile data model in accordance with a preferred embodiment. Processing commences at function block 300 which is responsible for invoking the program from the main module. Then, at function block 310, a wrapper function is invoked to prepare for the keyword extraction processing in function block 320. After the keywords are extracted, then processing flows to function block 330 to determine if the delimiters are properly positioned. Then, at function block 340, the number of words in a particular string is calculated and the delimiters for the particular field are and a particular field from the meeting text is retrieved at function block 350. Then, at function block 380, the delimiters of the string are again checked to assure they are placed appropriately. Finally, at function block 360, the extraction of each word from the title and body of the message is performed a word at a time utilizing the logic in function block 362 which finds the next closest word delimiter in the input phrase, function block 364 which strips unnecessary materials from a word and function block 366 which determines if a word is on the stop list and returns an error if the word is on the stop list.

PATTERN MATCHING IN ACCORDANCE WITH A PREFERRED EMBODIMENT

The limitations associated with a simple searching method include the following:

1. Because it relies on a stoplist of unwanted words in order to extract from the meeting text a set of keywords, it is limited by how comprehensive the stoplist is. Instead of trying to figure out what parts of the meeting text we should throw away, we should focus on what parts of the meeting text we want.
2. A simple search method in accordance with a preferred embodiment only uses the keywords from a meeting title to form queries to send to Alta Vista and NewsPage. This ignores an alternative source of information for the query, the body of the meeting notice. We cannot include the keywords from the meeting body to form our queries because this often results in queries which are too long and so complex that we often obtain no meaningful results.
3. There is no way for us to tell what each keyword represents. For example, we may extract "Andy" and "Grove" as two keywords. However, a simplistic search has no way knowing that "Andy Grove" is in fact a person's name. Imagine the possibilities if we could somehow intelligently guess that "Andy Grove" is a person's name. Information such as where he is employed and currently resides.
4. In summary, by relying solely on a stoplist to parse out unnecessary words, we suffer from "information overload".

PATTERN MATCHING OVERCOMES THESE LIMITATIONS IN ACCORDANCE WITH A PREFERRED EMBODIMENT

Here is how the pattern matching system can address each of the corresponding issues above in accordance with a preferred embodiment.

1. By doing pattern matching, we match up only parts of the meeting text that we want and extract those parts.
2. By performing pattern matching on the meeting body and extracting only the parts from the meeting body that we want. Our meeting body will not go to complete waste then.
3. Pattern matching is based on a set of templates that we specify, allowing us to identify people names, company names and other items from a meeting text.
4. In summary, with pattern matching, we no longer suffer from information overload. Of course, the big problem is how well our pattern matching works. If we rely exclusively on artificial intelligence processing, we do not have a 100% hit rate. We are able to identify about 20% of all company names presented to us.

PATTERNS

A pattern in the context of a preferred embodiment is a template specifying the structure of a phrase we are looking for in a meeting text. The patterns supported by a preferred embodiment are selected because they are templates of phrases which have a high probability of appearing in someone's meeting text. For example, when entering a meeting in a calendar, many would write something such as "Meet with Bob Dutton from Stanford University next Tuesday." A common pattern would then be something like the word "with" followed by a person's name (in this example it is Bob Dutton) followed by the word "from" and ending with an organization's name (in this case, it is Stanford University).

PATTERN MATCHING TERMINOLOGY

The common terminology associated with pattern matching is provided below.

Pattern: a pattern is a template specifying the structure of a phrase we want to bind the meeting text to. It contains sub units.

Element: a pattern can contain many sub-units. These subunits are called elements. For example, in the pattern "with $PEOPLE$ from $COMPANY$", "with" "$PEOPLE$" "from" "$COMPANY$" are all elements.

Placeholder: a placeholder is a special kind of element in which we want to bind a value to. Using the above example, "$PEOPLE$" is a placeholder.

Indicator: an indicator is another kind of element which we want to find in a meeting text but no value needs to bind to it. There may be often more than one indicator we are looking for in a certain pattern. That is why an indicator is not an "atomic" type.

Substitute: substitutes are a set of indicators which are all synonyms of each other. Finding any one of them in the input is good.

There are five fields which are identified for each meeting:

| | |
|---|---|
| ♦ Company | ($COMPANY$) |
| ♦ People | ($PEOPLE$) |
| ♦ Location | ($LOCATION$) |
| ♦ Time | ($TIME$) |
| ♦ Topic | ($TOPIC_UPPER$) or ($TOPIC_ALL$) |

In parentheses are the placeholders I used in my code as representation of the corresponding meeting fields.

Each placeholder has the following meaning:

$COMPANY$: binds a string of capitalized words (e.g., Meet with Joe Carter of <Andersen Consulting>)

$PEOPLE$: binds series of string of two capitalized words potentially connected by ",", "and" or "&" (e.g., Meet with Joe <Carter> of Andersen Consulting, Meet with <Joe Carter and Luke Hughes> of Andersen Consulting)

$LOCATION$: binds a string of capitalized words (e.g., Meet Susan at <Palo Alto Square>)

$TIME$: binds a string containing the format #:## (e.g., Dinner at <6:30 pm>)

$TOPIC_UPPER$: binds a string of capitalized words for our topic (e.g., <Stanford Engineering Recruiting> Meeting to talk about new hires).

$TOPIC_ALL$: binds a string of words without really caring if it's capitalized or not. (e.g., Meet to talk about <ubiquitous computing>)

Here is a table representing all the patterns supported by BF. Each pattern belongs to a pattern group. All patterns within a pattern group share a similar format and they only differ from each other in terms of what indicators are used as substitutes. Note that the patterns which are grayed out are also commented in the code. BF has the capability to support these patterns but we decided that matching these patterns is not essential at this point.

| PAT GRP | PAT # | PATTERN | EXAMPLE |
|---|---|---|---|
| 1 | a | $PEOPLE$ of $COMPANY$ | Paul Maritz of Microsoft |
|   | b | $PEOPLE$ from $COMPANY$ | Bill Gates, Paul Allen and Paul Maritz from Microsoft |
| 2 | a | $TOPIC_UPPER$ meeting | Push Technology Meeting |
|   | b | $TOPIC_UPPER$ mtg | Push Technology Mtg |
|   | c | $TOPIC_UPPER$ demo | Push Technology demo |
|   | d | $TOPIC_UPPER$ interview | Push Technology interview |
|   | e | $TOPIC_UPPER$ presentation | Push Technology presentation |
|   | f | $TOPIC_UPPER$ visit | Push Technology visit |
|   | g | $TOPIC_UPPER$ briefing | Push Technology briefing |
|   | h | $TOPIC_UPPER$ discussion | Push Technology discussion |
|   | i | $TOPIC_UPPER$ workshop | Push Technology workshop |
|   | j | $TOPIC_UPPER$ prep | Push Technology prep |
|   | k | $TOPIC_UPPER$ review | Push Technology review |
|   | l | $TOPIC_UPPER$ lunch | Push Technology lunch |
|   | m | $TOPIC_UPPER$ project | Push Technology project |
|   | n | $TOPIC_UPPER$ projects | Push Technology projects |
| 3 | a | $COMPANY$ corporation | Intel Corporation |
|   | b | $COMPANY$ corp. | IBM Corp. |
|   | c | $COMPANY$ systems | Cisco Systems |
|   | d | $COMPANY$ limited | IBM limited |
|   | e | $COMPANY$ ltd | IBM ltd |
| 4 | a | about $TOPIC_ALL$ | About intelligent agents technology |
|   | b | discuss $TOPIC_ALL$ | Discuss intelligent agents technology |
|   | c | show $TOPIC_ALL$ | Show the client our intelligent agents technology |
|   | d | re: $TOPIC_ALL$ | re: intelligent agents technology |
|   | e | review $TOPIC_ALL$ | Review intelligent agents technology |
|   | f | agenda | The agenda is as follows: --clean up --clean up --clean up |
|   | g | agenda: $TOPIC_ALL$ | Agenda: --demo client intelligent agents technology. --demo ecommerce. |
| 5 | a | w/$PEOPLE$ of $COMPANY$ | Meet w/Joe Carter of Andersen Consulting |
|   | b | w/$PEOPLE$ from $COMPANY$ | Meet w/Joe Carter from Andersen Consulting |
| 6 | a | w/$COMPANY$ per $PEOPLE$ | Talk w/Intel per Jason Foster |
| 7 | a | At $TIME$ | At 3:00 pm |
|   | b | Around $TIME$ | Around 3:00 pm |
| 8 | a | At $LOCATION$ | At LuLu's resturant |
|   | b | In $LOCATION$ | in Santa Clara |
| 9 | a | Per $PEOPLE$ | per Susan Butler |
| 10 | a | call w/$PEOPLE$ | Conf call w/John Smith |
|   | B | call with $PEOPLE$ | Conf call with John Smith |
| 11 | A | prep for $TOPIC_ALL$ | Prep for London meeting |
|   | B | preparation for $TOPIC_ALL$ | Preparation for London meeting |

Figure 4:
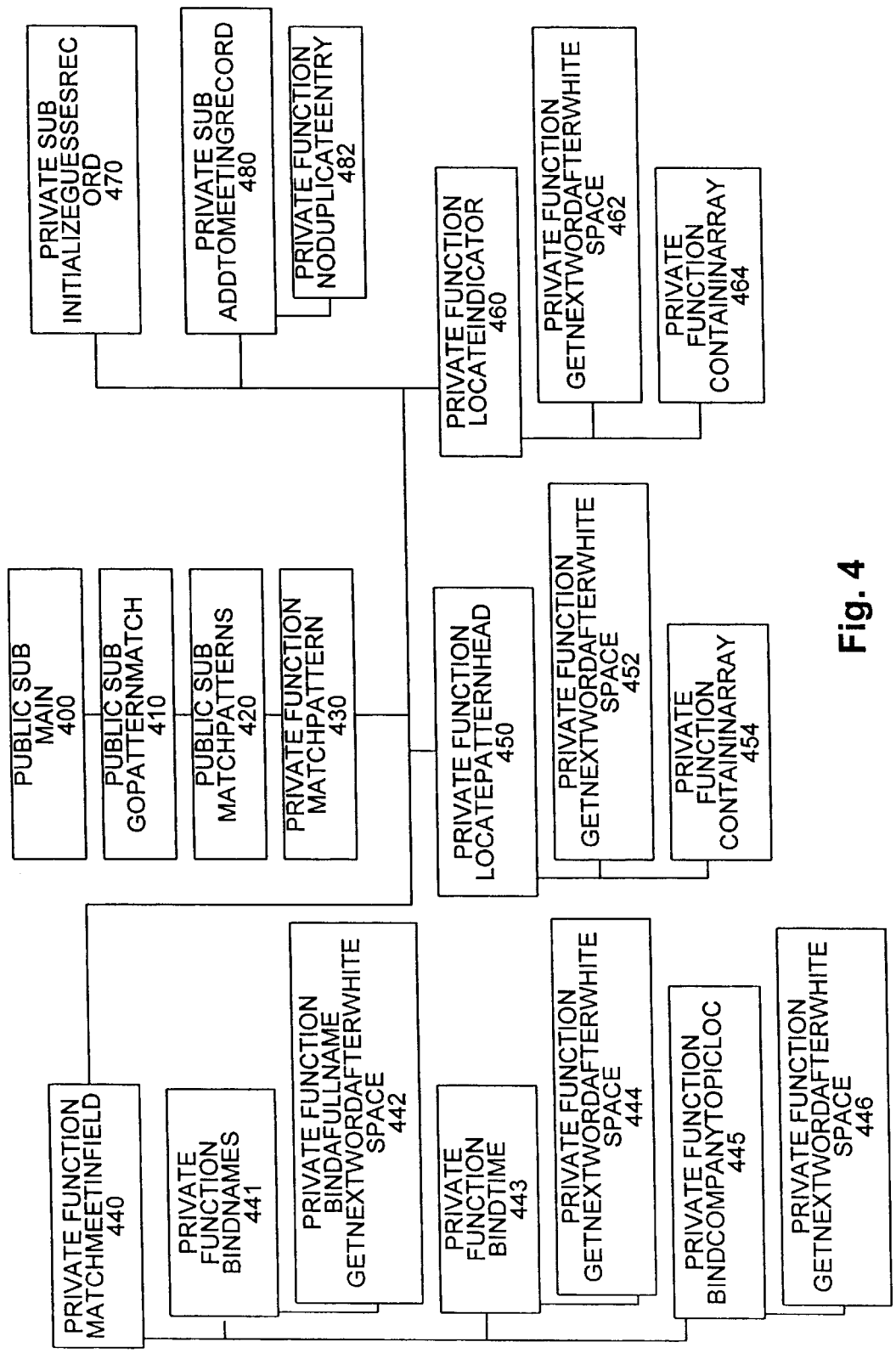
FIG. 4 is a flowchart for pattern matching in accordance with a preferred embodiment.

FIG. 4 is a detailed flowchart of pattern matching in accordance with a preferred embodiment. Processing commences at function block 400 where the main program invokes the pattern matching application and passes control to function block 410 to commence the pattern match processing. Then, at function block 420, the wrapper function loops through to process each pattern which includes determining if a part of the text string can be bound to a pattern as shown in function block 430. Then, at function block 440, various placeholders are bound to values if they exist, and in function block 441, a list of names separated by punctuation are bound, and at function block 442 a full name is processed by finding two capitalized words as a full name and grabbing the next letter after a space after a word to determine if it is capitalized. Then, at function block 443, time is parsed out of the string in an appropriate manner and the next word after a blank space in function block 444. Then, at function block 445, the continuous phrases of capitalized words such as company, topic or location are bound and in function block 446, the next word after the blank is obtained for further processing in accordance with a preferred embodiment. Following the match meeting field processing, function block 450 is utilized to locate an indicator which is the head of a pattern, the next word after the blank is obtained as shown in function block 452 and the word is checked to determine if the word is an indicator as shown in function block 454. Then, at function block 460, the string is parsed to locate an indicator which is not at the end of the pattern and the next word after unnecessary white space such as that following a line feed or a carriage return is processed as shown in function block 462 and the word is analyzed to determine if it is an indicator as shown in function block 464. Then, in function block 470, the temporary record is reset to the null set to prepare it for processing the next string and at function block 480, the meeting record is updated and at function block 482 a check is performed to determine if an entry is already made to the meeting record before parsing the meeting record again.

USING THE IDENTIFIED MEETING FIELDS

Now that we have identified fields within the meeting text which we consider important, there are quite a few things we can do with it. One of the most important applications of pattern matching is of course to improve the query we construct which eventually gets submitted to Alta Vista and News Page. There are also a lot of other options and enhancements which exploit the results of pattern matching that we can add to BF. These other options will be described in the next section. The goal of this section is to give the reader a good sense of how the results obtained from pattern matching can be used to help us obtain better search results.

Figure 5:
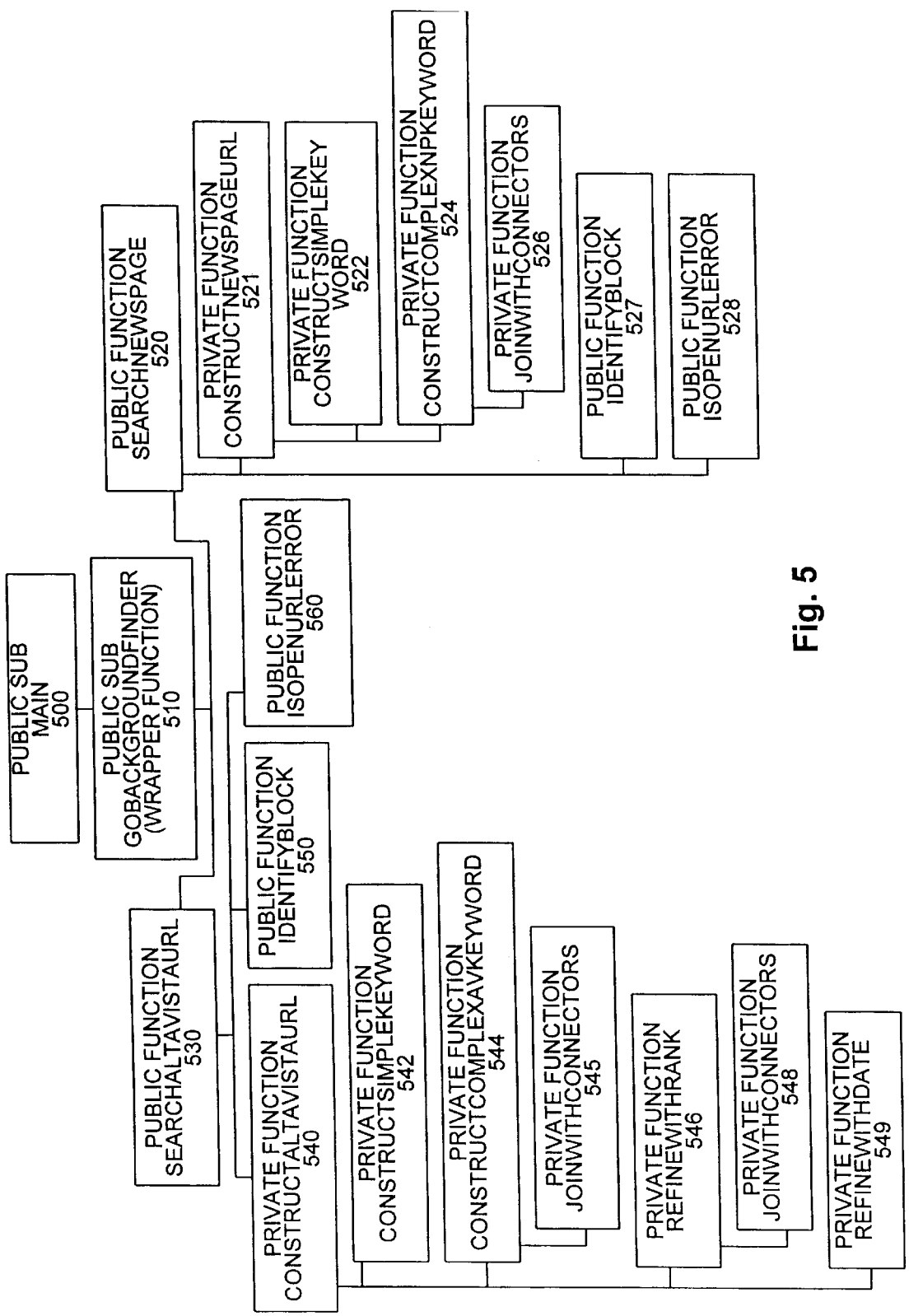
FIGS. 5 is a flowchart for a search unit in accordance with a preferred embodiment.
Figure 6:
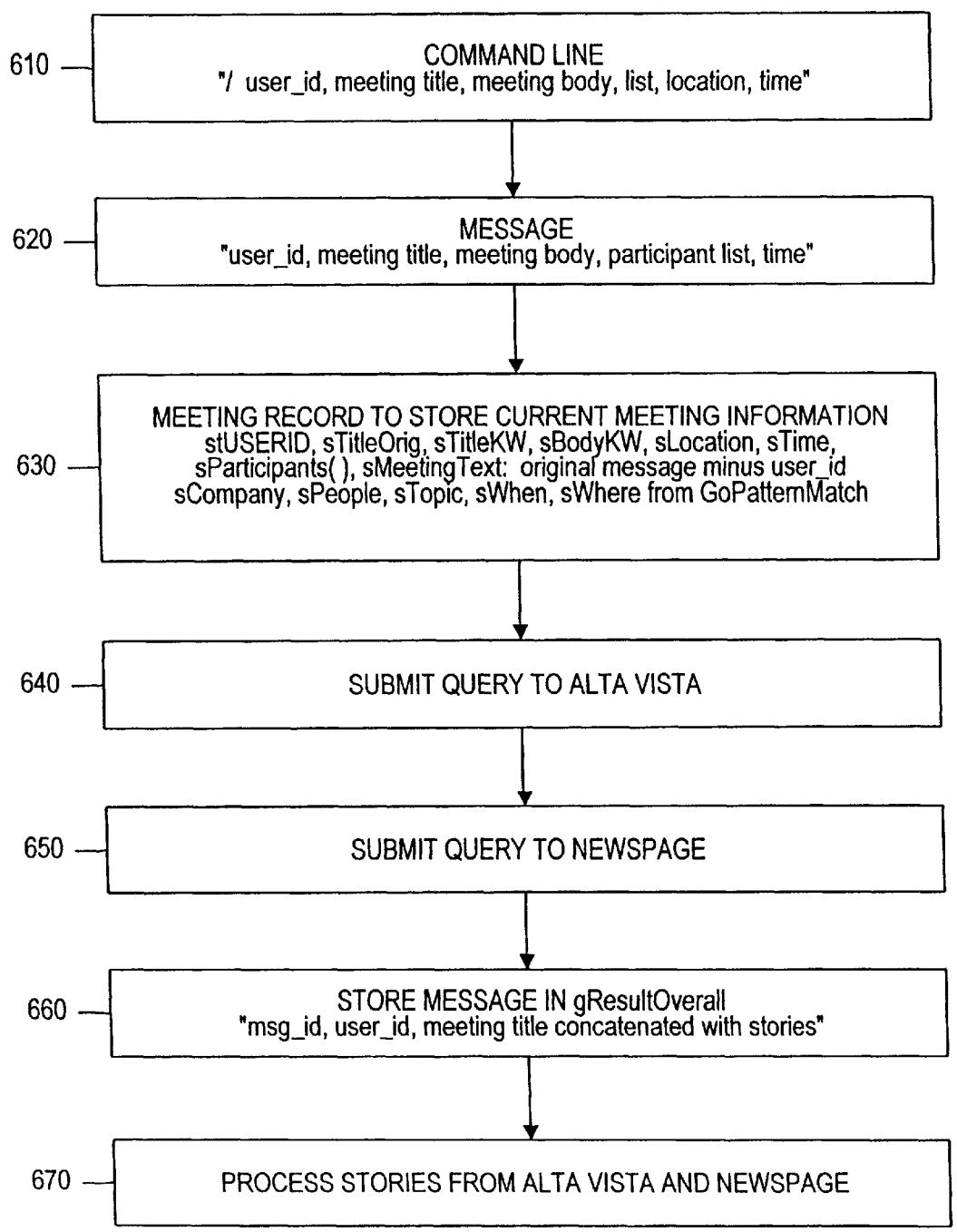
FIG. 6 is a flowchart for overall system processing in accordance with a preferred embodiment.

FIG. 5 is a flowchart of the detailed processing for preparing a query and obtaining information from the Internet in accordance with a preferred embodiment. Processing commences at function block 500 and immediately flows to function block 510 to process the wrapper functionality to prepare for an Internet search utilizing a web search engine. If the search is to utilize the Alta Vista search engine, then at function block 530, the system takes information from the meeting record and forms a query in function blocks 540 to 560 for submittal to the search engine. If the search is to utilize the NewsPage search engine, then at function block 520, the system takes information from the meeting record and forms a query in function blocks 521 to 528.

Alta Vista Search Engine

The strength of the Alta Vista search engine is that it provides enhanced flexibility. Using its advance query method, one can construct all sorts of Boolean queries and rank the search however you want. However, one of the biggest drawbacks with Alta Vista is that it is not very good at handling a large query and is likely to give back irrelevant results. If we can identify the topic and the company within a meeting text, we can form a pretty short but comprehensive query which will hopefully yield better results. We also want to focus on the topics found. It may not be of much merit to the user to find out info about a company especially if the user already knows the company well and has had numerous meetings with them. It's the topics they want to research on.

News Page Search Engine

Figure 7:
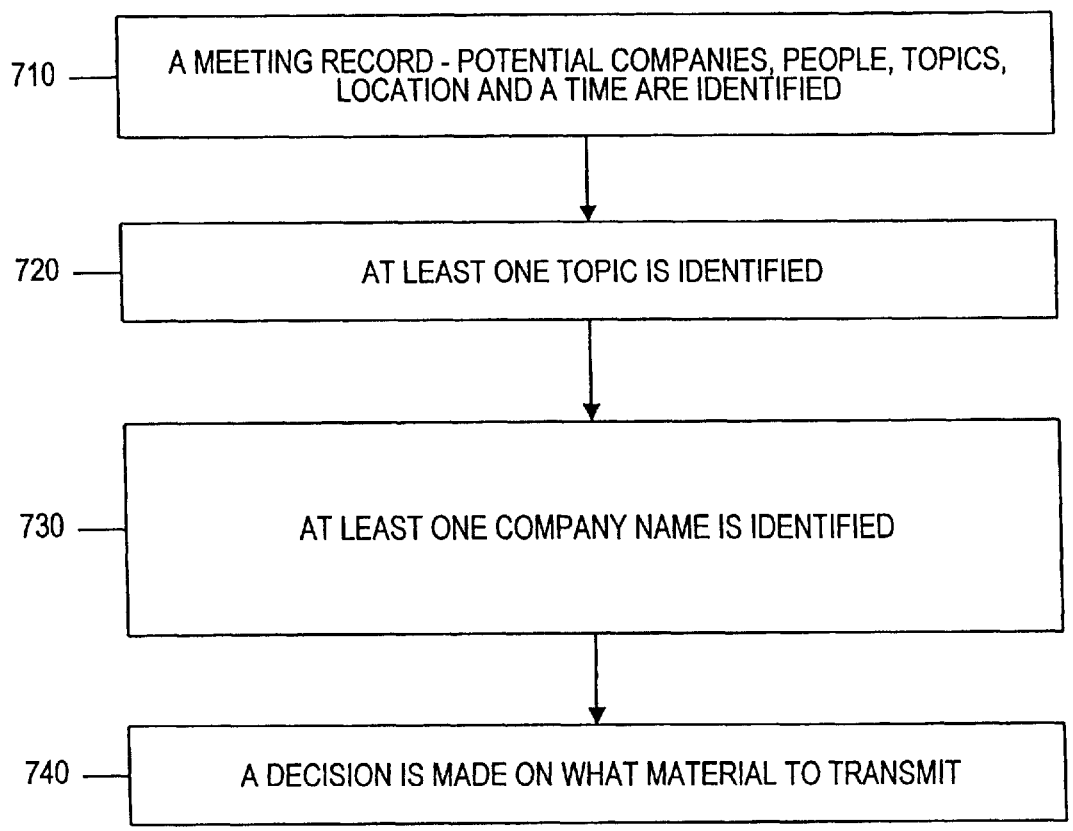
FIG. 7 is a flowchart of topic processing in accordance with a preferred embodiment.
Figure 8:
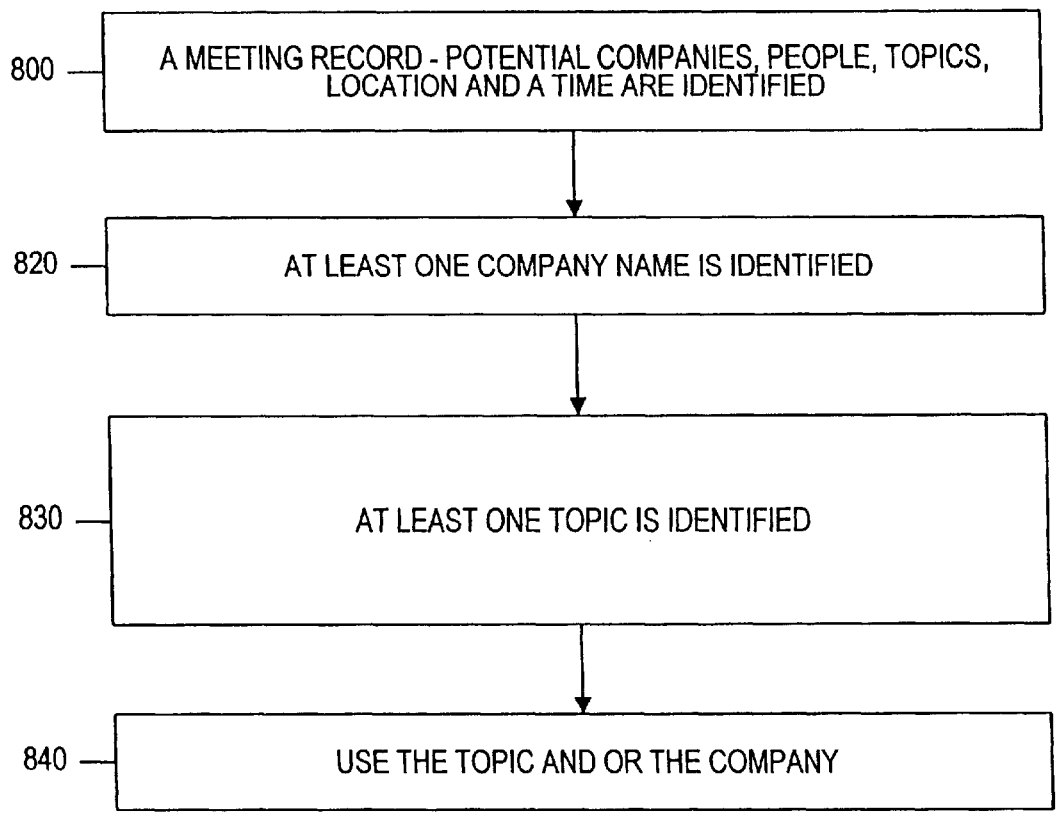
FIG. 8 is a flowchart of meeting record processing in accordance with a preferred embodiment.

The strength of the News Page search engine is that it does a great job searching for the most recent news if you are able to give it a valid company name. Therefore when we submit a query to the news page web site, we send whatever company name we can identify and only if we cannot find one do we use the topics found to form a query. If neither one is found, then no search is performed. The algorithmn utilized to form the query to submit to Alta Vista is illustrated in FIG. 7. The algorithmn that we will use to form the query to submit to News Page is illustrated in FIG. 8.

The following table describes in detail each function in accordance with a preferred embodiment. The order in which functions appear mimics the process flow as closely as possible. When there are situations in which a function is called several times, this function will be listed after the first function which calls it and its description is not duplicated after every subsequent function which calls it.

| Procedure Name | Type | Called By | Description |
| --- | --- | --- | --- |
| Main (BF.Main) | Public Sub | None | This is the main function where the program first launches. It initializes BF with the appropriate parameters (e.g., Internet time-out, stoplist . . . ) and calls GoBF to launch the main part of the program. |
| ProcessCommandLine (BF.Main) | Private Sub | Main | This function parses the command line. It assumes that the delimiter indicating the beginning of input from Munin is stored in the constant CMD_SEPARATOR. |
| CreateStopList (BF.Main) | Private Function | Main | This function sets up a stop list for future use to parse out unwanted words from the meeting text. There are commas on each side of each word to enable straight checking. |
| CreatePatterns (BF.Pattern Match) | Public Sub | Main | This procedure is called once when BF is first initialized to create all the potential patterns that portions of the meeting text can bind to. A pattern can contain however many elements as needed. There are two types of elements. The first type of elements are indicators. These are real words which delimit the potential of a meeting field (e.g. company) to follow. Most of these indicators are stop words as expected because stop words are words usually common to all meeting text so it makes sense they form patterns. The second type of elements are special strings which represent placeholders. |

-continued

| Procedure Name | Type | Called By | Description |
|---|---|---|---|
| | | | A placeholder is always in the form of $*$ where * can be either PEOPLE, COMPANY, TOPIC_UPPER, TIME, LOCATION or TOPIC_ALL. A pattern can begin with either one of the two types of elements and can be however long, involving however any number/type of elements. This procedure dynamically creates a new pattern record for each pattern in the table and it also dynamically creates new tAPatternElements for each element within a pattern. In addition, there is the concept of being able to substitute indicators within a pattern. For example, the pattern $PEOPLE$ of $COMPANY$ is similar to the pattern $PEOPLE$ from $COMPANY$. "from" is a substitute for "of". Our structure should be able to express such a need for substitution. |
| GoBF (BF.Main) | Public Sub | Main | This is a wrapper procedurer that calls both the parsing and the searching subroutines of the BF. It is also responsible for sending data back to Munin. |
| ParseMeetingText (BF.Parse) | Public Function | GoBackGroundFinder | This function takes the initial meeting text and identifies the userID of the record as well as other parts of the meeting text including the title, body, participant list, location and time. In addition, we call a helper function ProcessStopList to eliminate all the unwanted words from the original meeting title and meeting body so that only keywords are left. The information parsed out is stored in the MeetingRecord structure. Note that this function does no error checking and for the most time assumes that the meeting text string is correctly formatted by Munin. The important variable is this Meeting Record is the temp holder for all info regarding current meeting. It's eventually returned to caller. |
| FormatDelimitation (BF.Parse) | Private | ParseMeetingText, DetermineNumWords, GetAWordFromString | There are 4 ways in which the delimiters can be placed. We take care of all these cases by reducing them down to Case 4 in which there are no delimiters around but only between fields in a string (e.g., A::B::C) |

-continued

| Procedure Name | Type | Called By | Description |
|---|---|---|---|
| DetermineNumWords (BF.Parse) | Public Function | ParseMeeting Text, ProcessStop List | This functions determines how many words there are in a string (stInEvalString) The function assumes that each word is separated by a designated separator as specified in stSeparator. The return type is an integer that indicates how many words have been found assuming each word in the string is separated by stSeparator. This function is always used along with GetAwordFromString and should be called before calling GetAWordFrom String. |
| GetAWordFromString (BF.Parse) | Public Function | ParseMeeting Text, ProcessStop List | This function extracts the ith word of the string(stInEvalString) assuming that each word in the string is separated by a designated separator contained in the variable stSeparator. In most cases, use this function with DetermineNumWords. The function returns the wanted word. This function checks to make sure that iInWordNum is within bounds so that i is not greater than the total number of words in string or less than/equal to zero. If it is out of bounds, we return empty string to indicate we can't get anything. We try to make sure this doesn't happen by calling DetermineNumWords first. |
| ParseAndCleanPhrase (BF.Parse) | Private Function | ParseMeetingText | This function first grabs the word and send it to CleanWord in order strip the stuff that nobody wants. There are things in parseWord that will kill the word, so we will need a method of looping through the body and rejecting words without killing the whole function i guess keep CleanWord and check a return value ok, now I have a word so I need to send it down the parse chain. This chain goes ParseCleanPhrase —> CleanWord —> EvaluateWord. If the word gets through the entire chain without being killed, it will be added at the end to our keyword string. first would be the function that checks for "/" as a delimiter and extracts the parts of that. This I will call "StitchFace" (Denise is more normal and calls it GetAWordFromString) if this finds words, then each of these will be sent, in turn, down the chain. If |

-continued

| Procedure Name | Type | Called By | Description |
|---|---|---|---|
| | | | these get through the entire chain without being added or killed then they will be added rather than tossed. |
| FindMin (BF.Parse) | Private Function | ParseAndCleanPhrase | This function takes in 6 input values and evaluates to see what the minimum non zero value is. It first creates an array as a holder so that we can sort the five input values in ascending order. Thus the minimum value will be the first non zero value element of the array. If we go through entire array without finding a non zero value, we know that there is an error and we exit the function. |
| CleanWord (BF.Parse) | Private Function | ParseAndCleanPhrase | This function tries to clean up a word in a meeting text. It first of all determines if the string is of a valid length. It then passes it through a series of tests to see it is clean and when needed, it will edit the word and strip unnecessary characters off of it. Such tests includes getting rid of file extensions, non chars, numbers etc. |
| EvaluateWord (BF.Parse) | Private Function | ParseAndCleanPhrase | This function tests to see if this word is in the stop list so it can determine whether to eliminate the word from the original meeting text. If a word is not in the stoplist, it should stay around as a keyword and this function exits beautifully with no errors. However, if the words is a stopword, an error must be returned. We must properly delimit the input test string so we don't accidentally retrieve sub strings. |
| GoPatternMatch (BF.Pattern Match) | Public Sub | GoBF | This procedure is called when our QueryMethod is set to complex query meaning we do want to do all the pattern matching stuff. It's a simple wrapper function which initializes some arrays and then invokes pattern matching on the title and the body. |
| MatchPatterns (BF.Pattern Match) | Public Sub | GoPattern Match | This procedure loops through every pattern in the pattern table and tries to identify different fields within a meeting text specified by sInEvalString. For debugging purposes it also tries to tabulate how many times a certain pattern was triggered and stores it in gTabulateMatches to see which pattern fired the most. gTabulateMatches is stored as a global because we want to be able to run a batch file of 40 or 50 test strings and still be able to know how often a pattern was triggered. |

-continued

| Procedure Name | Type | Called By | Description |
|---|---|---|---|
| MatchAPattern (BF.Pattern Match) | Private Function | MatchPatterns | This function goes through each element in the current pattern. It first evaluates to determine whether element is a placeholder or an indicator. If it is a placeholder, then it will try to bind the placeholder with some value. If it is an indicator, then we try to locate it. There is a trick however. Depending on whether we are at current element is the head of the pattern or not we want to take different actions. If we are at the head, we want to look for the indicator or the placeholder. If we can't find it, then we know that the current pattern doesn't exist and we quit. However, if it is not the head, then we continue looking, because there may still be a head somewhere. We retry in this case. |
| etingField (BF.Pattern Match) | Private Function | MatchAPattern | This function uses a big switch statement to first determine what kind of placeholder we are talking about and depending on what type of placeholder, we have specific requirements and different binding criteria as specified in the subsequent functions called such as BindNames, BindTime etc. If binding is successful we add it to our guessing record. |
| BindNames (BF.Pattern Match) | Private Function | MatchMeetingField | In this function, we try to match names to the corresponding placeholder $PEOPLE$. Names are defined as any consecutive two words which are capitalized. We also what to retrieve a series of names which are connected by and, or & so we look until we don't see any of these 3 separators anymore. Note that we don't want to bind single word names because it is probably too general anyway so we don't want to produce broad but irrelevant results. This function calls BindAFullName which binds one name so in a since BindNames collects all the results from BindAFullName |
| BindAFullName (BF.Pattern Match) | Private Function | BindNames | This function tries to bind a full name. If the $PEOPLF$ placeholder is not the head of the pattern, we know that it has to come right at the beginning of the test string because we've been deleting stuff off the head of the string all along. If it is the head, we search until we find something that |

-continued

| Procedure Name | Type | Called By | Description |
|---|---|---|---|
| | | | looks like a full name. If we can't find it, then there's no such pattern in the text entirely and we quit entirely from this pattern. This should eventually return us to the next pattern in MatchPatterns. |
| GetNextWord AfterWhite Space (BF.Pattern Match) | Private Function | BindAFull Name, BindTime, BindCompanyTo picLoc | This function grabs the next word in a test string. It looks for the next word after white spaces, @ or /. The word is defined to end when we encounter another one of these white spaces or separators. |
| BindTime (BF.Pattern Match) | Private Function | MatchMeetingField | Get the immediate next word and see if it looks like a time pattern. If so we've found a time and so we want to add it to the record. We probably should add more time patterns. But people don't seem to like to enter the time in their titles these days especially since we now have tools like OutLook. |
| BindCompanyTopicLoc (BF.Pattern Match) | Private Function | MatchMeetingField | This function finds a continuous capitalized string and binds it to stMatch which is passed by reference from MatchMeetingField. A continous capitalized string is a sequence of capitalized words which are not interrupted by things like, . etc. There's probably more stuff we can add to the list of interruptions. |
| LocatePatternHead (BF.Pattern Match) | Private Function | MatchAPattern | This function tries to locate an element which is an indicator. Note that this indicator SHOULD BE AT THE HEAD of the pattern otherwise it would have gone to the function LocateIndicator instead. Therefore, we keep on grabbing the next word until either there's no word for us to grab (quit) or if we find one of the indicators we are looking for. |
| ContainInArray (BF.Pattern Match) | Private Function | LocatePattern Head, LocateIndicator | ' This function is really simple. It loops through all the elements in the array ' to find a matching string. |
| LocateIndicator (BF.Pattern Match) | Private Function | MatchAPattern | This function tries to locate an element which is an indicator. Note that this indicator is NOT at the head of the pattern otherwise it would have gone to LocatePatternHead instead. Because of this, if our pattern is to be satisfied, the next word we grab HAS to be the indicator or else we would have failed. Thus we only grab one word, test to see if it is a valid indicator and then return result. |
| InitializeGuessesRecord (BF.Pattern Match) | Private Sub | MatchAPattern | This function reinitializes our temporary test structure because we have already |

-continued

| Procedure Name | Type | Called By | Description |
|---|---|---|---|
| AddToMeetingRecord (BF.Pattern Match) | Private Sub | MatchAPattern | transfered the info to the permanent structure, we can reinitialize it so they each have one element This function is only called when we know that the information stored in tInCurrGuesses is valid meaning that it represents legitamate guesses of meeting fields ready to be stored in the permanent record, tInMeetingRecord. We check to make sure that we do not store duplicates and we also what to clean up what we want to store so that there's no clutter such as punctuation, etc. The reason why we don't clean up until now is to save time. We don't waste resources calling ParseAndCleanPhrase until we know for sure that we are going to add it permanently. |
| NoDuplicate Entry (BF.Pattern Match) | Private Function | AddToMeeting Record | This function loops through each element in the array to make sure that the test string aString is not the same as any of the strings already stored in the array. Slightly different from ContainInArray. |
| SearchAltaVista (BF. Search) | Public Function | GoBackGroundFinder | This function prepares a query to be submited to AltaVista Search engine. It submits it and then parses the returning result in the appropriate format containing the title, URL and body/summary of each story retrieved. The number of stories retrieved is specified by the constant NUM_AV_STORIES. Important variables include stURLAltaVista used to store query to submit stResultHTML used to store html from page specified by stURLAltaVista. |
| ConstructAltaVistaURL (BF.Search) | Private Function | SearchAltaVista | This function constructs the URL string for the alta vista search engine using the advanced query search mode. It includes the keywords to be used, the language and how we want to rank the search. Depending on whether we want to use the results of our pattern matching unit, we construct our query differently. |
| ConstructSimpleKeyWord (BF.Search) | Private Function | ConstructAltaVistaURL, ConstructNews PageURL | This function marches down the list of keywords stored in the stTitleKW or stBodyKW fields of the input meeting record and links them up into one string with each keyword separated by a connector as determined by the input variable stInConnector. Returns this newly constructed string. |
| ConstructComplexAVKey Word (BF.Search) | Private Function | ConstructAltaVistaURL | This function constructs the keywords to be send to the AltaVista site. Unlike |

-continued

| Procedure Name | Type | Called By | Description |
| --- | --- | --- | --- |
| | | | ConstructSimpleKeyWord which simply takes all the keywords from the title to form the query, this function will look at the results of BF's pattern matching process and see if we are able to identify any specific company names or topics for constructing the queries. Query will include company and topic identified and default to simple query if we cannot identify either company or topic. |
| JoinWithConnectors (BF.Search) | Private Function | ConstructComplexAvKey Word, ConstructComplexNPKey Word, RefineWithRank | This function simply replaces the spaces between the words within the string with a connector which is specified by the input. |
| RefineWithDate (NOT CALLED AT THE MOMENT) (BF.Search) | Private Function | ConstructAltaVistaURL | This function constructs the date portion of the alta vista query and returns this portion of the URL as a string. It makes sure that alta vista searches for articles within the past PAST_NDAYS. |
| RefineWithRank (BF. Search) | Private Function | ConstructAltaVistaURL | This function constructs the string needed to passed to Altavista in order to rank an advanced query search. If we are constructing the simple query we will take in all the keywords from the title. For the complex query, we will take in words from company and topic, much the same way we formed the query in ConstructComplexAVKey Word. |
| IdentifyBlock (BF.Parse) | Public Function | SearchAltaVista, SearchNewsPage | This function extracts the block within a string marked by the beginning and the ending tag given as inputs string at a certain location (iStart). The block retrieved does not include the tags themselves. If the block cannot be identified with the specified delimiters, we return unsuccessful through the parameter iReturnSuccess passed to use by reference. The return type is the block retrieved. |
| IsOpenURLError (BF.Error) | Public Function | SearchAltaVista, SearchNewsPage | This function determines whether the error encountered is that of a timeout error. It restores the mouse to default arrow and then returns true if it is a time out or false otherwise. |
| SearchNews Page (BF.Search) | Public Function | GoBackGroundFinder | This function prepares a query to be submitted to NewsPage Search engine. It submits it and then parses the returning result in the appropriate format containing the title, URL and body/summary of each story retrieved. The number of stories retrieved is specified by the constant UM_NP_STORIES |

-continued

| Procedure Name | Type | Called By | Description |
| --- | --- | --- | --- |
| ConstructNewsPageURL (BF.Search) | Private Function | SearchNewsPage | This function constructs the URL to send to the NewsPage site. It uses the information contained in the input meeting record to determine what keywords to use. Also depending whether we want simple or complex query, we call different functions to form strings. |
| ConstructComplexNPKeyWord (BF.Search) | Private Function | ConstructNewsPageURL | This function constructs the keywords to be send to the NewsPage site. UnlikeConstructKeyWord String which simply takes all the keywords from the title to form the query, this function will look at the results of BF's pattern matching process and see if we are able to identify any specific company names or topics for constructing the queries. Since newspage works best when we have a company name, we'll use only the company name and only if there is no company will we use topic. |
| ConstructOverallResult (BF.Main) | Private Function | GoBackGroundFinder | This function takes in as input an array of strings (stInStories) and a MeetingRecord which stores the information for the current meeting. Each element in the array stores the stories retrieved from each information source. The function simply constructs the appropriate output to send to Munin including a return message type to let Munin know that it is the BF responding and also the original user_id and meeting title so Munin knows which meeting BF is talking about. |
| ConnectAndTransferTo Munin (BF.Main) | Public Sub | GoBackGroundFinder | This function allows Background Finder to connect to Munin and eventually transport information to Munin. We will be using the UDP protocol instead of the TCP protocol so we have to set up the remote host and port correctly. We use a global string to store gResult Overall because although it is unecessary with UDP, it is needed with TCP and if we ever switch back don't want to change code. |
| Disconnect FromMuninAnd Quit (BF.Main) | Public Sub | | |

FIG. 6 is a flowchart of the actual code utilized to prepare and submit searches to the Alta Vista and Newspage search engines in accordance with a preferred embodiment. Processing commences at function block 610 where a command line is utilized to update a calendar entry with specific calendar information. The message is next posted in accordance with function block 620 and a meeting record is created to store the current meeting information in accordance with function block 630. Then, in function block 640 the query is submitted to the Alta Vista search engine and in function block 650, the query is submitted to the Newspage search engine. When a message is returned from the search engine, it is stored in a results data structure as shown in function block 660 and the information is processed and stored in summary form in a file for use in preparation for the meeting as detailed in function block 670.

FIG. 7 provides more detail on creating the query in accordance with a preferred embodiment. Processing commences at function block 710 where the meeting record is parsed to obtain potential companies, people, topics, location and a time. Then, in function block 720, at least one topic is identified and in function block 720, at least one company name is identified and finally in function block 740, a decision is made on what material to transmit to the file for ultimate consumption by the user.

FIG. 8 is a variation on the query theme presented in FIG. 7. A meeting record is parsed in function block 800, a company is identified in function block 820, a topic is identified in function block 830 and finally in function block 840 the topic and or the company is utilized in formulating the query.

Alternative embodiments for adding various specific features for specific user requirements are discussed below.

Enhance Target Rate for Pattern Matching

To increase BF's performance, more patterns/pattern groups are added to the procedure "CreatePatterns." The existing code for declaring patterns can be used as a template for future patterns. Because everything is stored as dynamic arrays, it is convenient to reuse code by cutting and pasting. The functions BindName, BindTime, BindCompanyLocTopic which are responsible for associating a value with a placeholder can be enhanced. The enhancement is realized by increasing the set of criteria for binding a certain meeting field in order to increase the number of binding values. For example, BindTime currently accepts and binds all values in the form of ##:## or #:##. To increase the times we can bind, we may want BindTime to also accept the numbers 1 to 12 followed by the more aesthetic time terminology "o'clock." Vocabulary based recognition algorithms and assigning an accuracy rate to each guess BF makes allowing only guesses which meet a certain threshold to be valid.

Depending on what location the system identifies through pattern matching or alternatively depending on what location the user indicates as the meeting place, a system in accordance with a preferred embodiment suggests a plurality of fine restaurants whenever it detects the words lunch/dinner/breakfast. We can also use a site like company finder to confirm what we got is indeed a company name or if there is no company name that pattern matching can identify, we can use a company finder web site as a "dictionary" for us to determine whether certain capitalized words represent a company name. We can even display stock prices and breaking news for a company that we have identified.

Wireless Bargain Identification in Accordance With A Preferred Embodiment

Figure 9:
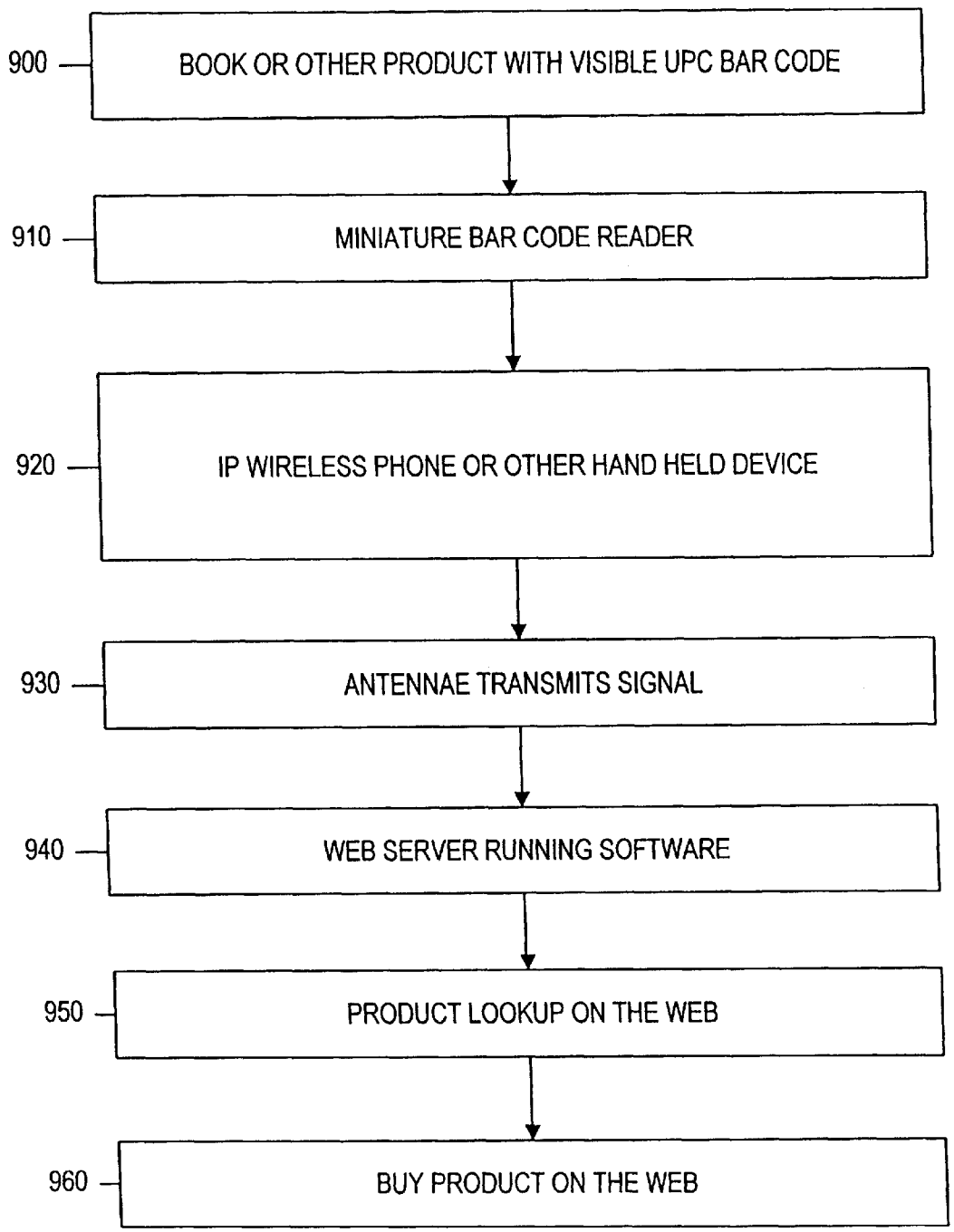
FIG. 9 is a block diagram of process flow of a pocket bargain finder in accordance with a preferred embodiment.

FIG. 9 is a flow diagram that depicts the hardware and logical flow of control for a device and a software system designed to allow Web-based comparison shopping in conventional, physical, non-Web retail environments. A wireless phone or similar hand-held wireless device 920 with Internet Protocol capability is combined with a miniature barcode reader 910 (installed either inside the phone or on a short cable) and used to scan the Universal Product Code (UPC) bar code on a book or other product 900. The wireless device 920 transmits the bar code via an antennae 930 to the Pocket BargainFinder Service Module (running on a Web server) 940, which converts it to (in the case of books) its International Standard Book Number or (in the case of other products) whatever identifier is appropriate. The Service Module then contacts the appropriate third-party Web site(s) to find price, shipping and availability information on the product from various Web suppliers 950. This information is formatted and displayed on the hand-held device's screen. The IP wireless phone or other hand held device 920 utilizes a wireless modem such as a Ricochet SE Wireless Modem from Metricom. Utilizing this device, a user can hang out in a coffee shop with a portable computer perched on a rickety little table, with a latte sloshing dangerously close to the keyboard, and access the Internet at speeds rivaling direct connect via a telephone line.

The 8-ounce Ricochet SE Wireless Modem is about as large as a pack of cigarettes and setup is extremely simple, simply attach the modem to the back of your portable's screen with the included piece of Velcro, plug the cable into the serial port, flip up the stubby antenna, and transmit. Software setup is equally easy: a straightforward installer adds the Ricochet modem drivers and places the connection icon on your desktop. The functional aspects of the modem are identical to that of a traditional telephone modem.

Of course, wireless performance isn't nearly as reliable as a traditional dial-up phone connection. We were able to get strong connections in several San Francisco locations as long as we stayed near the windows. But inside CNET's all-brick headquarters, the Ricochet couldn't connect at all. When you do get online, performance of up to 28.8 kbps is available with graceful degradation to slower speeds. But even the slower speeds didn't disappoint. Compared to the alternative—connecting via a cellular modem—the Ricochet is much faster, more reliable, and less expensive to use. Naturally, the SE Wireless is battery powered. The modem has continuous battery life of up to 12 hours. And in accordance with a preferred embodiment, we ran down our portable computer's dual cells before the Ricochet started to fade.

Thus, utilizing the wireless modem, a user may utilize the web server software 940 to identify the right product 950 and then use an appropriate device's key(s) to select a supplier and place an order in accordance with a preferred embodiment. The BargainFinder Service Module then consummates the order with the appropriate third-party Web supplier 960.

mySite! Personal Web Site & Intentions Value Network Prototype mySite! is a high-impact, Internet-based application in accordance with a preferred embodiment that is focused on the theme of delivering services and providing a personalized experience for each customer via a personal web site in a buyer-centric world. The services are intuitively organized around satisfying customer intentions—fundamental life needs or objectives that require extensive planning decisions, and coordination across several dimensions, such as financial planning, healthcare, personal and professional development, family life, and other concerns. Each member owns and maintains his own profile, enabling him to create and browse content in the system targeted specifically at him. From the time a demand for products or services is entered, to the completion of payment, intelligent agents are utilized to conduct research, execute transactions and provide advice. By using advanced profiling and filtering, the intelligent agents learn about the user, improving the services they deliver. Customer intentions include Managing Daily Logistics (e.g., email, calendar, contacts, to-do list, bill payment, shopping, and travel planning); and Moving to a New Community (e.g., finding a place to live, moving household possessions, getting travel and shipping insurance coverage, notifying business and personal contacts, learning about the new community). From a consumer standpoint, mySite! provides a central location where a user can access relevant products and services and accomplish daily tasks with ultimate ease and convenience.

From a business standpoint, mySite! represents a value-added and innovative way to effectively attract, service, and retain customers. Intention value networks allow a user to enter through a personalized site and, and with the assistance of a learning, intelligent agent, seamlessly interact with network participants. An intention value network in accordance with a preferred embodiment provides superior value. It provides twenty four hour a day, seven days a week access to customized information, advice and products. The information is personalized so that each member views content that is highly customized to assure relevance to the required target user.

Egocentric Interface

An Egocentric Interface is a user interface crafted to satisfy a particular user's needs, preferences and current context. It utilizes the user's personal information that is stored in a central profile database to customize the interface. The user can set security permissions on and preferences for interface elements and content. The content integrated into the Egocentric Interface is customized with related information about the user. When displaying content, the Egocentric Interface will include the relationship between that content and the user in a way that demonstrates how the content relates to the user. For instance, when displaying information about an upcoming ski trip the user has signed up for, the interface will include information about events from the user's personal calendar and contact list, such as other people who will be in the area during the ski trip. This serves to put the new piece of information into a context familiar to the individual user.

Figure 10A:
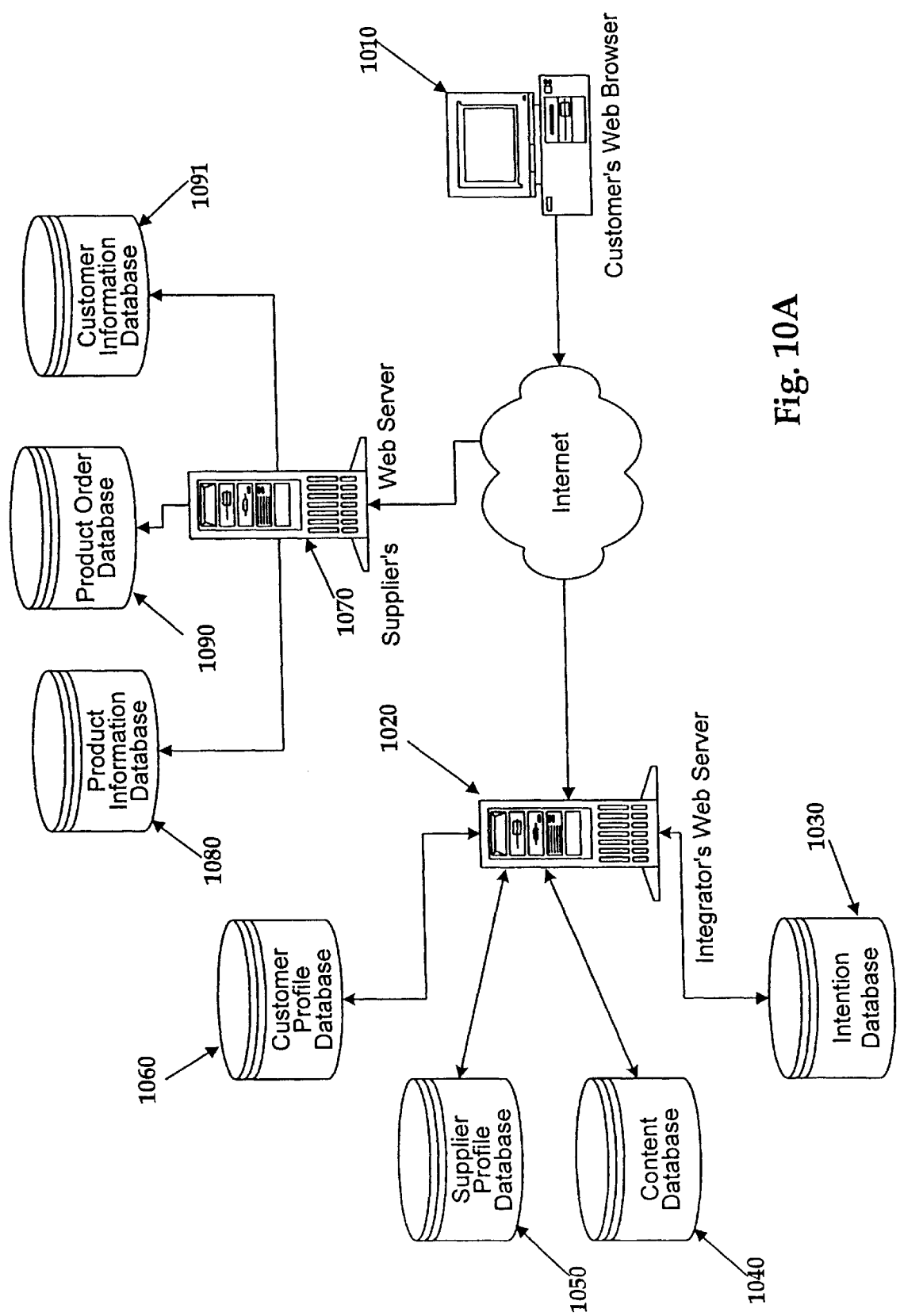
FIGS. 10A and 10B are a block diagram and flowchart depicting the logic associated with creating a customized content web page in accordance with a preferred embodiment.

FIG. 10A describes the Intention Value Network Architecture implementation for the World Wide Web. For simplification purposes, this diagram ignores the complexity pertaining to security, scalability and privacy. The customer can access the Intention Value Network with any Internet web browser 1010, such as Netscape Navigator or Microsoft Internet Explorer, running on a personal computer connected to the Internet or a Personal Digital Assistant with wireless capability. See FIG. 17 for a more detailed description of the multiple methods for accessing an Intention Value Network. The customer accesses the Intention Value Network through the unique name or IP address associated with the Integrator's Web Server 1020. The Integrator creates the Intention Value Network using a combination of resources, such as the Intention Database 1030, the Content Database 1040, the Supplier Profile Database 1050, and the Customer Profile Database 1060.

The Intention Database 1030 stores all of the information about the structure of the intention and the types of products and services needed to fulfill the intention. Information in this database includes intention steps, areas of interest, layout templates and personalization templates. The Content Database 1040 stores all of the information related to the intention, such as advice, referral information, personalized content, satisfaction ratings, product ratings and progress reports.

The Supplier Profile Database 1050 contains information about the product and service providers integrated into the intention. The information contained in this database provides a link between the intention framework and the suppliers. It includes product lists, features and descriptions, and addresses of the suppliers' product web sites. The Customer Profile Database 1060 contains personal information about the customers, such as name, address, social security number and credit card information, personal preferences, behavioral information, history, and web site layout preferences. The Supplier's Web Server 1070 provides access to all of the supplier's databases necessary to provide information and transactional support to the customer.

The Product Information Database 1080 stores all product-related information, such as features, availability and pricing. The Product Order Database 1090 stores all customer orders. The interface to this database may be through an Enterprise Resource Planning application offered by SAP, Baan, Oracle or others, or it may be accessible directly through the Supplier's Web Server or application server. The Customer Information Database 1091 stores all of the customer information that the supplier needs to complete a transaction or maintain customer records.

Figure 10B:
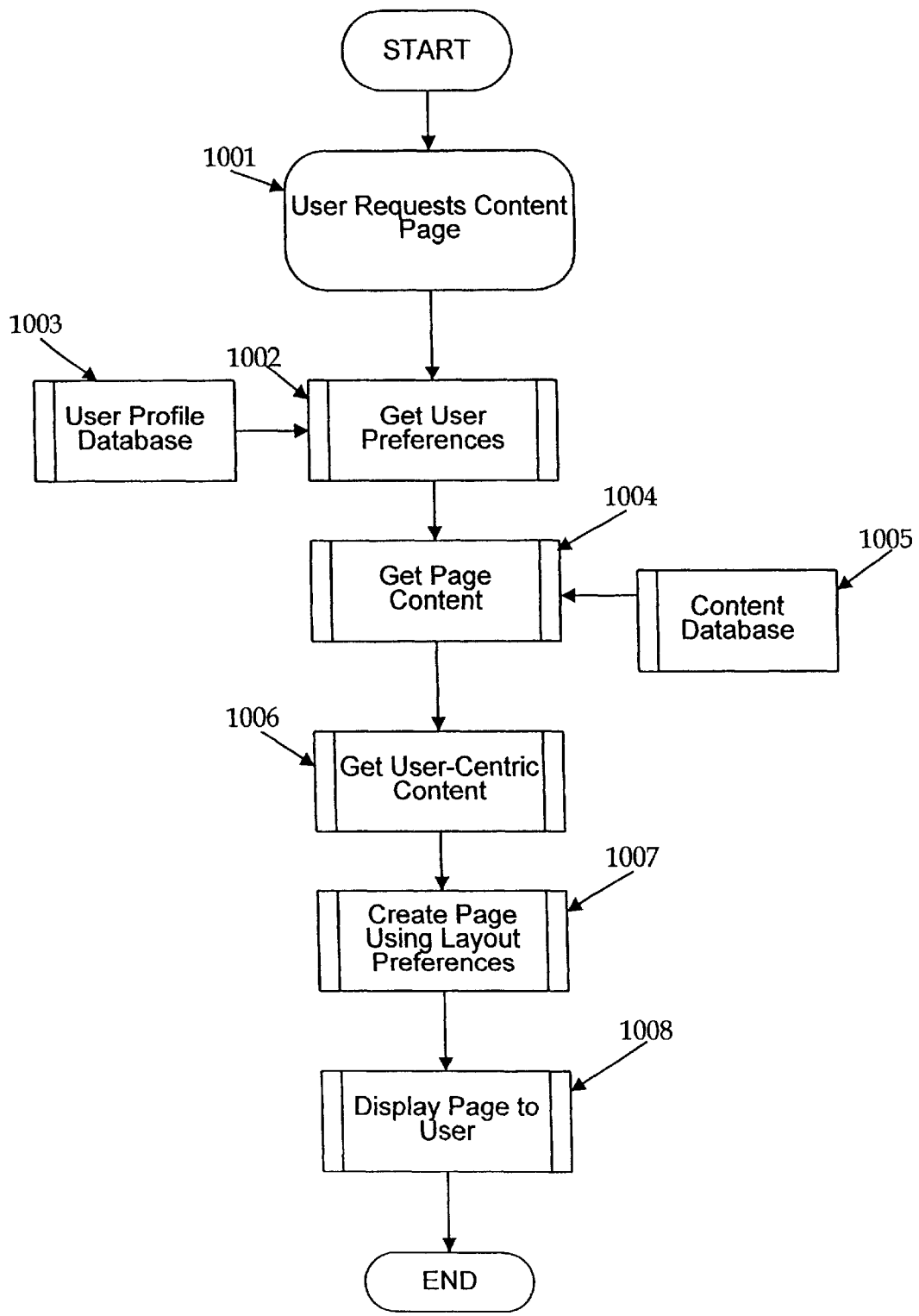

FIG. 10B is a flowchart providing the logic utilized to create a web page within the Egocentric Interface. The environment assumes a web server and a web browser connected through a TCP/IP network, such as over the public Internet or a private Intranet. Possible web servers could include Microsoft Internet Information Server, Netscape Enterprise Server or Apache. Possible web browsers include Microsoft Internet Explorer or Netscape Navigator. The client (i.e. web browser) makes a request 1001 to the server (i.e. web server) for a particular web page. This is usually accomplished by a user clicking on a button or a link within a web page. The web server gets the layout and content preferences 1002 for that particular user, with the request to the database keyed off of a unique user id stored in the client (i.e. web browser) and the User profile database 1003. The web server then retrieves the content 1004 for the page that has been requested from the content database 1005. The relevant user-centric content, such as calendar, email, contact list, and task list items are then retrieved 1006. (See FIG. 11 for a more detailed description of this process.) The query to the database utilizes the user content preferences stored as part of the user profile in the User profile database 1003 to filter the content that is returned. The content that is returned is then formatted into a web page 1007 according to the layout preferences defined in the user profile. The web page is then returned to the client and displayed to the user 1008.

Figure 11:
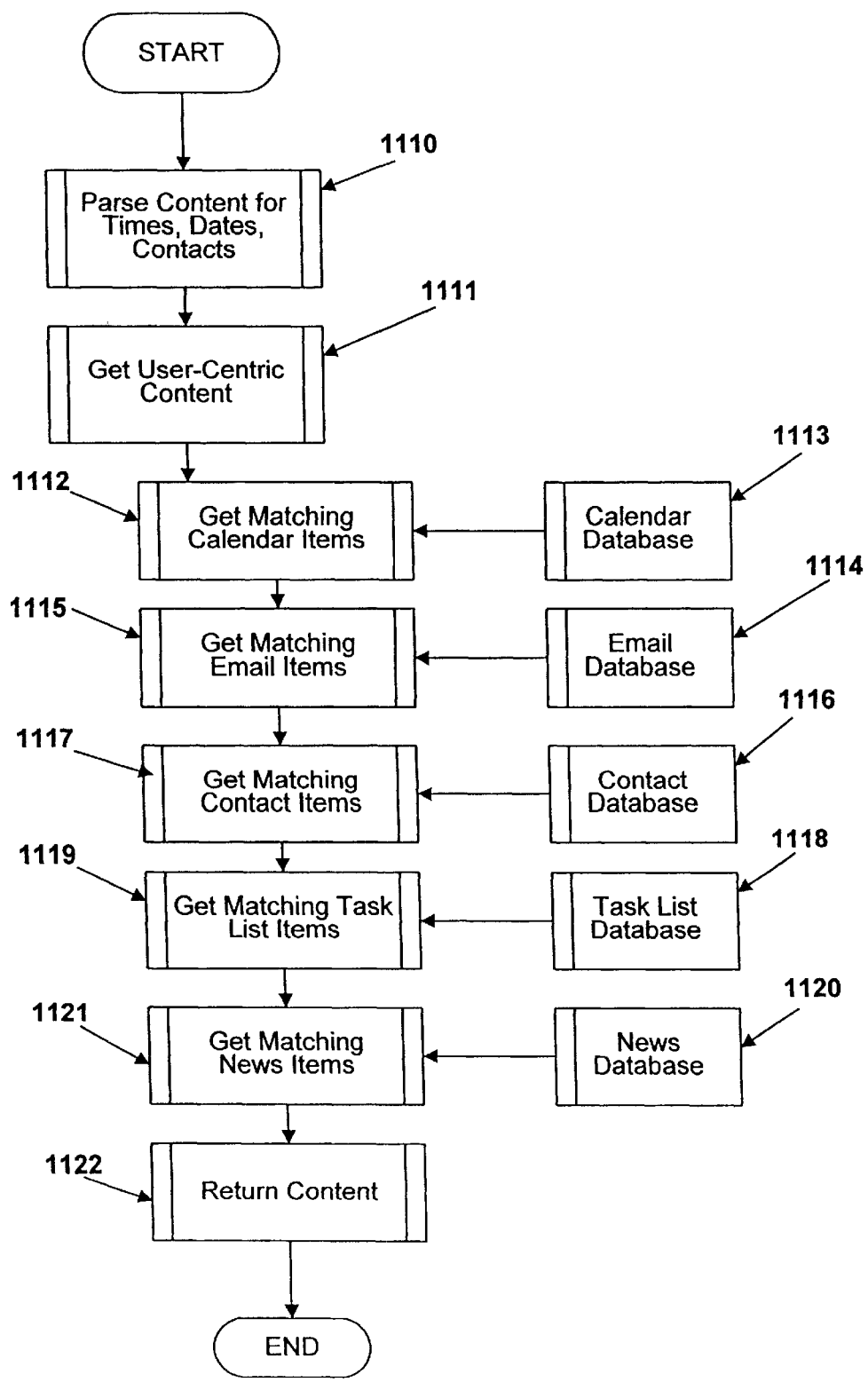
FIG. 11 is a flowchart depicting the detailed logic associated with retrieving user-centric content in accordance with a preferred embodiment.

FIG. 11 describes the process of retrieving user-centric content to add to a web page. This process describes 1006 in FIG. 10B in a more detailed fashion. It assumes that the server already has obtained the user profile and the existing content that is going to be integrated into this page. The server parses 1110 the filtered content, looking for instances of events, contact names and email addresses. If any of these are found, they are tagged and stored in a temporary holding space. Then, the server tries to find any user-centric content 1120 stored in various databases. This involves matching the tagged items in the temporary storage space with calendar items 1130 in the Calendar Database 1140; email items 1115 in the Email Database 1114; contact items 1117 in the Contact Database 1168; task list items 1119 in the Task List Database 1118; and news items 1121 in the News Database 1120. After retrieving any relevant user-centric content, it is compiled together and returned 1122.

User Persona

The system allows the user to create a number of different personas that aggregate profile information into sets that are useful in different contexts. A user may create one persona when making purchases for his home. This persona may contain his home address and may indicate that this user is looking to find a good bargain when shopping. The same user may create a second persona that can be used when he is in a work context. This persona may store the user's work address and may indicate that the user prefers certain vendors or works for a certain company that has a discount program in place. When shopping for work-related items, the user may use this persona. A persona may also contain rules and restrictions. For instance, the work persona may restrict the user to making airline reservations with only one travel agent and utilizing booking rules set up by his employer.

Figure 12:
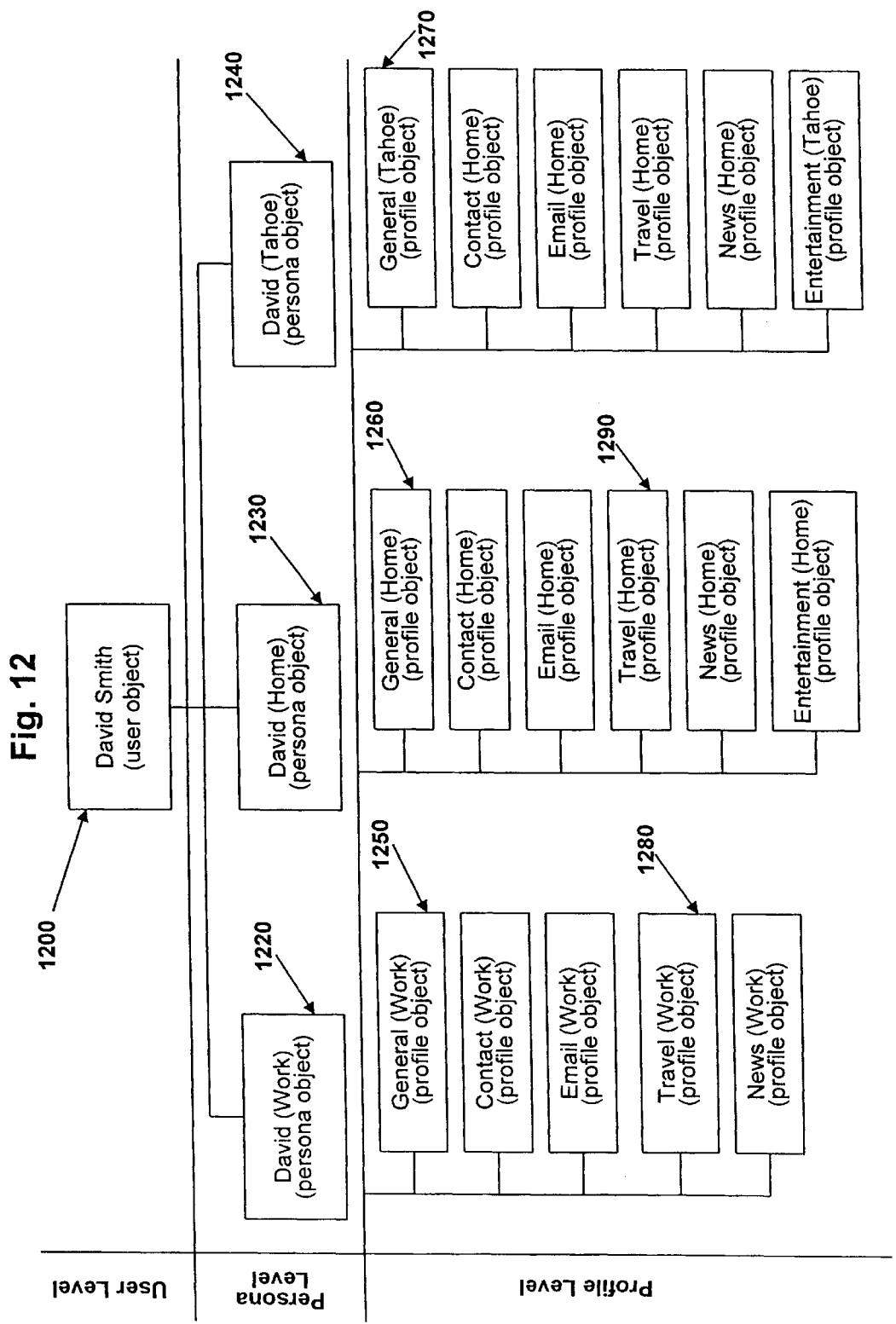
FIG. 12 is a data model of a user profile in accordance with a preferred embodiment.

FIG. 12 describes the relationship between a user, his multiple personas and his multiple profiles. At the User Level is the User Profile 1200. This profile describes the user and his account information. There is one unique record in the database for each user who has an account. Attached to each user are multiple Personas 1220, 1230 & 1240. These Personas are used to group multiple profiles into useful contexts. For instance, consider a user who lives in San Francisco and works in Palo Alto, but has a mountain cabin in Lake Tahoe. He has three different contexts in which he might be accessing his site. One context is work-related. The other two are home-life related, but in different locations. The user can create a Persona for Work 1220, a Persona for Home 1230, and a Persona for his cabin home 1240. Each Persona references a different General Profile 1250, 1260 and 1270 which contains the address for that location. Hence, there are three General Profiles. Each Persona also references one of two Travel Profiles. The user maintains a Work Travel Profile 1280 that contains all of the business rules related to booking tickets and making reservations. This Profile may specify, for instance, that this person only travels in Business or First Class and his preferred airline is United Airlines. The Work Persona references this Work Travel Profile. The user may also maintain a Home Travel Profile 1290 that specifies that he prefers to travel in coach and wants to find non-refundable fairs, since they are generally cheaper. Both the Persona for Home and the Persona for the cabin home point to the Home Travel Profile.

Figure 13:
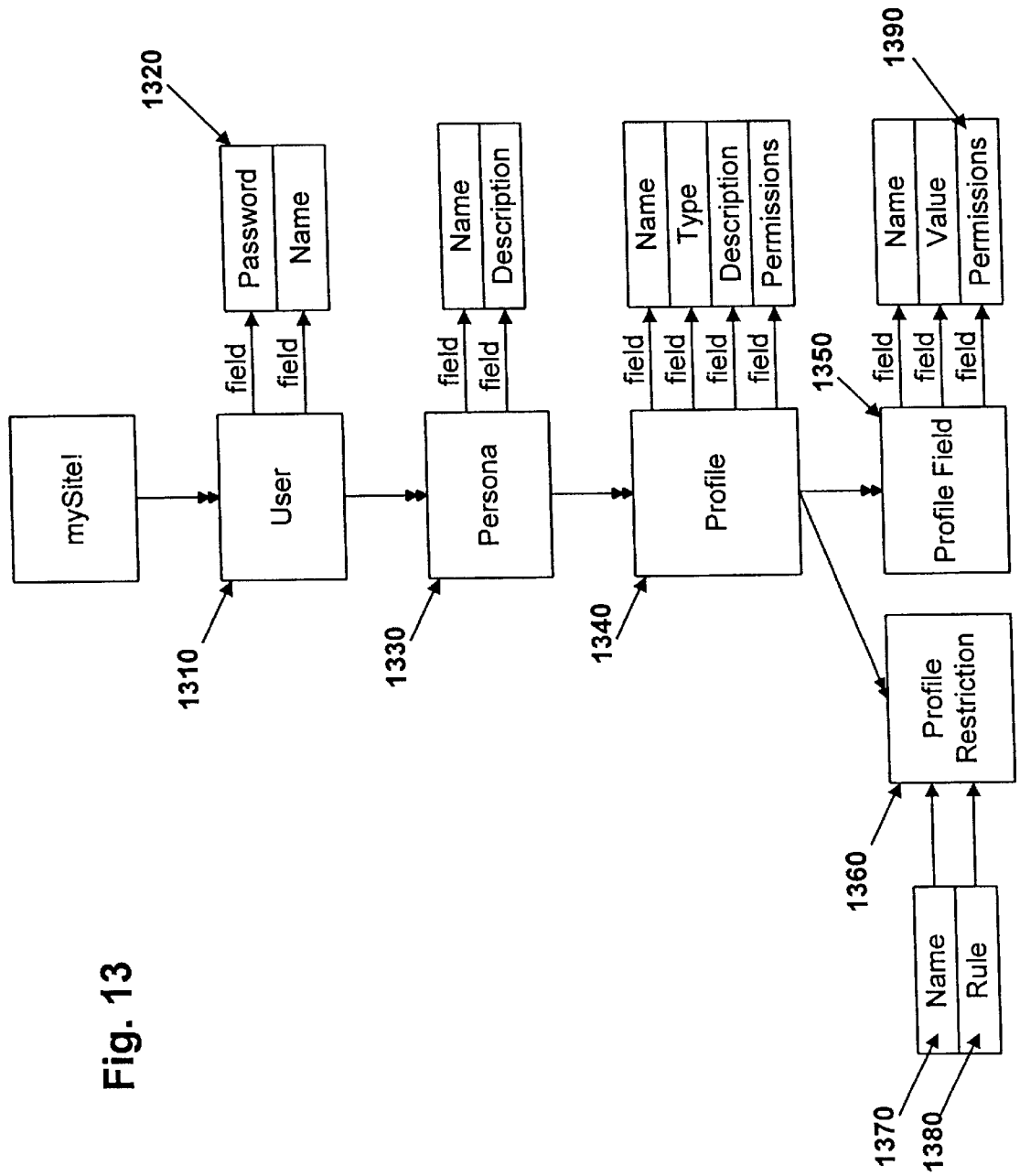
FIG. 13 is a persona data model in accordance with a preferred embodiment.

FIG. 13 describes the data model that supports the Persona concept. The user table 1310 contains a record for each user who has an account in the system. This table contains a username and a password 1320 as well as a unique identifier. Each user can have multiple Personas 1330, which act as containers for more specialized structures called Profiles 1340. Profiles contain the detailed personal information in Profile Field 1350 records. Attached to each Profile are sets of Profile Restriction 1360 records. These each contain a Name 1370 and a Rule 1380, which define the restriction. The Rule is in the form of a pattern like (if x then y), which allows the Rule to be restricted to certain uses. An example Profile Restriction would be the rule that dictates that the user cannot book a flight on a certain airline contained in the list. This Profile Restriction could be contained in the "Travel" Profile of the "Work" Persona set up by the user's employer, for instance. Each Profile Field also contains a set of Permissions 1390 that are contained in that record. These permissions dictate who has what access rights to that particular Profile Field's information.

Intention-Centric Interface

Satisfying Customer Intentions, such as Planning for Retirement or Relocating requires a specialized interface. Customer Intentions require extensive planning and coordination across many areas, ranging from financial security, housing and transportation to healthcare, personal and professional development, and entertainment, among others. Satisfying Intentions requires a network of complementary businesses, working across industries, to help meet consumers' needs.

An Intention-Centric Interface is a user interface designed to help the user manage personal Intentions. At any given point, the interface content is customized to show only content that relates to that particular Intention. The Intention-Centric Interface allows the user to manage the process of satisfying that particular Intention. This involves a series of discrete steps and a set of content areas the user can access. At any point, the user can also switch the interface to manage a different Intention, and this act will change the content of the interface to include only that content which is relevant to the satisfaction of the newly selected Intention.

Figure 14:
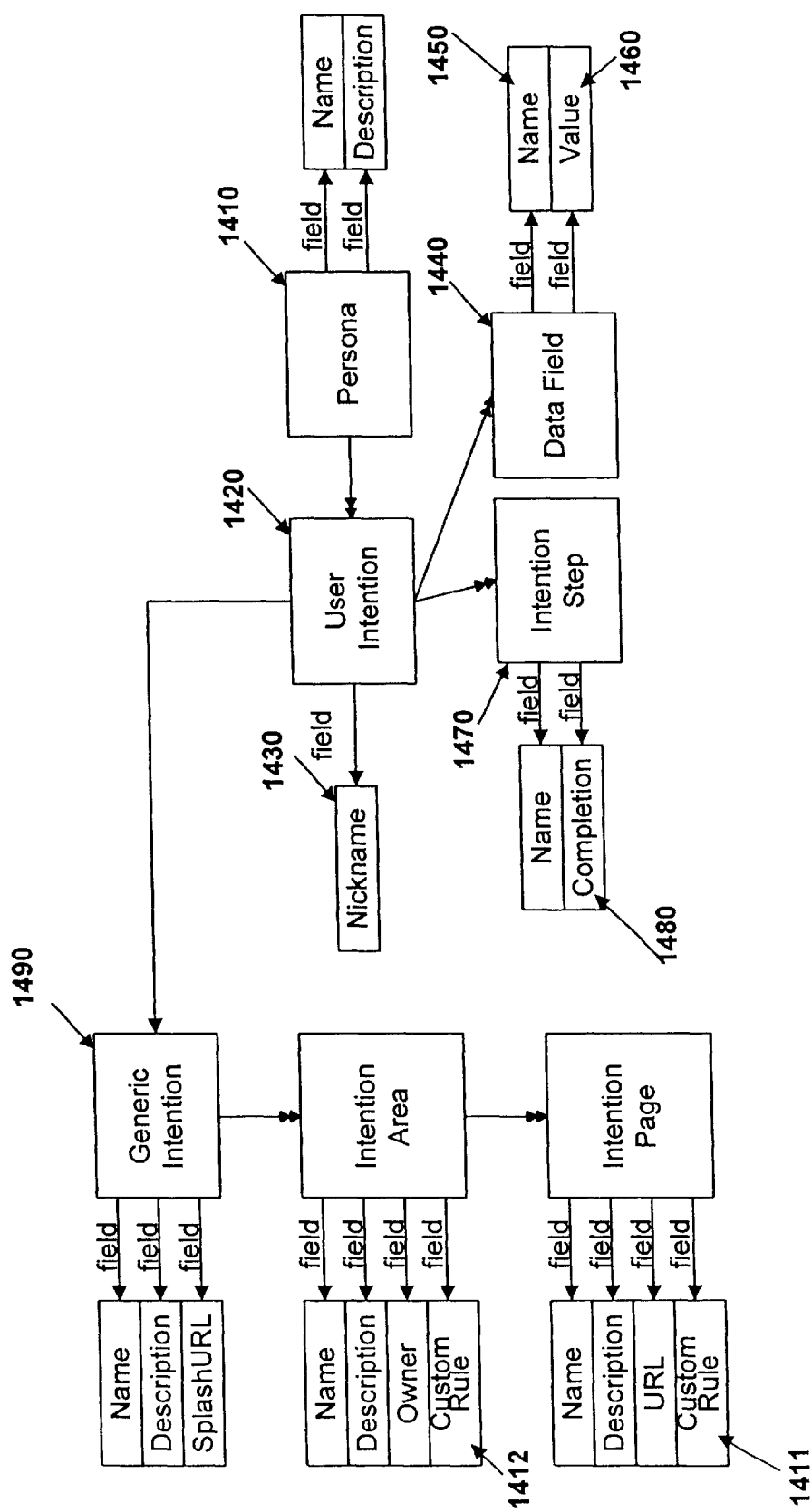
FIG. 14 is an intention data model in accordance with a preferred embodiment.

FIG. 14 provides a detailed description of the data model needed to support an Intention-Centric Interface. Each User Persona 1410 (see FIG. 13 for a more detailed description of the Persona data model.) has any number of active User Intentions 1420. Each active User Intention is given a Nickname 1430, which is the display name the user sees on the screen. Each active User Intention also contains a number of Data Fields 1440, which contain any user data collected throughout the interaction with the user. For instance, if the user had filled out a form on the screen and one of the fields was Social Security Number, the corresponding Data Field would contain Name="SSN" 1450, Value="999-99-9999" 1460. Each User Intention also keeps track of Intention Step 1470 completion status. The Completion 1480 field indicates whether the user has completed the step. Every User Intention is a user-specific version of a Generic Intention 1490, which is the default model for that Intention for all users. The Generic Intention is customized through Custom Rules 1411 and 1412 that are attached to the sub-steps in the Intention. These Custom Rules are patterns describing how the system will customize the Intention for each individual user using the individual user's profile information.

Statistical Agent

An agent keeps track of key statistics for each user. These statistics are used in a manner similar to the Tamagochi virtual reality pet toy to encourage certain behaviors from the user. The statistics that are recorded are frequency of login, frequency of rating of content such as news articles, and activity of agents, measured by the number of tasks which it performs in a certain period. This information is used by the system to emotionally appeal to the user to encourage certain behaviors.

Figure 15:
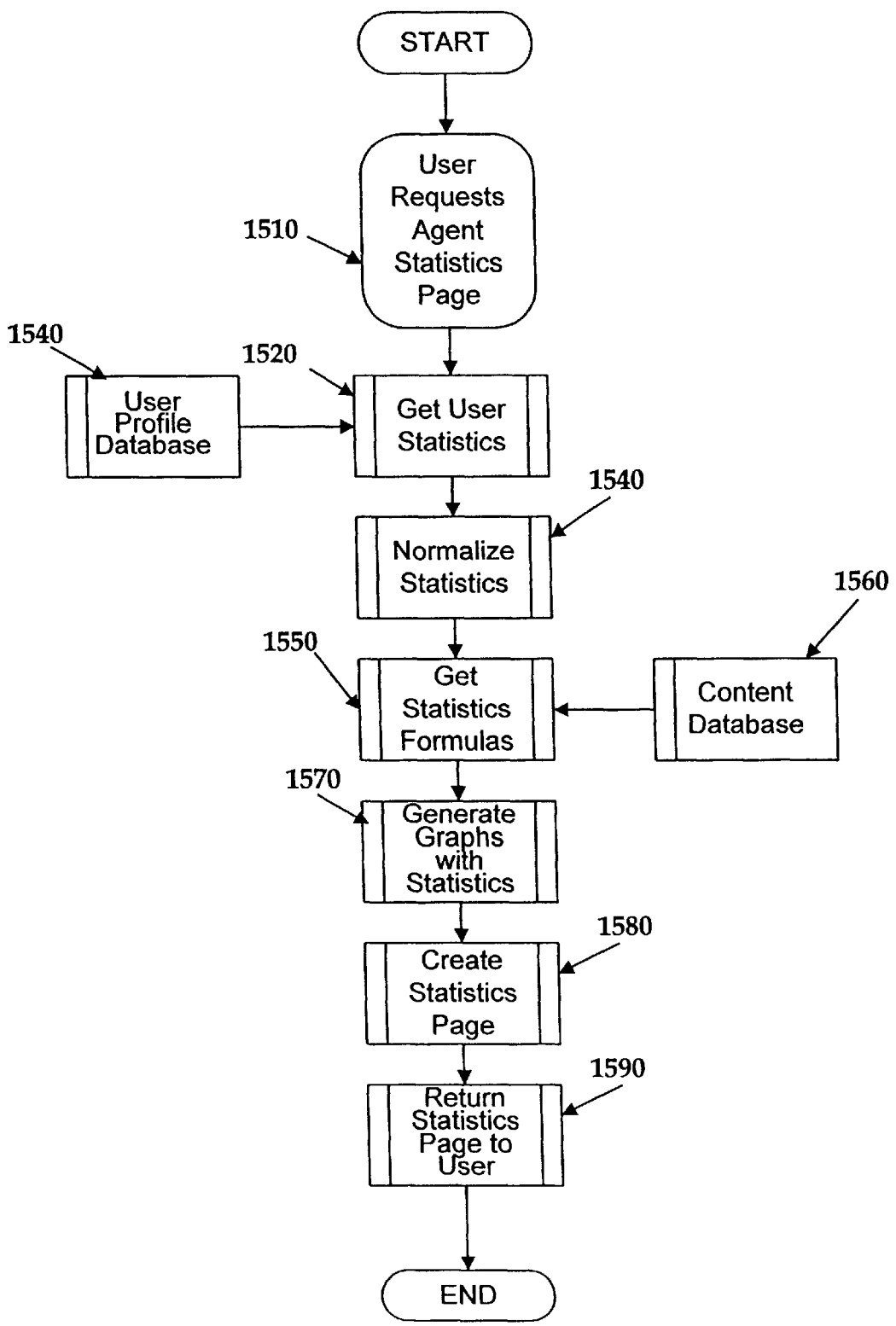
FIG. 15 is a flowchart of the processing for generating an agent's current statistics in accordance with a preferred embodiment.

FIG. 15 describes the process for generating the page that displays the agent's current statistics. When the user requests the agent statistics page 1510 with the client browser, the server retrieves the users' statistics 1520 from the users' profile database 1530. The server then performs the mathematical calculations necessary to create a normalized set of statistics 1540. The server then retrieves the formulas 1550 from the content database 1560 that will be used to calculate the user-centric statistics. Graphs are then generated 1570 using the generic formulas and that user's statistics. These graphs are inserted into a template to create the statistics page 1580. This page is then returned to the user 1590.

Personalized Product Report Service

The system provide Consumer Report-like service that is customized for each user based on a user profile. The system records and provides ratings from users about product quality and desirability on a number of dimensions. The difference between this system and traditional product quality measurement services is that the ratings that come back to the users are personalized. This service works by finding the people who have the closest match to the user's profile and have previously rated the product being asked for. Using this algorithm will help to ensure that the product reports sent back to the user only contain statistics from people who are similar to that user.

Figure 16:
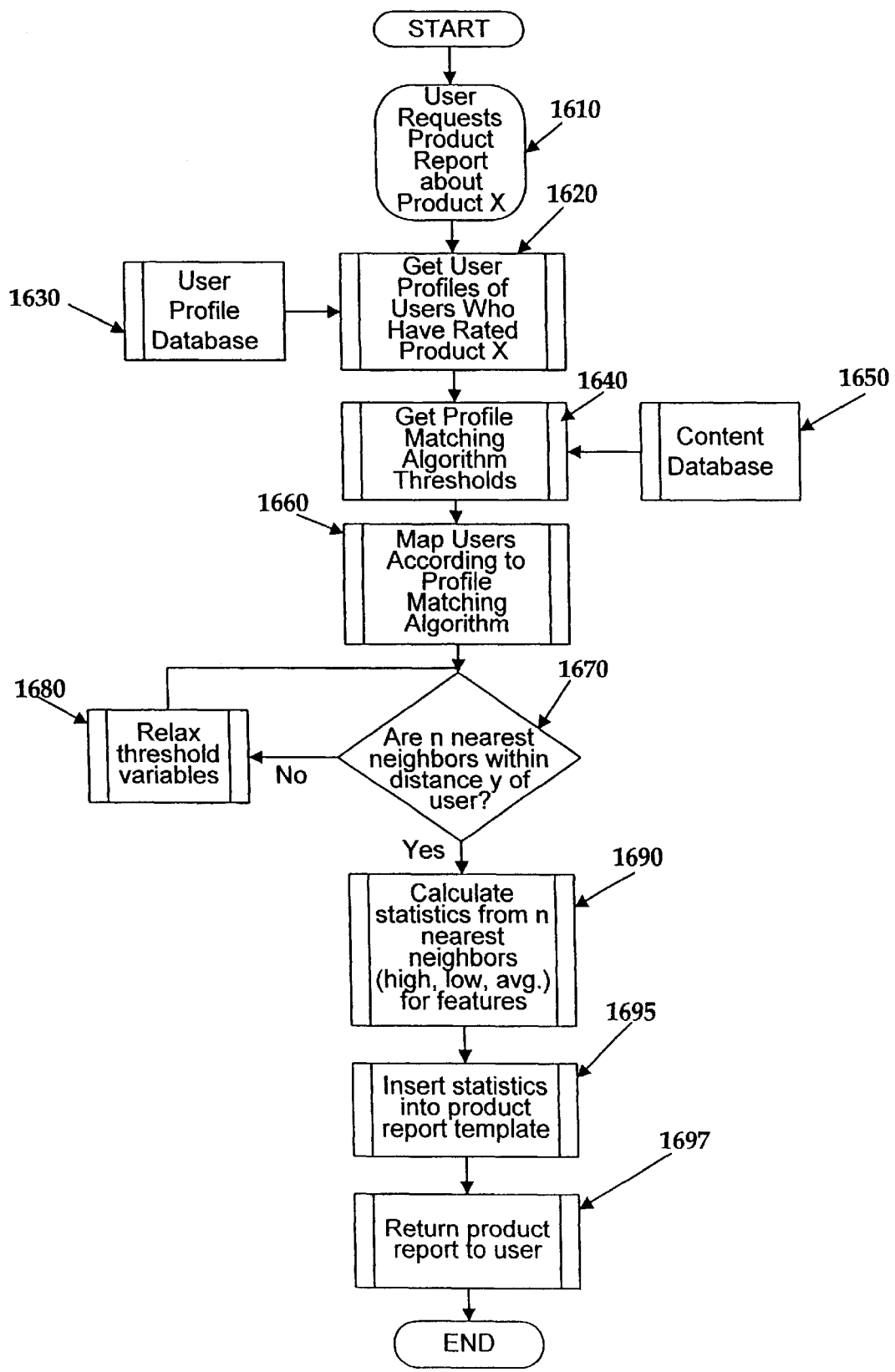
FIG. 16 is a flowchart of the logic that determines the personalized product rating for a user in accordance with a preferred embodiment.

FIG. 16 describes the algorithm for determining the personalized product ratings for a user. When the user requests a product report 1610 for product X, the algorithm retrieves the profiles 1620 from the profile database 1630 (which includes product ratings) of those users who have previously rated that product. Then the system retrieves the default thresholds 1640 for the profile matching algorithm from the content database 1650. It then maps all of the short list of users along several dimensions specified in the profile matching algorithm 1660. The top n (specified previously as a threshold variable) nearest neighbors are then determined and a test is performed to decide if they are within distance y (also specified previously as a threshold variable) of the user's profile in the set 1670 using the results from the profile matching algorithm. If they are not within the threshold, then the threshold variables are relaxed 1680, and the test is run again. This processing is repeated until the test returns true. The product ratings from the smaller set of n nearest neighbors are then used to determine a number of product statistics 1690 along several dimensions. Those statistics are inserted into a product report template 1695 and returned to the user 1697 as a product report.

Personal Profile and Services Ubiquity

This system provides one central storage place for a person's profile. This storage place is a server available through the public Internet, accessible by any device that is connected to the Internet and has appropriate access. Because of the ubiquitous accessibility of the profile, numerous access devices can be used to customize services for the user based on his profile. For example, a merchant's web site can use this profile to provide personalized content to the user. A Personal Digital Assistant (PDA) with Internet access can synchronize the person's calendar, email, contact list, task list and notes on the PDA with the version stored in the Internet site. This enables the person to only have to maintain one version of this data in order to have it available whenever it is needed and in whatever formats it is needed.

Figure 17:
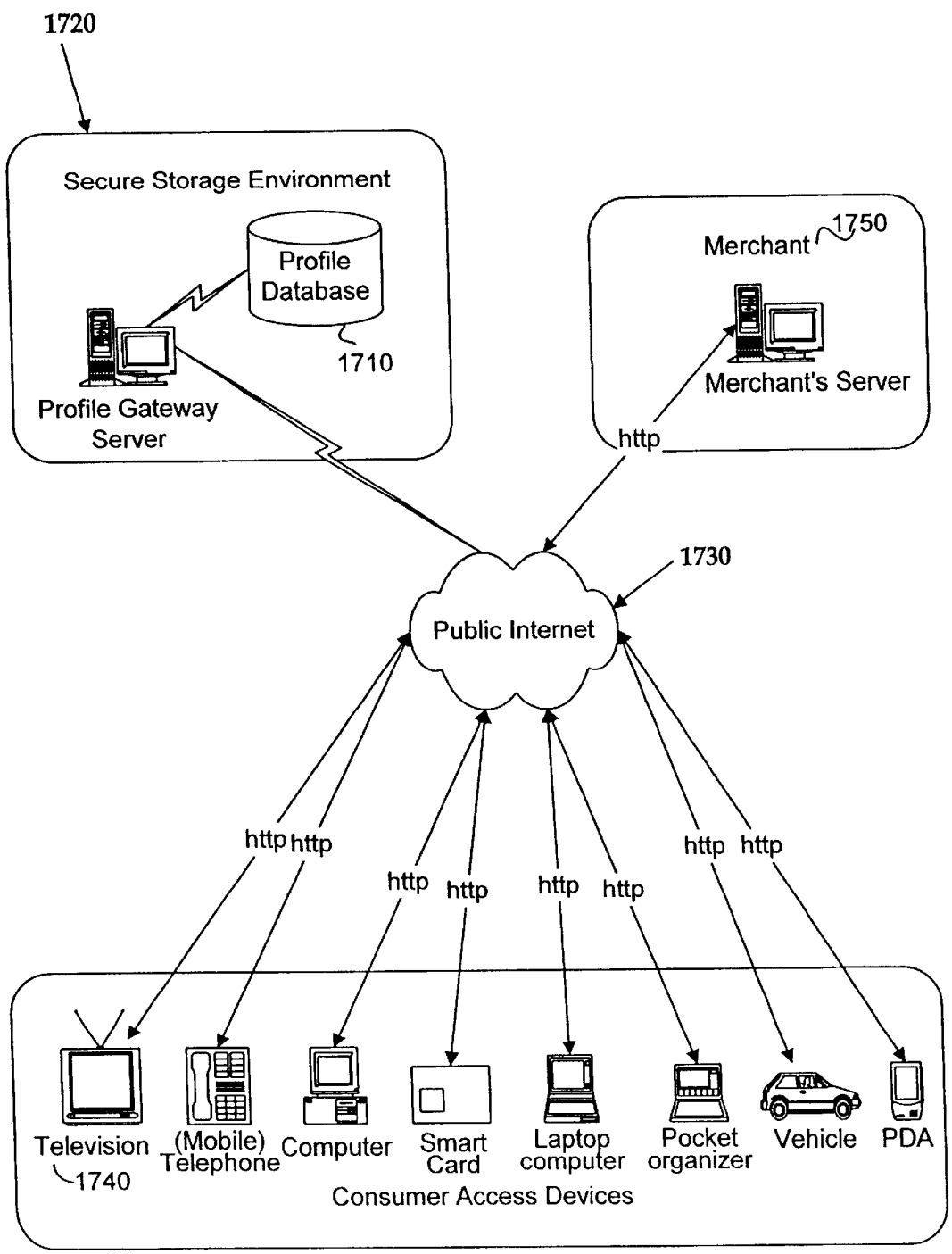
FIG. 17 is a flowchart of the logic for accessing the centrally stored profile in accordance with a preferred embodiment.

FIG. 17 presents the detailed logic associated with the many different methods for accessing this centrally stored profile. The profile database 1710 is the central storage place for the users' profile information. The profile gateway server 1720 receives all requests for profile information, whether from the user himself or merchants trying to provide a service to the user. The profile gateway server is responsible for ensuring that information is only given out when the profile owner specifically grants permission. Any device that can access the public Internet 1730 over TCP/IP (a standard network communications protocol) is able to request information from the profile database via intelligent HTTP requests. Consumers will be able to gain access to services from devices such as their televisions 1740, mobile phones, Smart Cards, gas meters, water meters, kitchen appliances, security systems, desktop computers, laptops, pocket organizers, PDAs, and their vehicles, among others. Likewise, merchants 1750 will be able to access those profiles (given permission from the consumer who owns each profile), and will be able to offer customized, personalized services to consumers because of this.

One possible use of the ubiquitous profile is for a hotel chain. A consumer can carry a Smart Card that holds a digital certificate uniquely identifying him. This Smart Card's digital certificate has been issued by the system and it recorded his profile information into the profile database. The consumer brings this card into a hotel chain and checks in. The hotel employee swipes the Smart Card and the consumer enters his Pin number, unlocking the digital certificate. The certificate is sent to the profile gateway server (using a secure transmission protocol) and is authenticated. The hotel is then given access to a certain part of the consumer's profile that he has previously specified. The hotel can then retrieve all of the consumer's billing information as well as preferences for hotel room, etc. The hotel can also access the consumer's movie and dining preferences and offer customized menus for both of them. The hotel can offer to send an email to the consumer's spouse letting him/her know the person checked into the hotel and is safe. All transaction information can be uploaded to the consumer's profile after the hotel checks him in. This will allow partners of the hotel to utilize the information about the consumer that the hotel has gathered (again, given the consumer's permission).

Intention Value Network

In an Intention Value Network, the overall integrator system coordinates the delivery of products and services for a user. The integrator manages a network of approved suppliers providing products and services, both physical and virtual, to a user based on the user's preferences as reflected in the user's profile. The integrator manages the relationship between suppliers and consumers and coordinates the suppliers' fulfillment of consumers' intentions. It does this by providing the consumer with information about products and suppliers and offering objective advice, among other things.

Figure 18:
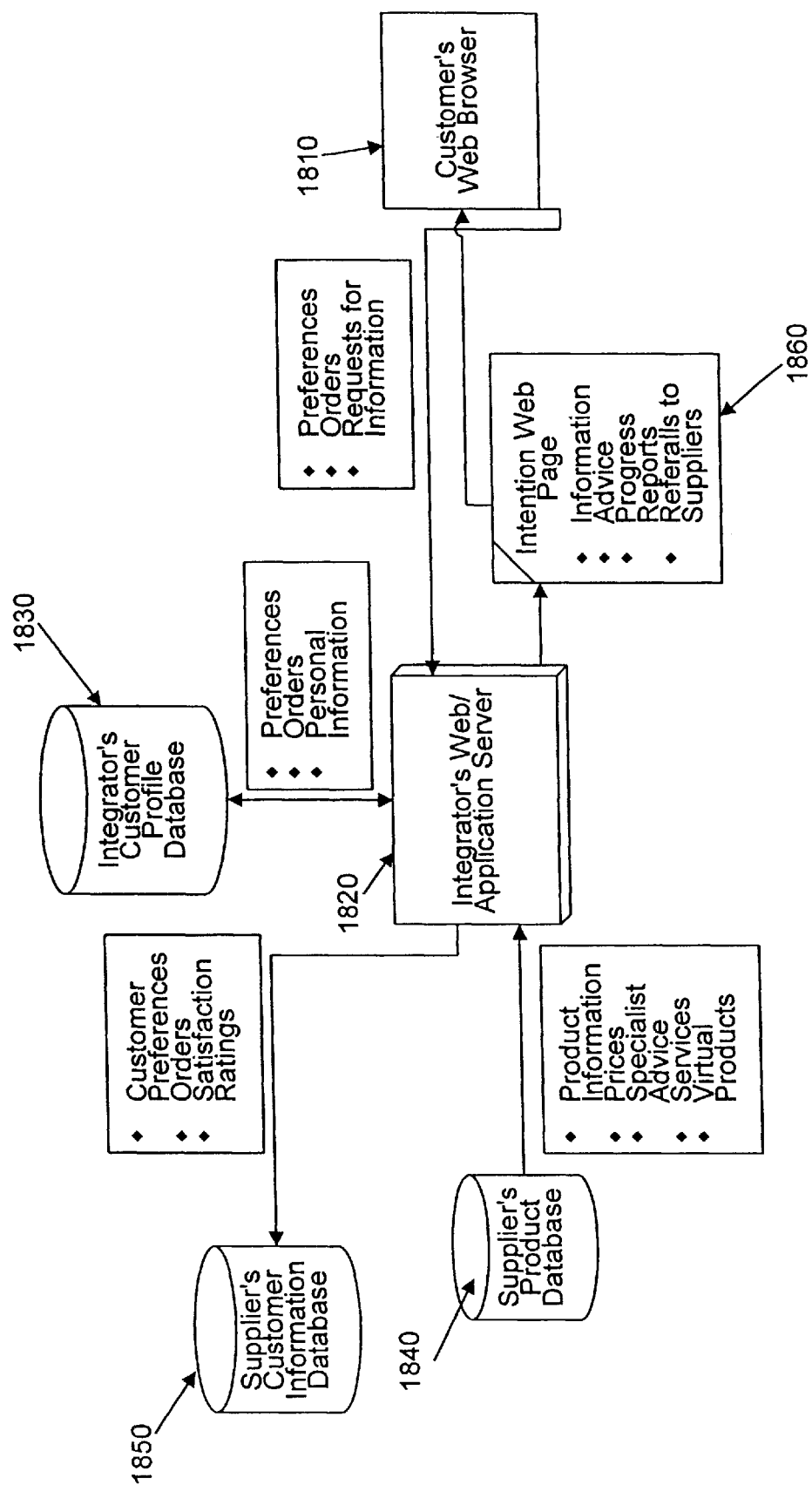
FIG. 18 is a flowchart of the interaction logic between a user and the integrator for a particular supplier in accordance with a preferred embodiment.

FIG. 18 discloses the detailed interaction between a consumer and the integrator involving one supplier. The user accesses a Web Browser 1810 and requests product and pricing information from the integrator. The request is sent from the user's browser to the integrator's Web/Application Server 1820. The user's preferences and personal information is obtained from an integrator's customer profile database 1830 and returned to the Web/Application server. The requested product information is extracted from the supplier's product database 1840 and customized for the particular customer. The Web/Application server updates the supplier's customer information database 1850 with the inquiry information about the customer. The product and pricing information is then formatted into a Web Page 1860 and returned to the customer's Web Browser.

Summary Agent

A suite of software agents running on the application and web servers are programmed to take care of repetitive or mundane tasks for the user. The agents work according to rules set up by the user and are only allowed to perform tasks explicitly defined by the user. The agents can take care of paying bills for the user, filtering content and emails, and providing a summary view of tasks and agent activity. The user interface for the agent can be modified to suit the particular user.

Figure 19:
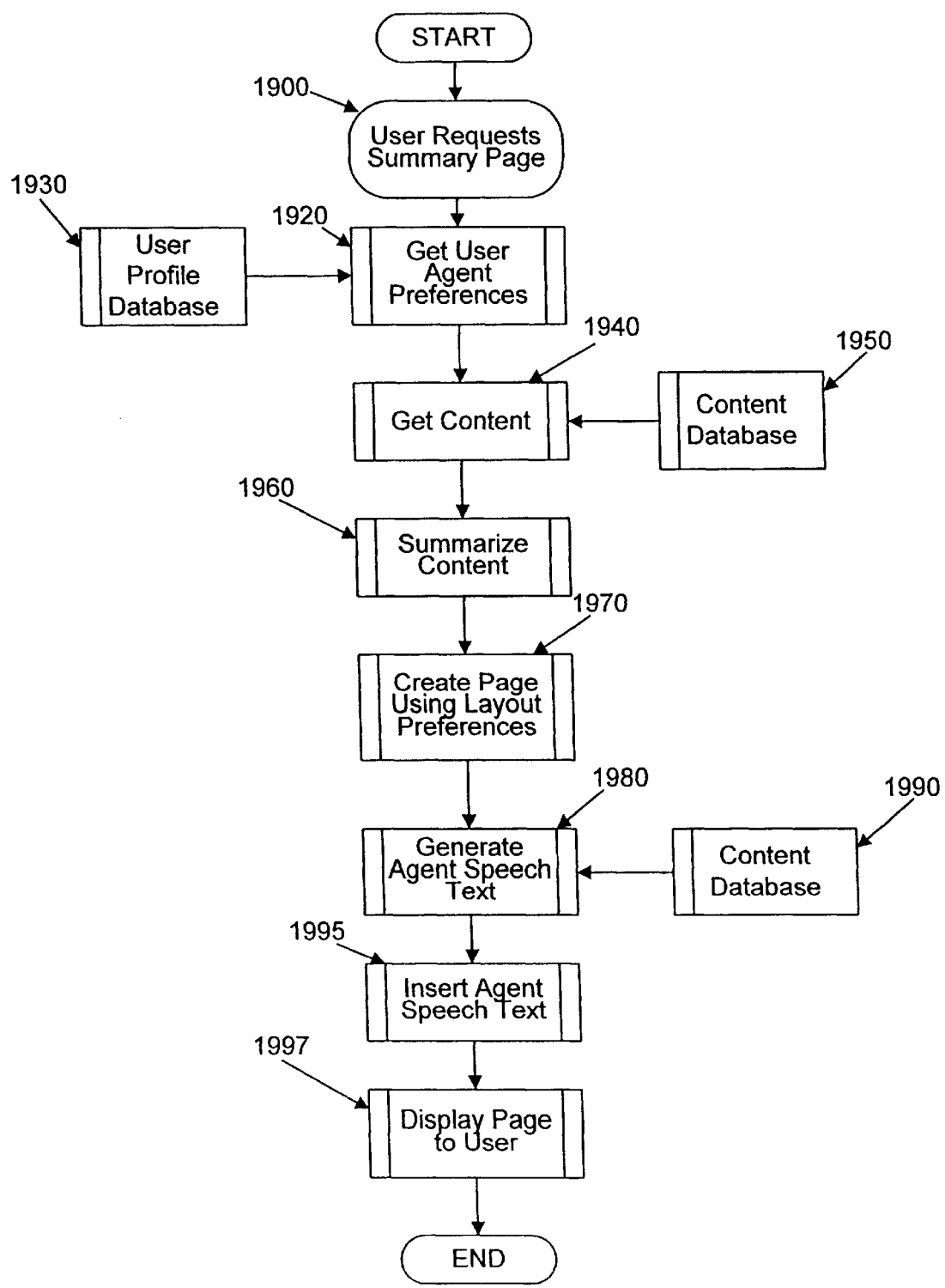
FIG. 19 is a flowchart of the agent processing for generating a verbal summary in accordance with a preferred embodiment.

FIG. 19 discloses the logic in accordance with a preferred embodiment processing by an agent to generate a verbal summary for the user. When the user requests the summary page 1900, the server gets the user's agent preferences 1920, such as agent type, rules and summary level from the user profile database 1930. The server gets the content 1940, such as emails, to do list items, news, and bills, from the content database 1950. The agent parses all of this content, using the rules stored in the profile database, and summarizes the content 1960. The content is formatted into a web page 1970 according to a template. The text for the agent's speech is generated 1980, using the content from the content database 1990 and speech templates stored in the database. This speech text is inserted into the web page 1995 and the page is returned to the user 1997.

Trusted Third Party

The above scenario requires the web site to maintain a guarantee of privacy of information according to a published policy. This system is the consumer's Trusted Third Party, acting on his behalf in every case, erring on the side of privacy of information, rather than on the side of stimulation of commerce opportunities. The Trusted Third Party has a set of processes in place that guarantee certain complicity with the stated policy.

"meCommerce"

Figure 20:
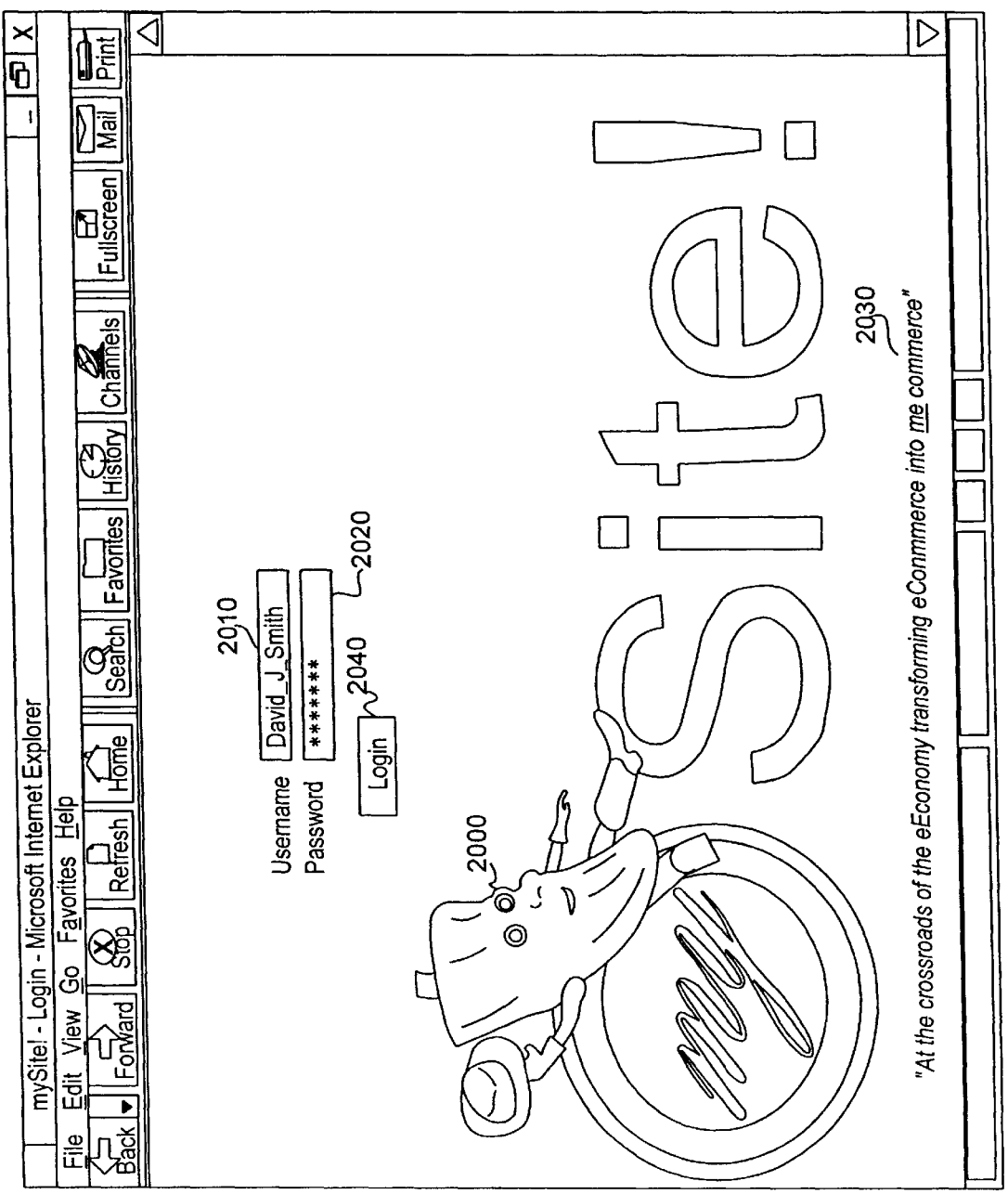
FIG. 20 illustrates a display login in accordance with a preferred embodiment.

This word extends the word "eCommerce" to mean "personalized electronic commerce." FIG. 20 illustrates a display login in accordance with a preferred embodiment. The display is implemented as a Microsoft Internet Explorer application with an agent 2000 that guides a user through the process of interacting with the system to customize and personalize various system components to gather information and interact with the user's personal requirements. A user enters a username at 2010 and a password at 2020 and selects a button 2040 to initiate the login procedure. As the logo 2030 suggests, the system transforms electronic commerce into a personalized, so called "me" commerce.

Figure 21:
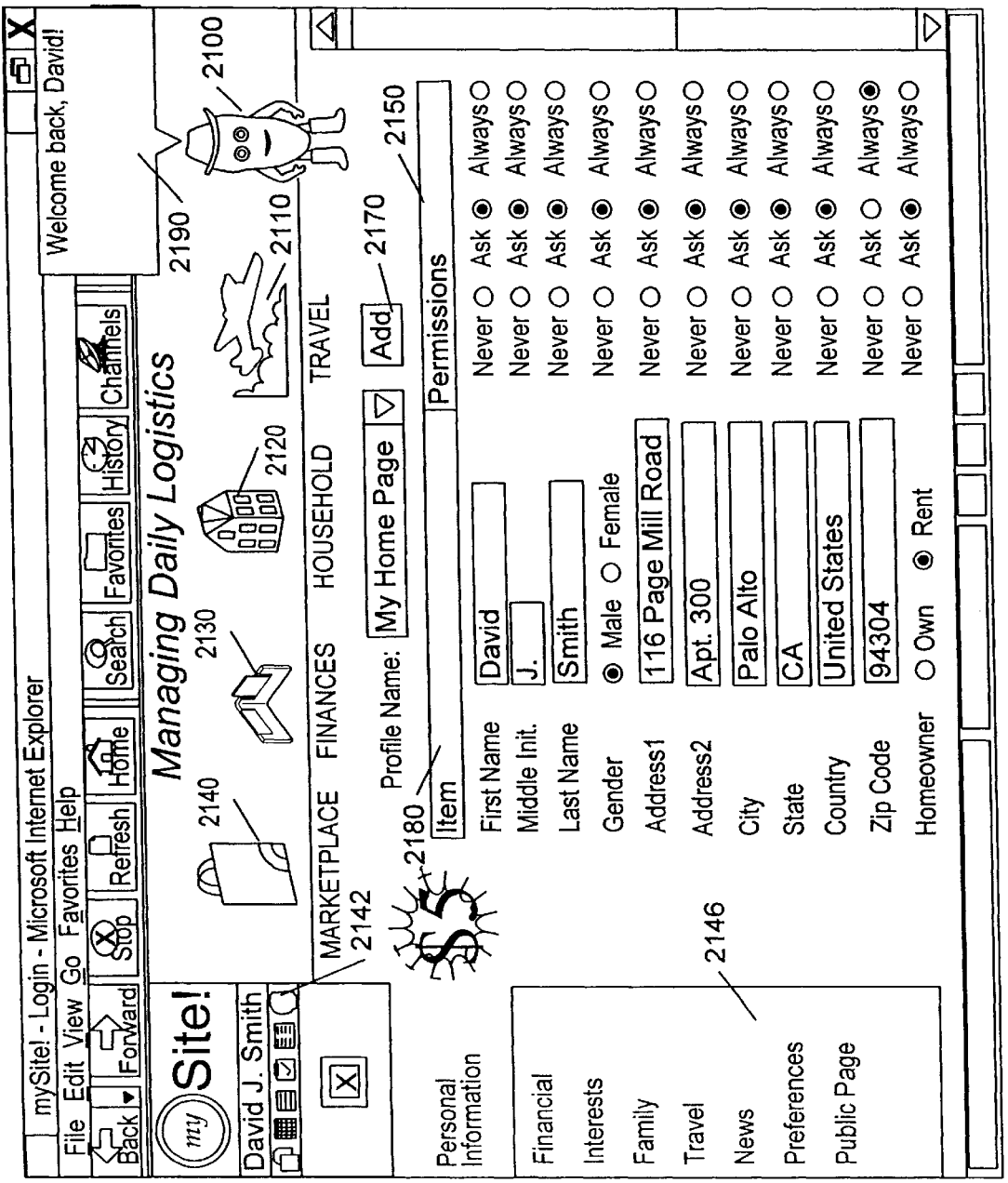
FIG. 21 illustrates a managing daily logistics display in accordance with a preferred embodiment.

FIG. 21 illustrates a managing daily logistics display in accordance with a preferred embodiment. A user is greeted by an animated agent 2100 with a personalized message 2190. The user can select from various activities based on requirements, including travel 2110, household chores 2120, finances 2130 and marketplace activities 2140. Icons 2142 for routine tasks such as e-mail, calendaring and document preparation are also provided to facilitate rapid navigation from one activity to another. Direct links 2146 are also provided to allow transfer of news and other items of interest. Various profiles can be selected based on where the user is located. For example, work, home or vacation. The profiles can be added 2170 as a user requires a new profile for another location. Various items 2180 of personal information are collected from the user to support various endeavors. Moreover, permissions 2150 are set for items 2180 to assure information is timely and current.

Figure 22:
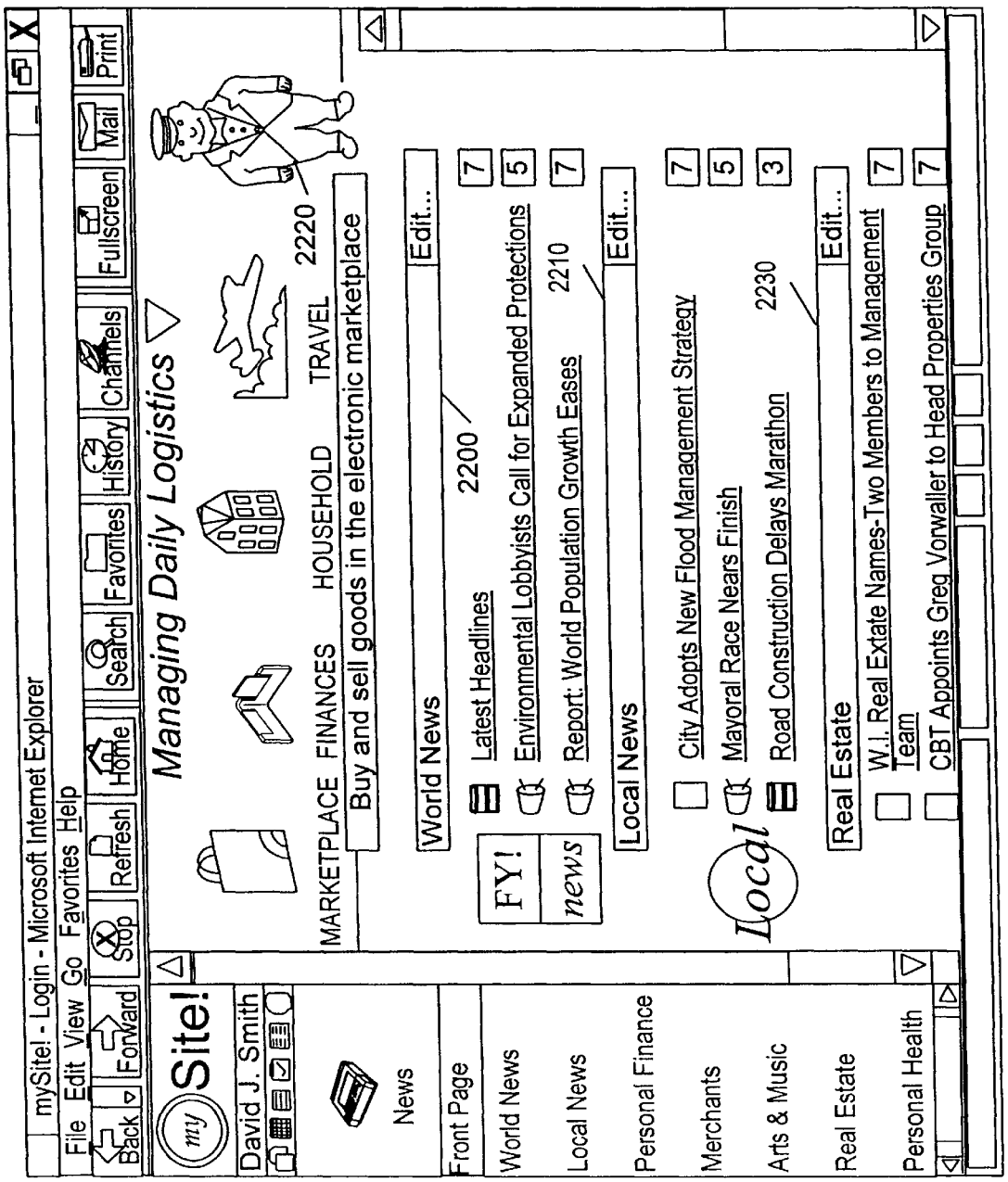
FIG. 22 illustrates a user main display in accordance with a preferred embodiment.

FIG. 22 illustrates a user main display in accordance with a preferred embodiment. World 2200 and local news 2210, is provided based on a user's preference. The user has also selected real estate 2230 as an item to provide direct information on the main display. Also, a different agent 2220 is provided based on the user's preference.

Figure 23:
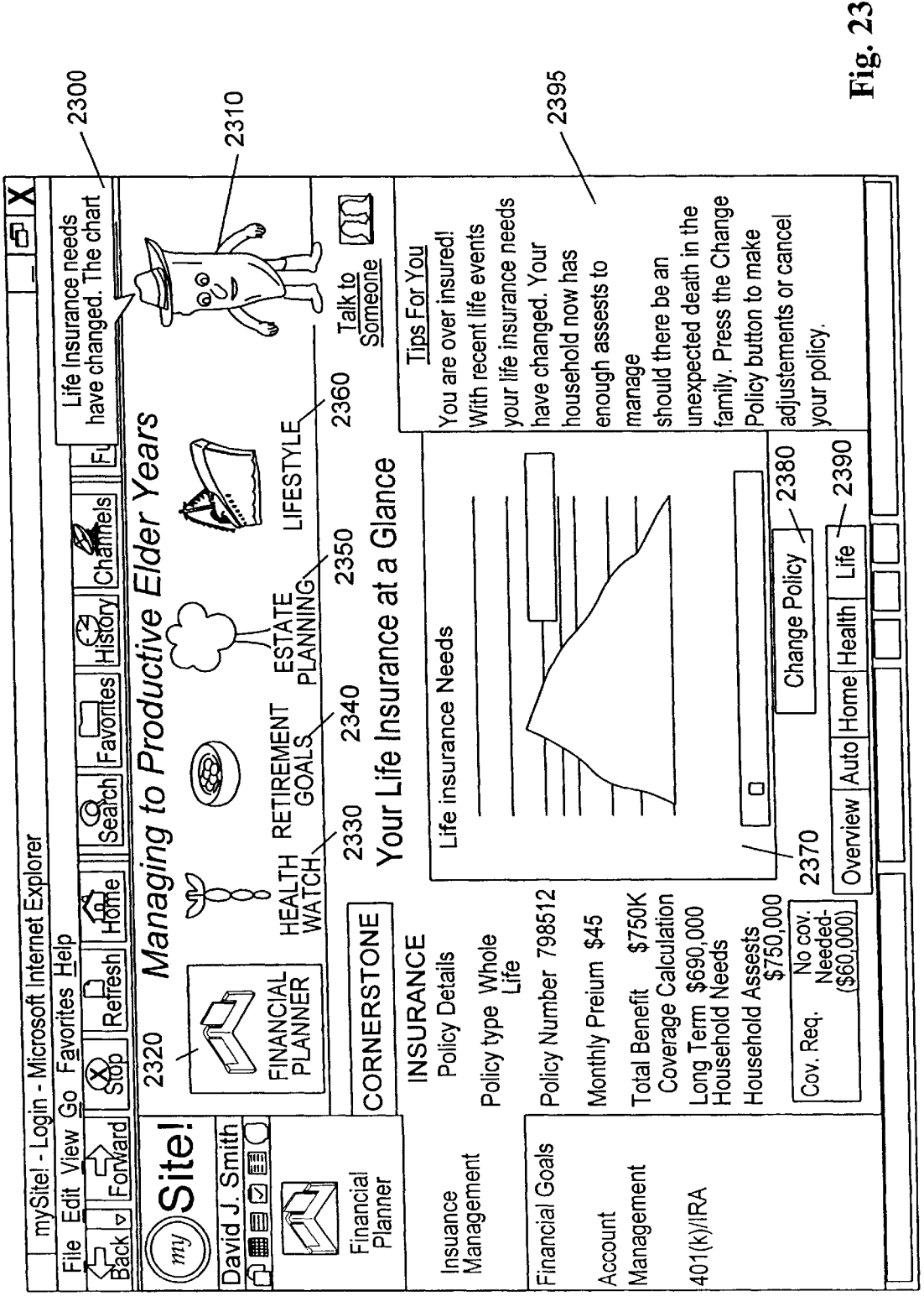
FIG. 23 illustrates an agent interaction display in accordance with a preferred embodiment.

FIG. 23 illustrates an agent interaction in accordance with a preferred embodiment. The agent 2310 is communicating information 2300 to a user indicating that the user's life insurance needs have changed and pointing the user to the chart that best summarizes the information for the user. Particular tips 2395 are provided to facilitate more detailed information based on current user statistics. A chart 2370 of the user's life insurance needs is also highlighted at the center of the display to assist the user in determining appropriate action. A button 2380 is provided to facilitate changing the policy and a set of buttons 2390 are provided to assist a user in selecting various views of the user's insurance requirements.

Event Backgrounder

An Event Backgrounder is a short description of an upcoming event that is sent to the user just before an event. The Event Backgrounder is constantly updated with the latest information related to this event. Pertinent information such as itinerary and logistics are included, and other useful information, such as people the user knows who might be in the same location, are also included. The purpose of the Event Backgrounder is to provide the most up-to-date information about an event, drawing from a number of resources, such as public web sites and the user's calendar and contact lists, to allow the user to react optimally in a given situation.

Vicinity Friend Finder

This software looks for opportunities to tell the user when a friend, family member or acquaintance is or is going to be in the same vicinity as the user. This software scans the user's calendar for upcoming events. It then uses a geographic map to compare those calendar events with the calendar events of people who are listed in his contact list. It then informs the user of any matches, thus telling the user that someone is scheduled to be near him at a particular time.

Information Overload

The term information overload is now relatively understood in both its definition as well as its implications and consequences. People have a finite amount of attention that is available at any one time, but there is more and more vying for that attention every day. In short, too much information and too little time are the primary factors complicating the lives of most knowledge workers today.

The first attempts to dynamically deal with information overload were primarily focused on the intelligent filtering of information such that the quantity of information would be lessened. Rather than simply removing random bits of information, however, most of these approaches tried to be intelligent about what information was ultimately presented to the user. This was accomplished by evaluating each document based on the user's interests and discarding the less relevant ones. It follows, therefore, that the quality was also increased.

Filtering the information is only a first step in dealing with information is this new age. Arguably, just as important as the quality of the document is having ready access to it. Once you have entered a meeting, a document containing critical information about the meeting subject delivered to your office is of little value. As the speed of business continues to increase fueled by the technologies of interconnectedness, the ability to receive quality information wherever and whenever it you are becomes critical. This new approach is called intelligent information delivery and is heralding in a new information age.

A preferred embodiment demonstrates the intelligent information delivery theory described above in an attempt to not only reduce information overload, but to deliver high quality information where and when users' require it. In other words, the system delivers right information to the right person at the right time and the right place.

Active Knowledge Management System Description

Figure 24:
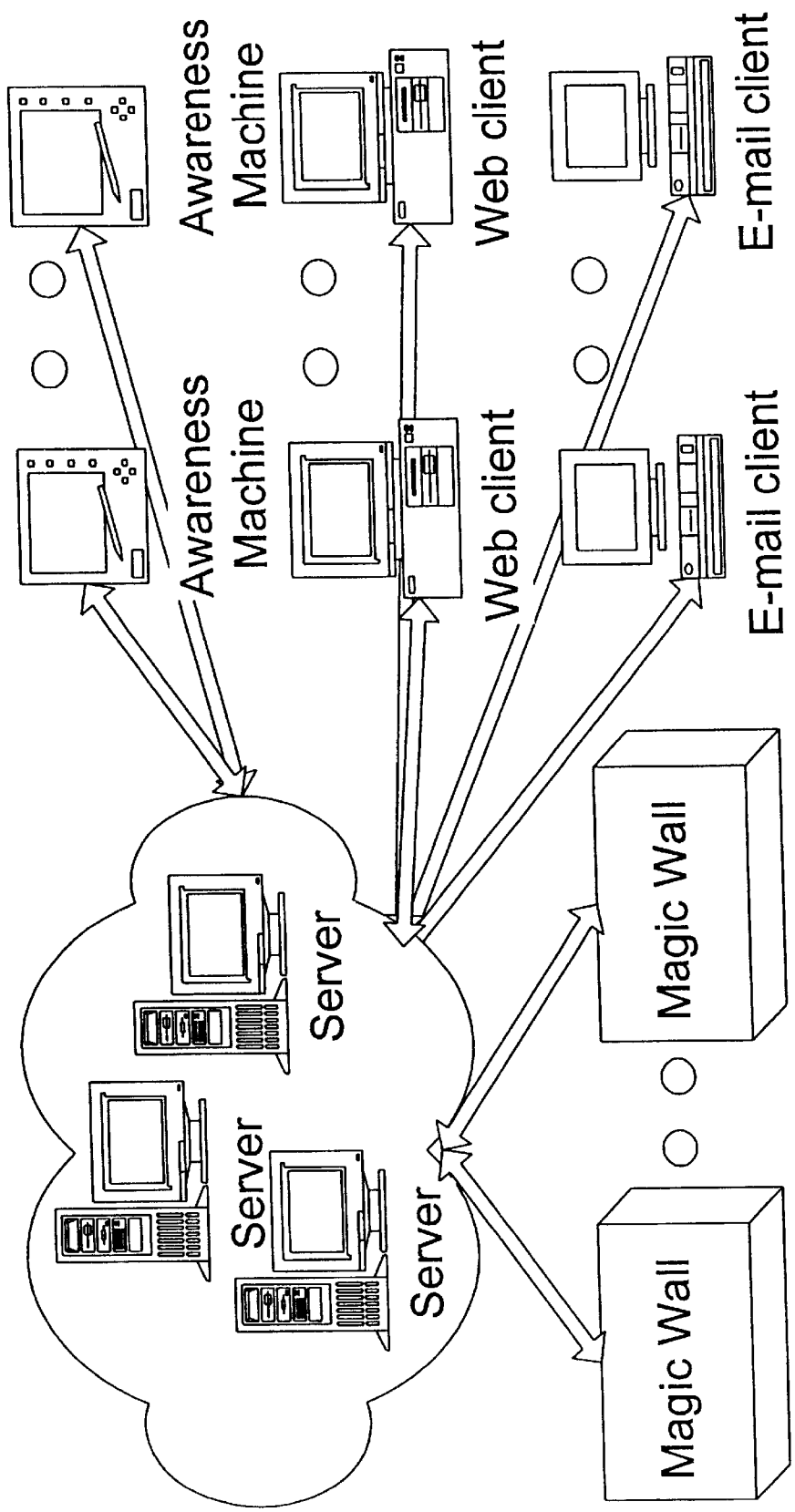
FIG. 24 is a block diagram of an active knowledge management system in accordance with a preferred embodiment.

FIG. 24 is a block diagram of an active knowledge management system in accordance with a preferred embodiment. The system consists of the following parts: back-end 2400 connection to one or more servers, personal mobile wireless clients (Awareness Machine)2430, 2436, public clients (Magic Wall) 2410, 2420, web clients 2446, 2448, e-mail clients 2450, 2460.

Back-end Server (2400) Processes

Figure 25:
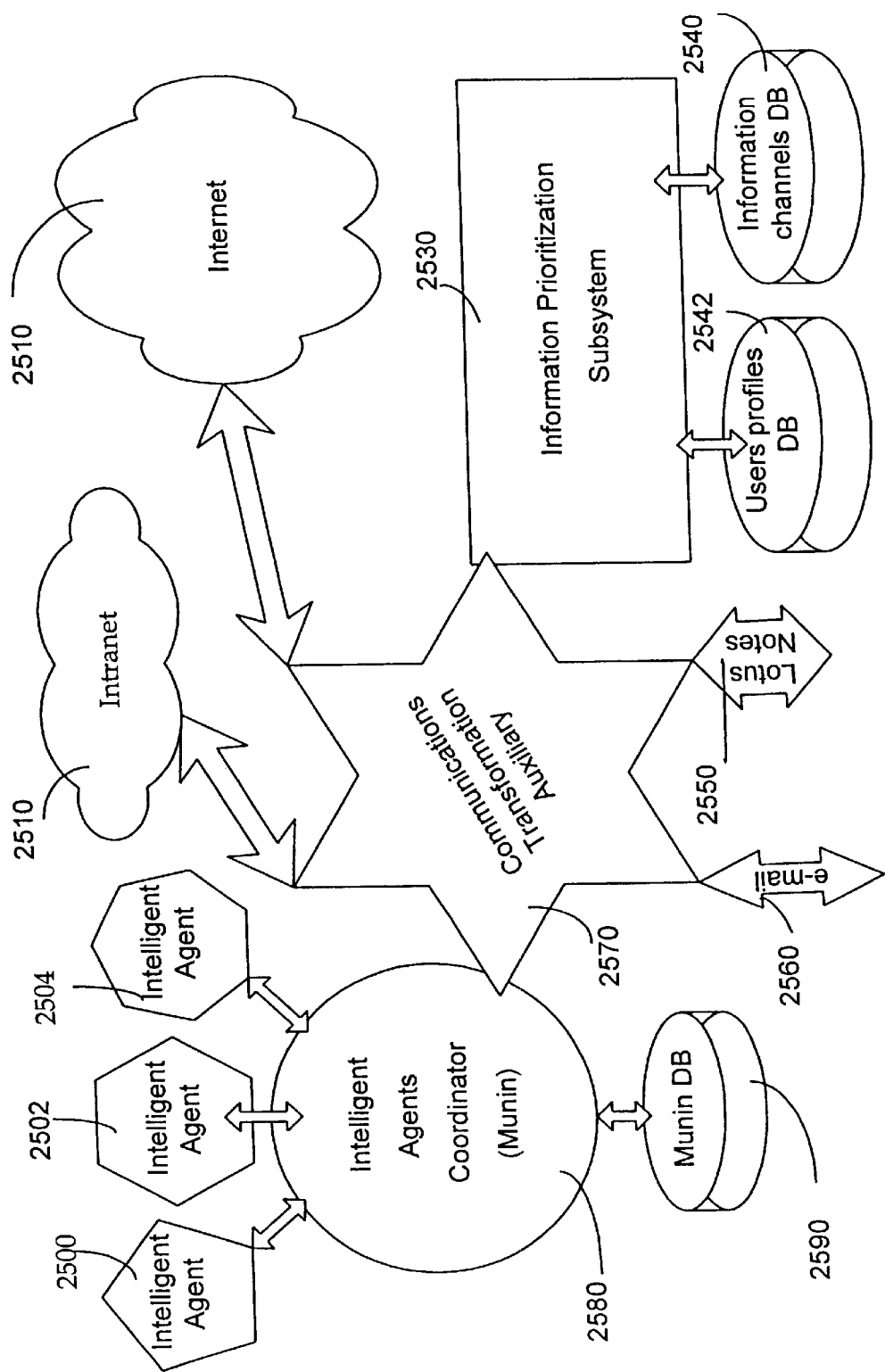
FIG. 25 is a block diagram of a back end server in accordance with a preferred embodiment.

FIG. 25 is a block diagram of a back end server in accordance with a preferred embodiment. The back-end (2400 of FIG. 24) is a computer system that has the following software active: Intelligent Agents Coordinator (Munin) 2580, information Prioritization Subsystem 2530, a set of continuously and periodically running information gathering and processing Intelligent Agents 2500, 2502 and 2504, User Profiles Database 2542 and supporting software, Information Channels Database 2542 and supporting software, communications software 2550, information transformation software 2560, and auxiliary software.

The Awareness Machine (2446 & 2448 of FIG. 24)

The Awareness Machine is a combination of hardware device and software application. The hardware consists of handheld personal computer and wireless communications device. The Awareness Machine reflects a constantly updated state-of-the-owner's-world by continually receiving a wireless trickle of information. This information, mined and processed by a suite of intelligent agents, consists of mail messages, news that meets each user's preferences, schedule updates, background information on upcoming meetings and events, as well as weather and traffic.

The Intelligent Agent Coordinator 2580 of FIG. 25 is also the user's "interface" to the system, in that whenever the user interacts with the system, regardless of the GUI or other end-user interface, they are ultimately dealing with (asking questions of or sending commands to) the Intelligent Agent Coordinator. The Intelligent Agent Coordinator has four primary responsibilities: 1) monitoring user activities, 2) handling information requests, 3) maintaining each user's profile, and 4) routing information to and from users and to and from the other respective agents.

Monitoring User Activities

Anytime a user triggers a sensor the Intelligent Agent Coordinator receives an "environmental cue." These cues not only enable the Intelligent Agent Coordinator to gain an understanding where users' are for information delivery purposes, but also to learn the standard patterns (arrival time, departure time, etc.) of each persons' life. These patterns are constantly being updated and refined in an attempt to increase the system's intelligence when delivering information. For instance, today it is not uncommon for a person to have several email accounts (work-based, home-based, mobile-based, etc.) as well as several different computers involved in the retrieval process for all of these accounts. Thus, for the Intelligent Agent Coordinator to be successful in delivering information to the correct location it must take into account all of these accounts and the times that the user is likely to be accessing them in order to maximize the probability that the user will see the information. This will be discussed further in another section.

Handling Information Requests

The Intelligent Agent Coordinator handles information requests from other agents in order to personalize information intended for each user and to more accurately reflect each user's interests in the information they are given. These requests will commonly be related to the user's profile. For instance, if an agent was preparing a traffic report for a user it may request the traffic region (search string) of that user from the Intelligent Agent Coordinator. All access to the user's profile data is accessed in this method.

Maintaining User Profiles

User profiles contain extensive information about the users. This information is a blend of user-specified data and information that the Intelligent Agent Coordinator has learned and extrapolated from each user's information and activities. In order to protect the data contained in the profiles, the Intelligent Agent Coordinator must handle all user information requests. The Intelligent Agent Coordinator is constantly modifying and updating these profiles by watching the user's activities and attempting to learn the patterns of their lives in order to assist in the more routine, mundane tasks. The Intelligent Agent Coordinator also employs other agents to glean meaning from each user's daily activities. These agents mine this data trying to discover indications of current interests, long-term interests, as well as time delivery preferences for each type of information. Another important aspect of the Intelligent Agent Coordinator's observations is that it also tries to determine where each user is physically located throughout the day for routing purposes.

Information Routing

Most people are mobile throughout their day. The Intelligent Agent Coordinator tries to be sensitive to this fact by attempting to determine, both by observation (unsupervised learning) and from cues from the environment, where users are or are likely to be located. This is certainly important for determining where to send the user's information, but also for determining in which format to send the information. For instance, if a user were at her desk and using the web client, the Intelligent Agent Coordinator would be receiving indications of activity from her PC and would know to send any necessary information there. In addition, because desktop PCs are generally quite powerful, a full-featured, graphically intense version could be sent. However, consider an alternative situation: the Intelligent Agent Coordinator has received an indication (via the keycard reader next to the exit) that you have just left the building. Minutes later the Intelligent Agent Coordinator also receives notification that you have received an urgent message. The Intelligent Agent Coordinator, knowing that you have left the building and having not received any other indications, assumes that you are reachable via your handheld device (for which it also knows the capabilities) and sends the text of the urgent message there, rather than a more graphically-oriented version.

Inherent Innovations

The Active Knowledge Management system represents some of the most advanced thinking in the world of knowledge management and human computer interaction. Some of the primary innovations include the following:

The Intelligent Agent Coordinator as illustrated above.

The development, demonstration, and realization of the theory of Intelligent Information Delivery Support for several channels of information delivery, all of which utilize a common back-end. For instance, if a user is in front of a Magic Wall the information will be presented in a multimedia-rich form. If the system determines that the user is mobile, the information will be sent by to their Awareness Machine in standard text. It facilitates delivery of information whenever and wherever a user requires the information.

Personalization of information based not only on a static user profile, but also by taking into account history of the user interactions and current real-time situation including "who, where, and when" awareness.

Utilization of fast and scalable Information Prioritization Subsystem that takes into account Intelligent Agents Coordinator opinion, user preferences, and history of user interactions. It takes the load of mundane decisions off the Intelligent Agents part therefore allowing the agents to be much more sophisticated and precise without compromising the system scalability.

Speech recognition and speech synthesis in combination with intelligent agent animated representation and tactile input provides for efficient, intuitive, and emotionally rewarding interaction with the system.

Client Reporting Subsystem Model

Context

The Reporting subsystem is used by other subsystems on the client to report (read: make a matter of record) various data. The subsystem makes no assumptions about the type of data it handles—the data could be fault reports (as part of an architectural service) or lead management information (as part of an application data service). The Reporting subsystem is in this sense part of the infrastructure, it is an underlying set of services available everywhere on the client. The Reporting subsystem uses the Communications subsystem to store and forward data.

Architecture Overview

The Reporting subsystem offers services to every client subsystem. It comprises a mechanism for messaging within the client application and between the client and the server. The Reporting mechanism uses the Communications subsystem to store and forward data. The Exceptions use this Reporting mechanism for reporting information about errors only.

Role

The Reporting subsystem provides a set of infrastructural services which allow architectural components to report information. The subsystem makes no stipulation about the information reported, although it does contain components that map to certain types of reported information, such as system faults or customer interaction information.

Part of the subsystem interface is presented as a set of Exceptions, which allow the automatic reporting of error conditions encountered during processing.

The subsystem accepts data and forwards it in an appropriate format to the Communications subsystem. It is captures and reports Exceptions generated during processing that are the result of error conditions. It is able to deal with any type of report that needs to be made, from error logging to sales leads. It is flexible enough to record new types of information as required. It is also flexible enough to be able to add new types of report as required. In addition, it is able to deal with the non-availability of certain information during the logging process.

Responsibilities

The Client Reporting Subsystem is responsible for providing a set of Exceptions for use by all parts of the application. The Subsystem is also responsible for logging fault reports, user interaction reports, application heartbeat reports, message receipts, referrals or leads, and Management Information System entries.

Exclusions

The subsystem is not responsible for gathering information from interface interactions or elsewhere; neither is it responsible for deciding what of a set of data needs to be reported. Reporting does not include the printing of reports.

| Component Specifications | |
| --- | --- |
| Client Exception Reporting Component | This is a set of Exception classes which, using the Client Reporting Component reporting services, stores and sends fault information |
| Client Reporting Component | This is the mechanism by which information for all reports are collected, formatted, and submitted to the Client Communications Subsystem. |

Creation, Existence, and Management

The key element of the subsystem is a static class which manages the creation of report objects—a report factory. This class is instantiated by the Communications subsystem (which manages client configuration) and is always available. It is a severe error if it is not. Reports are generated on an ad hoc basis as needed.

Sizing and Capacity

Whatever the requirements of the client architecture, the 'throughput' of the Client Reporting subsystem (understood as the number of reports, of every type, that are requested in a given time) will not place significant strain on system resources. Most of the capacity requirements for reports are absorbed by the Communications subsystem, which must arrange for the storage and transmission of those reports. Nevertheless, the subsystem must be able to deal with whatever throughput is demanded by the architecture, and the design takes into consideration the estimated workload generated by each part of the architecture.

Performance

Performance is not critical for the Client Reporting subsystem. Reported data, with a few exceptions, is stored before transmission, and so a delay before data is sent is anticipated. Certain types of severe or critical faults need to be reported at once, but the low bandwidth required for these transmissions will not present performance problems.

Design Guidelines

The reporting needs of the architecture fluctuate, although a core set of capabilities (fault reporting, lead management, interaction reporting) always remain requirements. The subsystem is flexible enough not only to extend or reduce its capabilities, but also to adjust the level of detail and the nature of data it records for each capability.

Implementation of the system follows the project Java coding standards.

Logical Components

Exceptions within the Client Exception Reporting component call the Client Reporting component to create fault reports.

| Component Descriptions | |
| --- | --- |
| Client Exception Component | This is a hierarchy of Exception classes structured to assist in the handling and passing of Exceptions. These Exceptions will accept information about the Exception event they represent. With this information and whatever |

| Component Descriptions | |
| --- | --- |
| | else the class knows about it's own event, the component will use the Client Reporting Component to create fault reports. |
| Client Reporting Component | A static report factory will accept requests from other components in the form of a signalled event. Based on this event, the factory will manufacture a report of a certain type. The report will then be populated with information supplied by the calling component or reporter. |

Submitting a Report

Component A signals the Client Reporting subsystem to indicate that a reportable event has occurred. The Client Reporting subsystem then requests information about the event and creates a report. Finally, the Client Reporting subsystem signals to the Client Communication subsystem that the report is ready to be sent.

Throwing an Exception

First, Component A signals that an exceptional event has occurred by instantiating an appropriate Exception. Second, Component A passes reportable event relevant information to the Exception. Third, Component A requests for the Exception to be thrown. Fourth, the Client Exception Reporting component submits a report to be sent based on the information available using the Client Reporting component as outlined above. Finally, the Client Exception Reporting component throws it's Exception.

Local Content Subsystem Model

Context

The Local Content subsystem provides all content required by the application. This includes both static and dynamic content. It also provides business services required by the application. It operates on a "storage and retrieval" basis, storing the data obtained from the user and the business, and providing mechanisms to retrieve that data. The Local Content subsystem is used by the ISF subsystem to provide content. It uses the Communication subsystem to receive business data.

Architecture Overview

Objects in the Local Content subsystem are created by the Initialization subsystem of the Application Architecture. Services provided by the Local Content subsystem are also accessed through the Application Architecture, via the Initialization and ISF subsystems.

The example components of the Local Content subsystem reflect different types of business knowledge and processes required by the application. User Data and Business Data involve data collected respectively from the user and the business. The Calculation component performs complex calculations, and the Product component represents the products used by the business. The Content Providers component defines static media content.

Role

The Local Content subsystem provides static and dynamic content to the application. It also provides all business-specific services required by the application.

Responsibilities

The Local Content subsystem provides static and dynamic media to the application. The Local Content subsystem also stores store user entered details, business data, and performs business calculations.

Exclusions

All application-specific behaviour is provided through the Application Personality. This behaviour is defined by Hamlet scripts, which also define navigation between scripts. The scripts are divided into metaphors, each of which is an embodiment of a style of interaction.

Access to media is provided through the Content Providers component, which belongs to this subsystem. However, the objects of this component are created automatically by the System Initialiser component from a contents file defined in the Application Personality.

Creation, Existence, and Management

The Business Data component is created and initialized at the time of System Initialization. It exist for the life of the system.

The User Data component is available for the entire time a customer is using the system. When a customer session ends, references to all objects in the User Data component are released so that the objects can be garbage collected.

Objects in the Local Content subsystem (with the exception of the Business Data Component) are created and initialized either internally or by the Initialization subsystem. References to these objects are managed by the ISF subsystem. Business Data objects are created, initialized and managed by the Communications subsystem.

Logical Components

The ISF does not actually know about the Local Content subsystem. The Local Contert subsystem implements a set of interfaces defined by the ISF. The Initialization subsystem uses the scripts defined in the Application Personality to define which objects (implementing those interfaces) need to be used to retrieve content. The ISF uses the Initialization component to create those objects, then manages them.

Developers of the Application Personality can easily view their scripts as directly managing the local content objects. This allows the local content objects to be developed without knowledge of the Application Architecture layer.

| Component Descriptions | |
| --- | --- |
| User Data | Stores and retrieves data entered by the user, and initiates calculations on stored data. |
| Business Data | Stores and retrieves data provided by the business. |
| Calculation | Performs complex calculations. |
| Product | Provides access to information associated with particular marketing products. |
| Content Providers | Provides access to static media. This is an implementation of an interface and is not documented as a separate component. |

Interface Support Framework Subsystem Model

Context

The Interface Support Framework subsystem is part of the Application Architecture Layer. It provides a rich interactive environment which exploits the full potential of a dynamic, multi-media interface. The ISF is built around a theatrical metaphor where every object is expected to exert dynamic behavior.

Objects within the ISF are initialized by the Application Initialization subsystem within the Application Architecture Layer and utilize the services of the Content Players, Printing and Reporting subsystems in the Technical Architecture Layer.

Architecture Overview

Objects within the ISF subsystem are initialized by the Application Initialization Subsystem. Reporting and Transaction Interface Services are used to log ISF data for the Technical Architecture layer to report or print. The Content Player subsystem within the Technical Architecture is used by the ISF to present media to the user.

The ISF subsystem is built upon a layered architecture which follows the Model-View-Controller pattern. The Factual component contains the object model of the business and definitions of business media content. The Visual component displays and manipulates media to provide a view of the business model to the user. The Behavioral component controls all interactions between the Visual and Factual components.

Role

The ISF subsystem provides the services for the application to present multimedia content in a controlled way. It also provides the capability to react to user input and affect changes to the scene.

Responsibilities

The ISF subsystem displays each scene of the application, and modifies the content of a scene while it is displayed. In addition, the ISF subsystem enables navigation between scenes, reacts to user interaction, retrieves business content, performs business functions and calculations, and provides common user interface constructs. Other responsibilities of the ISF include initiating print jobs and video conference sessions, reporting on user entry into a scene, duration of a session, user interaction with a role, user navigation, and reporting on errors occurring within the ISF. Finally, the ISF manages user sessions, and responds to system level events such as system start up and shutdown or screen paint requests.

Design Guidelines

The ISF subsystem provides the services for the application to present multimedia content. It is architecturally layered into three distinct components which parallel the Model-View-Controller paradigm. This separates the core business objects and their data (the Model), from the visual representation of this information (the View), from the logic to control and react to changes in the Model or the View (the Controller). The architecture provides boundaries between the graphical style of the system (Stage, Roles and Scenes), the operational code (Actors, Scene Director and Stage Manager), and the underlying Content Providers (Business Objects). These sections are the Visual, the Behavioral, and the Factual components.

The Factual Layer is not aware of the Visual layer. This allows the visual metaphor to change, without disrupting the underlying business domain model. The Behavioral level mediates between the Factual and visual layers and should avoid very complex interactions with either layer. Where possible, anonymous communications via a Publish/Subscribe pattern is used to avoid further interdependencies between the layers.

The Stage is identified as the display context. It is able to communicate only with the Locations it controls. It is hidden behind the StageManager, where all visual requests need to be managed.

The ISF is a layered system. All roles in a scene form a series of visual siblings. These roles can, in fact, contain and encapsulate other roles. This allows, through recursion, any number of distinct processing layers. Each child only communicates with its direct parent, surrendering control of communicating beyond to the parent. This containment relationship is possible in both the Visual and Behavioral layers.

To assist in navigation, Scene Thumbnails are maintained. The user may touch on a Scene Thumbnail to return to a previously visited Scene.

| Component Descriptions | |
|---|---|
| Visual component | user interaction and presentation of multimedia content |
| Behavioral component | application behavior and multimedia content retrieval |
| Factual component | provides multimedia content and business function services and calculations |

Process Control

This table describes the various key threads which execute within the ISF.

| Thread | Purpose |
|---|---|
| AWT | Sends windows messages (e.g., screen touches) to the ProcessController. This thread is created by the Java Virtual Machine. |
| Main | Initializes the application, then exits. This thread is created by the Java Virtual Machine. |
| Processing | Performs the actions initiated by the ProcessController. |
| Timer | Generates and actions time based system events such as session timeouts. |
| Video Status | Receives notification of video finish events and dispatches them to the ProcessController. |
| Audio Status | Receives notification of audio finish events and dispatches them to the ProcessController. |

User Touches Location on Stage

Description:

End users will touch the visible window of the application, the Stage. This will initiate a response from the application.

Actors: End user Components Involved: Visual

Key Objects Involved: Stage

Stage Processes User Touch

Description:

The application window will determine which location is affected by the touched area, and will notify the corresponding Role of a touch. The stage will also control the visual cue displayed on the window.

Actors: End user Components Involved: Visual

Key Objects Involved: Timer, User Interaction Reporter, Location, Media Player

Role Accepts User Touch Event

Description:

Each role is notified of a user touch. This will force it to request a media change in its corresponding media, and, once accomplished, to notify its actor of the user interaction.

Actors: Stage

Components Involved: Visual, Behavioral

Key Objects Involved: Actor, Role

Actor Activates Event Casting

Description:

The actor will cycle through all of its registered Casting Lists and activate all castings which are interested in the specific event. Castings behave polymorphically, and therefore the behaviour of how to respond is actually held in the Casting, not the actor.

Actors: Role, Execute Casting

Components Involved: Behavioral

Key Objects Involved: Actor, Casting, Stage Manager, Scene Director

Stage Manager Performs Scene Transition
   Description:
   The Stage Manager will replace the currently active scene with a new scene, based on the information in the Navigation Casting. It is important to control how the change occurs, to preserve the visual illusion of the Kiosk World.
   This scenario is also invoked when starting, or restarting, the application. In this case, there is no current Scene, but the application is told to transition to the first Scene of the application.
   Actor: Navigation Casting, System Initializer
   Components Involved: Behavioral, Visual
   Key Objects Involved: Stage, Scene Director, Session Manager
Scene Director Performs Cast Change
   Description:
   The Scene Director coordinates the activation of all timings to ensure that any messages to the Stage Manager are grouped together and engaged at an appropriate time. This will ensure that all changes to the Roles visible on the scene will occur at the same time.
   Actors: Content Casting, Slide Casting
   Components Involved: Visual, Behavioral
   Key Objects Involved: Scene Director, Stage Manager
Scene Director Performs Cast Change with Slide Effect
   Description:
   The Scene Director must onstage all non-sliding Roles and then display the content of the Slide Casting along a straight line until its final destination.
   Actors: Slide Casting
   Components Involved: Visual, Behavioral
Business Object Invokes Business Function
   Description:
   The application may request business information from the Business Domain Model (e.g., return a Repayment Amount). This interface also supports putting values into the business objects (such as store a Loan Term Amount). Each business object is provided a generic interface to invoke behaviors. The desired behaviour is specified in the Business Function Casting, and it capable of returning information to the Actor associated with the Business Object.
   Actors: Business Function Casting
   Components Involved: Factual
Stage Manager Times Out from Inactivity
   Description:
   The application must support a time out facility, in the event that the user walks away from the application prior to returning to the Attractor Screen. This will protect the privacy of details entered by users.
   Actors: Wait Timer
   Components Involved: Behavioral
Session Manager Resets Application
   Description:
   During the execution of the application, it may be necessary to reset the Stage to the first scene, and clear out the session. This may be triggered by system inactivity, or by direct user request dispatched through a business object.
   Actors: Stage Manager's Wait Timer, Business Object
   Components Involved: Behavioral
Reset Session Information
   Description:
   Each session stores information gathered about the user. At the end of a session, or by user request, it is possible to erase all entered data. This supports privacy.
   Actors: Session Manager
   Components Involved: Behavioral
Responsive Media Displays Media
   Description:
   The Visual component of the ISF is responsible for displaying all media (image, audio, video, text) to the Stage. It actually interfaces with the underlying media subsystem in the Client Technical Architecture. Each player is obtained through the Gatekeeper, and supports all code required to present the media to the user.
   Actors: Role
   Components Involved: Visual, Behavioral, Factual, Content Players
   Key Objects Involved: Responsive Media, Media Player, Stage
Application Requests Hard Copy Printout
   Description:
   The client application may request a print out of static information (check list), or dynamic information (product explanation including current interest rates and other dynamic components of the product, product simulation and/or line graph). This is initiated by the end user, through a Print Casting.
   Actors: Print Casting
   Components Involved: Behavioral, Printing
   Key Objects Involved: Business Object

Reporting Interface Subsystem Model

Context
   The Reporting Interface Subsystem collects information logged by the Application Architecture Layer and sends it to the Client Reporting Subsystem in the Technical Architecture Layer.
Architecture Overview
   The Reporting Interface information is logged by components within the Application Architecture Layer and sent to the Client Reporting Subsystem in the Technical Architecture Layer.
Role
   The Reporting Interface subsystem provides services to log user-interaction with the kiosk and report on software and hardware faults which occur within the Application Architecture Layer.
Responsibilities
   The Reporting Interface subsystem is responsible for gathering and logging user interaction with the kiosk by capturing what a user is doing with the system, e.g., which scenes they are visiting, which visual elements they are interacting with. The Reporting Interface subsystem also Gathers and logs information related to business products which the customer is interested in, the output of business functions which the customer has invoked and business data which the customer has input. Finally, the Reporting Interface subsystem captures information relating to the software and hardware performance of the kiosk. This information can then be used for error handling and fault management analysis.
Exclusions
   The Reporting Interface subsystem does not include services to gather and log customer related information such as the a customer name and telephone numbers.

Systems Management Subsystem Model

Context
   Systems Management involves the definition of a combination of automated and manual procedures. Automation is achieved primarily through the use of Systems Management Server (SMS). SMS is a tool within the Microsoft backoffice suite of tools which can centrally manage system software and hardware in a distributed environment.

Systems Management Subsystem Architecture

The Systems Management Subsystem architecture consists of two components, the Systems Management Server (SMS), and Fault Monitoring.

Systems Management Server (SMS)

Systems Management Server (SMS) is a Microsoft tool that can be used to distribute software/content, take software audits, perform fault diagnosis and take remote control. SMS is supplemented by a component developed for the architecture, namely the File Transfer Utility.

Fault Monitoring

The Kiosk is monitored real-time through a Heartbeat message system. Heartbeat pulses are sent from the Kiosk at a configurable rate (say one every minute) and are monitored at a console running the Kiosk Monitoring Application. If the status of a Kiosk changes to indicate a fault, monitoring application will initiate the appropriate action. Some errors will be handled through the existing Operations Center. The routing of these errors is covered in the Application Services Subsystem.

Role

SMS is used for medium sized software distribution (both code and content) and for fault diagnosis of the remote kiosks. There are a large number of features that make SMS a flexible and useful support facility. Fault monitoring will provide the means to view the real-time status of each kiosk and associated peripherals. When a problem occurs at a particular kiosk (such as running out of paper), the kiosk will be brought to the attention of a operations representative. It will be possible to observe the kiosk status to verify the resolution of the problem.

Responsibilities

The SMS is responsible for software distribution, hardware fault management and diagnosis, and client remote re-boots. The SMS also provides a user interface to selectively view the status of all kiosks in the network.

Creation, Existence, and Management

The SMS resides on a dedicated server in accordance with a preferred embodiment and is available at all times.

Performance

The elapsed time between a fault occurring on an MMT and subsequently being displayed to operations is dependent upon the frequency of the heartbeat, the ability for the application server to process the heartbeat and the frequency of refresh on the operations terminal. An example in accordance with a preferred embodiment is presented below.

|  | Elapsed Time (minutes) |
|---|---|
| A fault occurs immediately after a heartbeat message is sent. | 1:00 |
| The Heartbeat message is sent to the Application Server | 0:01 |
| The Application Server receives and processes the heartbeat message | 0:01 |
| The operations Fault Monitoring Application has just refreshed and is only refreshing once every 2 minutes. | 2:00 |
| The Fault Monitoring Application refreshes it's kiosk status main window | 0:05 |

-continued

|  | Elapsed Time (minutes) |
|---|---|
| The Fault Monitoring Application refreshes it's kiosk status view (This time is for only one view window open. If there are more than one view windows open this time should be multiplied by the number of open view windows) | 0:05 |
| Total | 3:11 |

If a heartbeat message is not received from a kiosk within five minutes, (configurable) the Fault monitoring will set the kiosk status to Unknown. This time lag is required to avoid erroneously reporting MMT machines as unknown when the real problem lies in a slightly slower than normal processing of a heartbeat message.

Logical Components

An SMS site comprises of two components—a Primary Site and Clients. A primary site is the top most level in the SMS hierarchy. It contains its own SQL database to store system and inventory information for itself and other secondary sites underneath it. Clients (kiosks) are administered from the primary site. The client sends its hardware/software information to SMS server through the SMS Inventory service.

Fault Monitoring

After a configurable time interval the Client takes a status check of the Machine, Printer and the Application and sends it to the server in a heartbeat message. The server then places the status into a Kiosk Status Database that is monitored by operations staff for faults.

Server Communications Subsystem Model

Context

The Server Communications subsystem is part of the Server Technical Architecture. The Server Communications subsystem handles all communications between clients, the central server, and the mainframe host.

Architecture Overview

The Asynchronous Messaging component provides the asynchronous message based communication between the client and the server, using standard Internet mail protocols, SMTP and POP3.

The Business Process Access Module component provides the common point to invoke predefined business functionality such recording interaction information from the MMT. HTTP is the protocol used to communicate with HTTP servers on the World Wide Web. It is used in the MMT to distribute small updates of application components and content during the client configuration process on start-up. Access to mainframe database resident data is done by replicating the required database tables to corresponding server resident database tables. The reverse process is used to centrally store the data accumulated on the server to the mainframe database tables. Generic alerts from the server are transmitted to the mainframe through an interface to the mainframe's front end processor.

Role

The role of the Server Communications subsystem is to Provide the server with communications facilities between the MMT (or Internet) client and the network server and between the network server and the mainframe systems. In addition, the Server Communication subsystem isolates and provides access to organization specific functionality.

Responsibilities

The Server Communication subsystem complies with standard Internet protocols, to allow ease of porting to that delivery channel. In addition, The Server Communication subsystem provides reliable asynchronous communication between the client and the application server, and controlled and reliable access to organization specific functionality. Finally, the Server Communication subsystem provides a facility to deliver updates to the configuration of the client, such as application components and content, and provides access to the organization's legacy systems through pre-defined processes, such as database replication and generic alert reporting.

Exclusions

Server Communication is confined to invoking modules which conform to the ACT messaging architecture. If communication to another platform is required, this must be located within the external systems module using the organizations messaging or access methods.

Transaction Interface Subsystem Model

Architecture Overview

Transactions are initiated by components within the Application Architecture Layer and sent to the Client Reporting Subsystem in the Technical Architecture Layer. The Transaction services identified in this document are not implemented as separate components in their own right, but are implemented as extensions to existing Application Architecture components.

Role

The Transaction Interface subsystem is responsible for providing an interface to the application for storing of contact information about the end-user. These include, but are not limited to information required to complete a loan, survey-based information on customer demographics, account balance inquiry, and funds transfer.

Customer Lead Transaction Execution

The customer lead transaction execution application facilitates the Interface Support Framework and enables the services of the Reporting Subsystem of the Technical Architecture to support the gathering and storing of information about the end-user.

Exclusions

The current usage of the Transaction Interface assumes that only asynchronous communications are available.

Server Application Services Subsystem Model

Architecture Overview

The Application Services Sub-system includes a set of definitions for building the MMT server application and architecture modules.

Role

The Server Application Services sub-system includes the set of services and definitions for accessing application and architecture functionality. This subsystem defines the structure and support services for building and executing applications and modules on the Application Server or Operations workstation platform. The functionality supported includes transaction processing t to/from the MMF: such as customer referral information, customer interaction information, MIS information, fault information, product rates and prices information, application configuration information, message receipt information, and heartbeat status information.

Responsibilities

The Server Application Services sub-system processes application business logic on the server independently from the underlying database management system. The application business logic includes customer referral information, customer interaction information, MIS information, fault information, product rates and prices information, application configuration information, message receipt information, and heartbeat status information.

The Server Application Services sub-system also provides a common service available to all server and client applications to log an error, decode a given code (for example, '1'=NSW, '2'=QLD etc.), and retrieve configuration information from the registry located on each machine.

Finally, the Server Applications Services sub-system invokes a Business Process (BP) for a given BP message.

Logical Components

The Server Application Services sub-system includes Common Servers, Data-Access Module, Business Process, and the Business Process Access Module. Definitions of each component are given in below.

Component Descriptions

Definitions

Common Services. Common services to support the development of application functionality include decoding codes tables, retrieving configuration information from the registry, message handling, and the support for logging and handling server application errors.

Data Access Module. A data access module (DAM) provides access to data within the application database. A DAM performs specific data access such as Insert, Delete, Update, Select, Select All across one or more tables. It is an MFC Extension DLL encapsulating a Recordset object which uses ODBC to access the underlying DBMS. The DAM definition outlines how these modules are used and coded.

Business Process. A business process (BP) is the application or architecture functionality that may be invoked by the Business Process Access Module architecture. A BP is identified by a message type. A BP accepts a request message defined by the BP and may provide a response message for synchronous messages. Database access is provided to the BP by DAMS. A BP is an MFC extension DLL with a defined entry point.

Business Process Access Module. This component is detailed in the communications sub-system. The Business Process Access Module (BPAM) is the architecture component that provides access to business processes. The BPAM invokes a BP for a given message type. The BPAM accesses the message address table to lookup BP module details. This component is detailed in the communications sub-system.

Wireless Electronic Valet in Accordance With A Preferred Embodiment

One embodiment of the present invention is an a Mobile Portal Platform including a Mobile Portal and an Electronic Valet. The Electronic Valet is a hand held wireless computer device executing Thin Client Software. Integrated into the Electronic Valet are various sensors, such as GPS, Bio-sensors, and Environ-sensors. In addition, recording equipment, such as a camera and auido recorder, is also integrated into the Electronic Valet. The Mobile Portal includes a Mobile Portal Server which is connected to various third party content and service providers through the Internet or a Mobile Portal Extranet.

Figure 26:
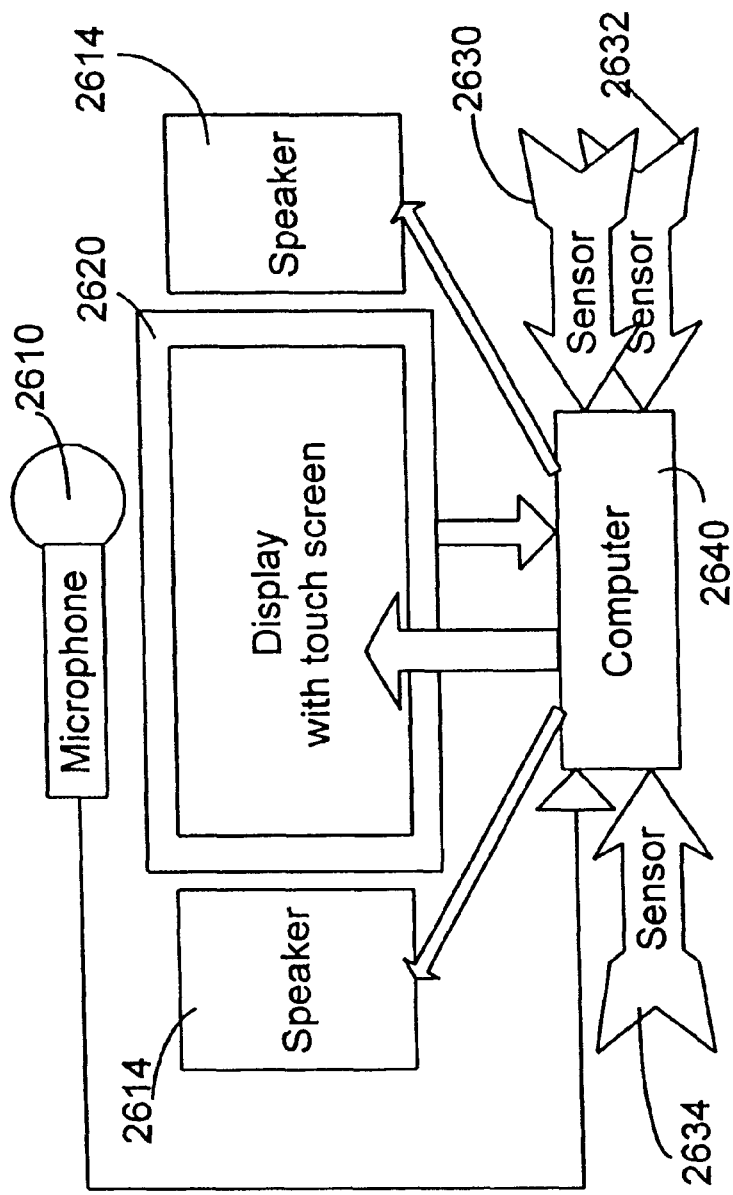
FIG. 26 is a flow chart illustrating how the hardware and software of one embodiment of the present invention operates.

FIG. 26 is a flow chart illustrating how the hardware and software of one embodiment of the present invention operates. An Electronic Valet 2602 receives input data from sensors, GPS, camera, microphones, and other user inputs 2600 integrated with the wireless hand held device. The Thin Client application executing on Electronic Valet 2602, as discussed in detail below, allows the Electronic Valet 2602 to execute many different software applications without the need for a large amount of internal memory and storage capacity. The Electronic Valet 2602 forms a message based on the data received and the user input. The Electronic Valet 2602 then transmits the message via antennae 2604 to the Mobile Portal 2606. The Mobile Portal 2606 parses the message received from the Electronic Valet 2602 and forms a new message based on the message received. The Mobile Portal 2606 then determines the appropriate third party service provider 2608 to transmit the new message to, based on the content of the message received from wireless hand held device 2602, and then transmits the new message. The third party service provider then performs the appropriate service and transmits the result back to the Mobile Portal 2606. The Mobile Portal then forms a message based on the data received from the third party service provider 2608 and transmits the message back to the Electronic Valet 2602. The Electronic Valet 2602 then formats and displays the data received. The Electronic Valet 2602 utilizes a wireless modem such as a Ricochet SE Wireless Modem from Metricom.

Of course, wireless performance isn't nearly as reliable as a traditional dial-up phone connection. We were able to get strong connections in several San Francisco locations as long as we stayed near the windows. But inside CNET's all-brick headquarters, the Ricochet couldn't connect at all. When you do get online, performance of up to 28.8 kbps is available with graceful degradation to slower speeds. But even the slower speeds didn't disappoint. Compared to the alternative—connecting via a cellular modem—the Ricochet is much faster, more reliable, and less expensive to use. Naturally, the SE Wireless is battery powered. The modem has continuous battery life of up to 12 hours.

Thus, utilizing the wireless modem, a user may utilize the Mobile Portal 2606 via the Electronic Valet 2602. Using appropriate key(s), the user may select a service to use in concert with appropriate data obtained from sensors, GPS, camera, microphones, and other user inputs 2600. In certain circumstances, data may be automatically sent to select services based on the type and value of the data obtained by the Electronic Valet 2602. For example, when an integrated bio-sensor obtains certain predefined data values, an appropriate emergency care provider would be automatically contacted. In addition, the data obtained from sensors, GPS, camera, microphones, and other user inputs 2600, may also be combined before being sent to an appropriate service provider. For example, in the example above, GPS position data may be sent with the bio-sensor data to the emergency care provider. The emergency care provider would then know the patient's biological data and the location of the patient. Appropriate service could then be provided.

Mobile Portal Platform

The Mobile Portal Platform is a high-impact, server-based application in accordance with a preferred embodiment that is focused on the theme of delivering services and providing a personalized experience for each customer via a personal site located on a server. The services are intuitively organized around satisfying customer intentions—fundamental life needs or objectives that require extensive planning decisions, and coordination across several dimensions, such as financial planning, healthcare, personal and professional development, family life, and other concerns. Each member owns and maintains his own profile, enabling him to create and browse content in the system targeted specifically at him. From the time a demand for services is entered, intelligent agents are utilized to conduct research, execute transactions and provide advice. By using advanced profiling and filtering, the intelligent agents learn about the user, improving the services they deliver.

A preferred embodiment of a system utilizes a Windows CE PDA equipped with a GPS receiver. The embodiment is configured for a mall containing a plurality of stores. The system utilizes a GPS receiver to determine the user's location. One advantage of the system is that it enables the retrieval of data for nearby stores without relying on the presence of any special equipment at the mall itself. Although the accuracy of smaller, inexpensive receivers is limited to approximately 75–100 feet, this has thus far proven to be all that is necessary to identify accurately the immediately surrounding stores. The system uses generated data rather than actual store ads and prices. Well structured online catalogs are used. Other embodiments utilize agents that "learn to shop" at a given store using a relatively small amount of knowledge. Moreover, as retailers begin to use standard packages to create online catalogs, we can expect the number of differing formats to decrease, resulting in a tractable number of competing formats. As electronic commerce progresses, it is not unreasonable to expect standards to evolve governing how merchandise offerings are represented.

Goal Specification

Before leaving on a shopping trip, a shopper creates a shopping list of items by selecting from a preexisting set of approximately 85 product categories (e.g. men's casual pants, women's formal shoes, flowers, etc,). They also indicate the shopping venue they intend to visit from a list of malls.

Initial Store Selection

Upon arriving at the mall, begins by suggesting the closest store that sells at least one item of a type entered by the user during goal specification. Along with the store name a system in accordance with a preferred embodiment prepares a list of the specific items available and their prices. A map of the mall displays both the precise location of the store and the shopper's current location. The shopper queries the system to suggest a store at any time based on their current location.

Browsing

Figure 27A:
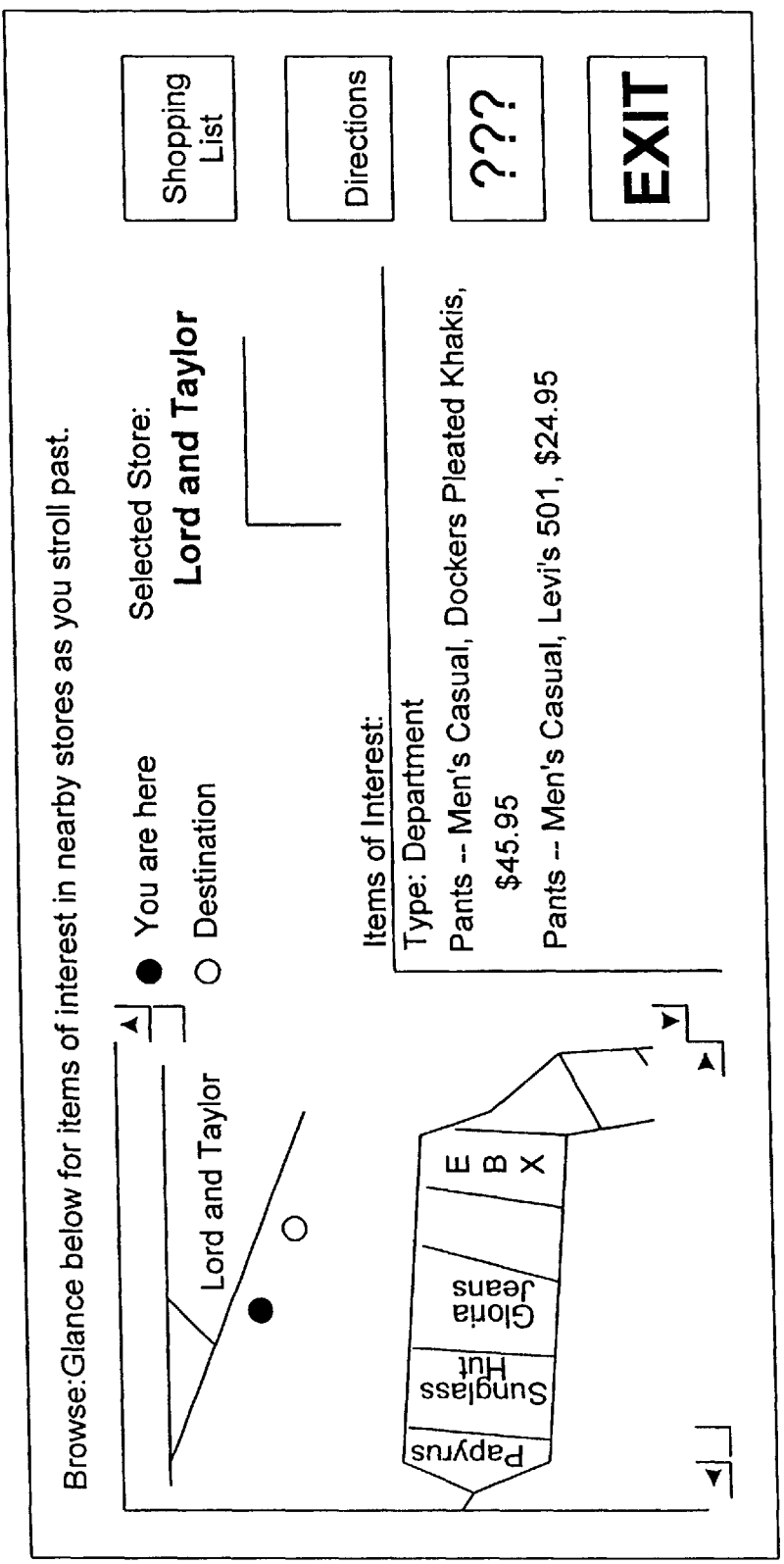
FIG. 27A illustrates a display of the browser mode in accordance with a preferred embodiment.

To address the need of many shoppers to visit malls or shop generally without a particular destination in mind. FIG. 27A illustrates a display in accordance with a preferred embodiment of the invention. The display operates in a browse mode for use by shoppers as they stroll through the mall. In browse mode the system suggests items of interest for sale in the stores currently closest to the shopper. An item is considered to be of interest if it matches the categories entered in the goals screen. If there are no items of interest, the general type of merchandise sold at that store is displayed, rather than specific items. As the shopper strolls a map displays his or her precise current location in the mall. If an item displayed is selected by the shopper while browsing, the system alerts the shopper to the local retailer offering the same product for the lowest price, or announces the best local price. This search is restricted to the local mall, as that is the assumed radius the shopper is willing to travel.

Alternatives

It is worth emphasizing that the current inventive agent will support broader aspects of the shopping task, for example, it could operate as bi-directional channels. That is, not only can they provide information to the shopper, but, at the shopper's discretion, they may provide information to retailers as well. In this embodiment, the system indicates a shopper's goals and preferences to a retailer-based agent, who, in turn, responds with a customized offer that bundles service along with the product. Enabling the customization of offers is crucial to gaining the cooperation of retailers who are reluctant to compete solely on price and of value to customers who base their purchases on criteria other than price. While the preferred embodiment focuses on location-based filtering primarily in the context of the shopping task, the current invention provides the basis for "physical task support" agents that provide an information channel to people engaged in various tasks in the physical world.

The Predictive Value of Location

The present invention is a significant advance over non location based agents because a users physical location is often very predictive of his or hers current task. If we know someone is at a bowling alley or a post office we can reasonably infer their current activity. Knowledge of a user's current task largely determines the type of information they are likely to find useful. People are unlikely to concern themselves with postal rates while bowling, or optimal bowling ball weight while buying stamps. In addition, knowledge of the resources and obstacles present at a particular location suggest the range of possible and likely actions of someone at that location. This awareness of a user's possible and likely actions can be used to further constrain the type of information a user is likely to find useful. For example, knowledge of a restaurant's wine list could be used by a recommended system to constrain the wine advice it presents.

Knowledge of a shopper's precise location in a shopping mall is valuable because it enables the identification of the stores immediately surrounding the shopper. The offerings of the stores closest to the shopper represent the immediate choices available to the shopper. Given that shoppers place a premium on examining merchandise first hand and that there is a cost associated with walking to other stores, the merchandise of the closest surrounding stores constitute the most likely immediate selections of the shopper. Consequently, among the most useful information provided at any given time is the availability of merchandise in the surrounding stores that matches their previously stated goals.

People tend to move to different locations while performing many of their our tasks. This suggests that their immediate surroundings do not completely capture the full range of options they may have. In fact one of the main reasons for leaving a location is to perform an action that is not possible at the current location.

Nevertheless, one does tend to address most tasks within relatively local areas. Thus while their immediate surroundings suggest the options they have available at a given point in time, a broader view of a location will often capture the options they are likely to consider over the course of a task. In the case of mall shopping, for example, the stores immediately surrounding the shopper represent the options available at that moment. Mall shoppers, however, are generally willing to travel to any store within the mall. Therefore the potential options over the entire shopping trip include all the stores in the mall. Accordingly, information is presented on offerings of interest only from the immediately surrounding stores because these are the immediately available options. When asked for alternatives, the system restricts itself to all the stores within the mall—the area within which the shopping task as a whole is likely to be performed. Being alerted that a store hundreds or thousands of miles away sells the same merchandise for a few dollars less than the cheapest local alternative is of little value in cases when shoppers require a first hand examination of the merchandise in question or are not willing to wait for shipping.

PHYSICAL VS. ONLINE SHOPPING

In addition to the significant advantages over non-location based agents the present invention over comes disadvantages o online (or web) shopping. It is tempting to argue that online shopping will soon become the predominant mode of shopping, pending only greater penetration of home computers, the expansion of online offerings, and better online shopping tools. At first glance it would therefore appear to be a mistake to begin using location to support an activity that will become virtualized. Already we've seen the emergence of a number of software agents that support online shopping. For example, programs that allow users to identify the cheapest source for a music CD, given a title. Similar programs have been developed for buying books, such as BargainBot. These systems demonstrate the potential of electronic commerce web agents to create perfect markets for certain products. The success of these agents will encourage the development of similar web shopping agents for a greater variety of goods.

The Limitations of Online Shopping

Certainly online shopping will continue to grow and the trend towards more powerful online shopping agents will continue. Nevertheless, it also seems clear that no matter how sophisticated web-agents become, traditional physical shopping will continue to dominate the market for the foreseeable future. Several inherent difficulties of online shopping will ensure the continued reliance on physical shopping:

Non-fungible Goods

Web-based shopping agents have typically enabled users to identify the cheapest price for fungible products such as books and music CDs. While this capacity to create "perfect markets" for such commodities is of great benefit to consumers, several difficulties exist that will complicate applying these approaches to arbitrary products.

Commodities are particularly well suited to shopping agents because it is easy to make comparisons between competing offers. Because commodities are fungible, one of the very few dimensions upon which they differ is price. Price therefore becomes the primary, if not sole, criterion upon which purchasing decisions are made.

As soon as we move beyond commodities, however, several other criteria become important. For example, how do we compare items such as sweaters, mattresses, or tables? In addition to price we care about the materials used, the color, how it fits and feels, and the workmanship. Similar problems apply to most other products.

Imprecise Goal Specification

A second, related difficulty lies in communicating our desires to an agent. Shopping agents are great if the user knows the precise commodity he or she wants. Then they can simply enter the product by name. Unfortunately, if they don't have a specific item in mind when they shop, then the problem of conveying what is wanted to an agent becomes more difficult. For example, how does the user tell an agent what kind of lamp they want for their living room?

Undeveloped Preferences

Interfaces that allow shoppers to include descriptive features like price ranges, color, options, brands, etc, can help address the above problem, but they are not enough. Much of the time shoppers either haven't formed preferences or can't articulate their desires until after they've started shopping and had a chance to examine various examples of the target products.

Shopping is Entertainment

People like to shop and do so without having a specific purchase in mind. One study found that 42% of consumers are "non-destination shoppers" that visit the mall primarily for leisure browsing and socializing.

Shopping is Sensory

Even if the user could effectively provide these details most would be unlikely to delegate a purchasing decision to such an agent. After all, many people are uncomfortable even trusting spouses to make appropriate purchases on their behalf. Most people want to see and touch first hand what they're considering before making a purchase decision. The few preferences they may provide an agent cannot replace this rich, first-hand experience. At best such preferences could be used to generate a candidate set for shoppers to consider.

Instant Gratification

Shopping is often a very emotional activity. People are pleased with their purchases and often can't wait to get home to try them out. The inherent delay between online purchases and their receipt is a significant issue to those who simply must take home their selections as soon as they see them.

In the end, consumers will continue to engage in physical shopping because of the limitations listed above. However, the fact that the task can't completely be delegated to software agents does not rule out a role for them. First, users find them useful for purchasing commodities when they know what they want. A second role, however, is to support the physical shopping task itself, throughout the time that a person is engaged in it. This, of course, is the approach taken in the SHOPPER'S EYE project.

SHOPPER'S EYE

At first blush it may seem that the current invention is subject to some of the same limitations as purely web-based agents. After all, why should it be any easier to communicate your goals to a PDA than it is to a web-based agent? Why would your preferences be any more developed for purchases supported by a PDA system than a web-based agent?

A key difference between purely web-based agents and the current "physical task support agents" (i.e. an agent that supports a user engaged in a task in a physical setting) is that web-based agents are completely responsible for conveying all information that will be considered by the user. On the other hand, "physical task support" agents in accordance with a preferred embodiment can augment the approaches of web-based agents by referring to aspects of a user's environment. For example, it is not terribly important to convey richly the feeling of a particular sweater if the sweater is in a store thirty feet away. It need only refer the shopper to the sweater. The shopper will gain a much better appreciation of the sweater by trying it on than through anything that can be conveyed by the system. When too many products match an imprecisely specified goal for a web-based agent, a more restrictive search must be made. However, many matches simply indicates there is a store that is likely to be of great interest to the shopper and therefore should be visited. Once inside, narrowing down the merchandise of interest in person will often be far easier than refining the goals on a web-based agent. Therefore physical task support agents can assist users to elaborate their preferences and identify specific goals by calling users' attention to aspects of their physical environment as a means of conveying information throughout the entire course of the task.

The Promise of Physical Shopping Agents

It is hardly surprising that physical shopping has been neglected by the agents community. After all, until very recently there simply was no reliable way to deliver customized information to individual shoppers in remote locations. However, the explosive growth of PDAs, and their increasingly sophisticated communications capabilities promise to make them effective channels of "just in time" information to users wherever they happen to be. The present invention provides an intuitive, novel agent that supports physical shopping by exploiting the promise of this developing channel that support all phases of the shopping task and solves the foregoing problems including:

Specification of Goals

Shoppers begin by indicating at least the general category of merchandise they are interested in. Shopping agents need to enable the specification of goals at various degrees of specificity. With the present invention these goals may be refined as the task progresses.

Exploration of Product Space

Before shoppers can make a selection, they need to become educated about what is available. Shopping agents can aid in this task by presenting various classes of offerings, reviews, demonstrations, etc. The present inventive Physical shopping agent can augment this by providing shoppers with a tour of the locally available offerings.

Refinement of Preferences

As shoppers learn what is available and examine the offerings their preferences evolve. Agents need to enable shoppers to refine their preferences over time. The present invention allows the user to refine their preferences.

Identification and Comparison of Candidate Products

As shoppers begin to understand what they want and what is available they typically compile a list of candidates that will be considered more carefully. The present inventive agents supports the construction and maintenance of such lists and facilitates the comparison of candidates within the list according to various criteria.

Negotiation of Offers

The present shopping agent is not restricted to providing the shopper with information. It is possible to negotiate prices and service options with retailers.

Product Selection, Purchase and Product Support

The present invention facilitates the transaction itself and can be used as a channel through which product service can be delivered.

Figure 27B:
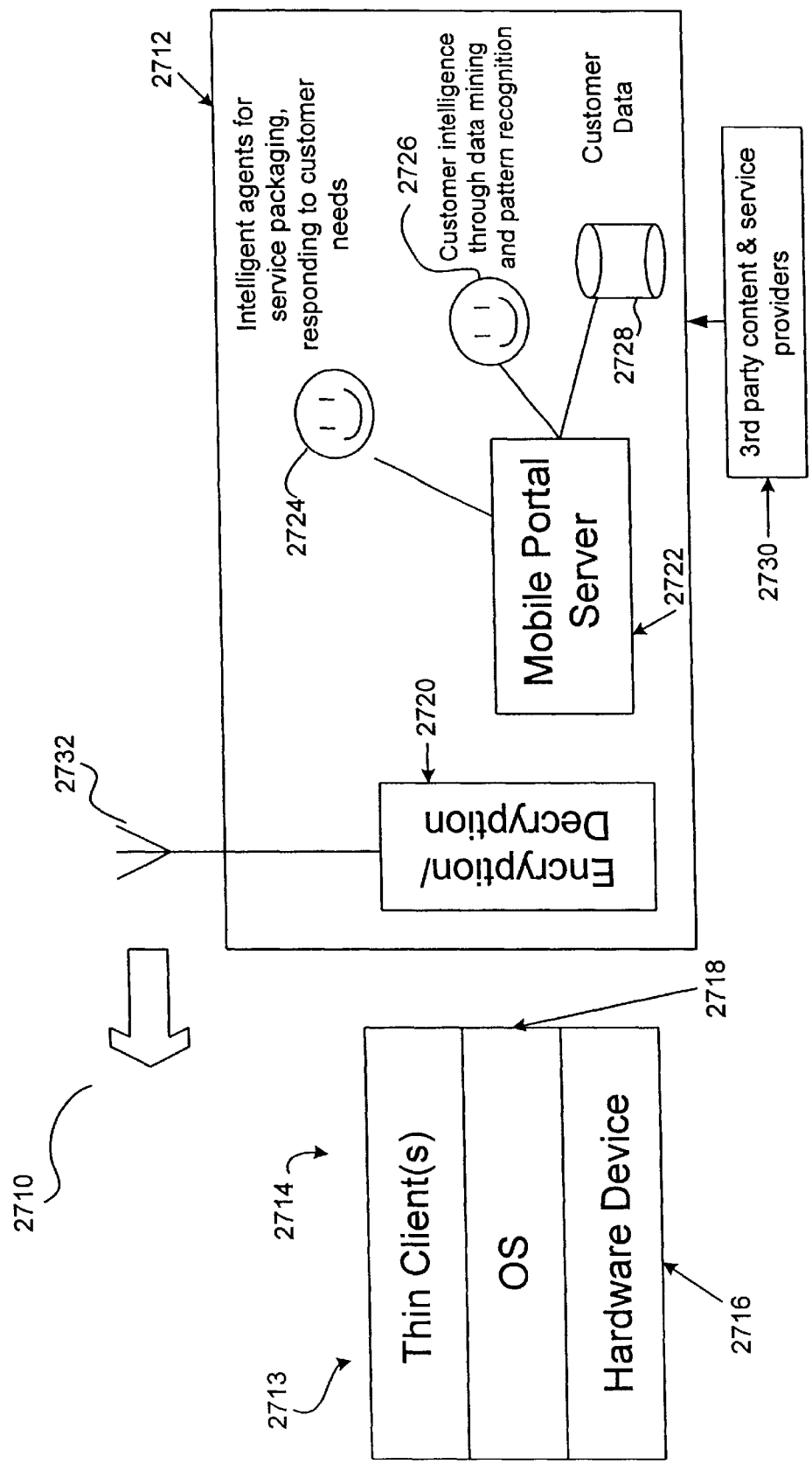
FIG. 27B is an illustration of a Mobile Portal platform in accordance with a preferred embodiment.

FIG. 27B is an illustration of the Mobile Portal platform 2710 including a Mobile Portal 2712 and an Electronic Valet 2713. The Electronic Valet 2713 includes a supporting hardware device 2716, such as a wireless PDA, and a Mobile Portal Thin Client standard 2714 executing on top of a Thin Client Operating System 2718. The Mobile Portal consist of an encryption and decryption element 2720, a Mobile Portal Server 2722, intelligent agents 2724, a Customer intelligence element 2726, and a Customer database 2728.

Thin Client is a generic term used to describe a group of rapidly emerging technologies that provide a reduction in total cost of ownership through a combination of reduced hardware costs, reduced maintenance and support costs, reduced LAN/WAN bandwidth requirements, reduced down time, improved performance and enhanced security. The term "Thin" in Thin Client refers to the (very small) size of the client operating system. In contrast, traditional PC operating systems (DOS, Windows 95, etc.) are considered "Fat" Clients due to their large size and resource requirements. Despite the fact that the Thin Client operating systems are thin, the capabilities of Thin Clients are robust. Thin Client solutions are deployed today in mission critical environments and they are providing reliable and responsive access to a myriad of applications. The Mobile Portal Thin Client 2714 is a Thin Client wherein the majority of the processing is done on the Mobile Portal Server 2722 and related third party content and service providers 2730. The user utilizes the Mobile Portal Thin Client application 2714 to select services and review information provided by the Mobile Portal Platform 2710. The Mobile Portal Thin Client application 2714 is made more device independent by the use of a Thin Client Operating System 2718. The Thin Client Operating System 2718 acts as a messenger between the Mobile Portal Thin Client application 2714 and the supporting hardware 2716. The Thin Client Operating System 2718 allows the Mobile Portal Thin Client 2714 to make function calls to the Thin Client Operating System 2718 for low level hardware operations, such as display calls and user input a queries. A separate Thin Client Operating system 2718 can be developed for each hardware device 2716 used as the supporting hardware for the Electronic Valet 2713. This allows the Mobile Portal Thin Client application 2714 to run on different supporting hardware 2716 without the need for significant low level design modification.

The Mobile Portal 2712 receives data from the Electronic Valet 2713 via a packet-switched wireless network 2732. Information received through the packet-switched wireless network is then decoded by the encryption and decryption element 2720 of the Mobile Portal 2712. Once the data has been decoded the Mobile Portal server 2722 utilizes intelligent agents 2724, customer intelligence 2726, and customer data 2728 to obtain the requested data from third party content and service providers 2730. The Mobile Portal Server 2722 utilizes intelligent software agents to respond to customer needs. The software agents 2722 utilize customer data 2728 to determine to personalize their task to the individual user's goals, habits and preferences. The customer data 2728 is in turn routinely updated by the customer and by the customer's actions. Each time a user uses the Mobile Portal 2712 a log is kept of the user's queries and other uses of the Mobile Portal Platform 2710. In this way, the software agents 2724 are able to utilize the user's past habits to personalize their task.

In addition to software agents 2724, the Mobile Portal Server 2722 utilizes customer intelligence 2726 to respond to user needs. The user may utilize data-mining and pattern recognition to find the information he desires. Again, the customer data 2728 is updated to reflect the users data-mining and pattern recognition uses. Third party content and service providers 2730 are utilized by the Mobile Portal 2712 to provide the services and information requested by the users. The third party content and service providers may be accessed through the Internet or through a Mobile Portal Extranet. The intelligent agent software 2712 search through the third party providers to determine the one most suitable for the user, taking into consideration the customer's profile contained in the customer data 2728. In this way, the user may be less specific in their queries than they would have to be without a user profile. For example, a user can request a jacket utilizing the Mobile Portal Platform 2710. The intelligent agents would then utilize the customer data 2728 to determine more specifically what the customer actually desired. In this case, the customer data 2728 may information that this particular user likes denim jackets as opposed to leather jackets. The intelligent agents 2724 would then search for denim jackets. Of course the user profile could be overridden by the user in order to obtain information that is contrary to what is stored in the user's profile. Some typical services provided include geographic location information, audio and visual editing, personal news & entertainment, personal shopping, personal health & safety, personal organizer, personal finance, and personal communication.

Geographic location services are typically based on information received from the integrated Global Positioning System. GPS data is combined with specific user request data to provide location specific information to the user. For example, the user may be located in San Francisco and wish obtain information on fine dining in the city. The user would request fine dining information utilizing the Electronic Valet 2713. Location data obtained from the integrated GPS receiver would be automatically combined with the user request for fine dining, and the combined message would then be transmitted to the Mobile Portal 2712. Based on the data received, the Mobile Portal would select the appropriate service and transmit the request, in this case fine dining in San Francisco. The Mobile Portal would then transmit the response received back to the Electronic Valet 2713. The user is then presented with the requested information, formatted and displayed on the display device of the Electronic Valet 2713.

Audio and visual editing services are typically based on the data received from the integrated camera and microphone. The user typically captures images utilizing the integrated digital camera. However, the user may also obtain digital images from other sources, such as scanners, e-mail, and web pages. In addition, the user typically captures sound files utilizing the integrated microphone. However, audio files may also be obtained from other sources, such as e-mail, web pages, and CDs. The image and/or audio data is combined with specific user request data to provide image and audio editing capabilities to the user. For example, the user may capture an image with the integrated digital camera, and then request to edit the image using a specific photo editor. The image captured by the integrated digital camera is then combined with the user's request for photo editing, and the combined message is then transmitted to the Mobile Portal 2712. Based on the data received, the Mobile Portal 2712 selects the appropriate service and transmits the request, in this case image editing. The Mobile Portal then transmits the response received back to the Electronic Valet 2713. The user is then presented with the requested information, formatted and displayed on the display device of the Electronic Valet 2713. In this case, the user would receive a user interface for image editing. The user would then use the image editing user interface to edit the image. Changes to the image are treated as request which the Mobile Portal 2712 passes on to the image editing application, running locally or on a separate server.

Bio-Medical Sensor Integration in Accordance with a Preferred Embodiment

One embodiment of the present invention is an Electronic Valet including integrated bio-sensors, such as pressure transducers, respiratory sensors, Volumetric Sensors, and Defibrillators.

Integrated Pressure Transducers to measure blood pressure can be of two types, invasive and noninvasive. Invasive integrated pressure transducers require the user to imbed part of the unit into the blood stream, while noninvasive integrated pressure transducers do not need access to the blood stream. Pressure transducers measure the blood pressure of the patient and report it to a receiving unit, in this case the Electronic Valet. The Electronic Valet is then able to analyze and rout the data received from the pressure transducer utilizing the Mobile Portal Thin Client and Mortal Portal Server.

Respiratory sensors, such as strain gages and volumetric sensors may also be integrated into the Electronic Valet. Strain gages worn around the chest region change impedance as the gage expands and contracts according to the expansion and contraction of the chest during breathing. Volumetric sensors sense the amount of air pressure passing through the sensor, such as when a patient breathes into the volumetric sensor. Both strain gages and volumetric sensors are able to wirelessly transmit their corresponding data to the Electronic Valet unit, thus giving the user greater freedom in their activities. As with data received from pressure transducers, data received from strain gages and volumetric sensors may be analyzed and routed utilizing the Mobile Portal Platform.

Defibrillators integrated into the Electronic Valet may be utilized to sense heart functions. Defibrillators attach to the patient utilizing a saline based gel and track heartbeats through R, T, and P waves. As with strain gages and volumetric sensors, defibrillators can wirelessly transmit data to the Electronic Valet, which then analyzes and routs the data utilizing the Mobile Portal Platform.

The above mentioned bio-sensors can be integrated individually or in combination with other sensors, such as environ-sensors, other bio-sensors, or a GPS receiver, depending on the need of the particular user. For example, an elderly user with a history of heart problems could have an Electronic Valet including an integrated Defibrillator and GPS receiver.

Utilizing the Mobile Portal Platform, the user could stay up-to-date on news and information about his condition, including various food and drugs that could be harmful.

In addition, the Electronic Valet is capable of sensing problems that may occur because of the heart condition, regardless of the location of the user. While walking in the park, the user may feel chest pains, the Electronic Valet would sense that the pains are being caused by difficulties arising because of the user's heart condition. This is accomplished utilizing the integrated defibrillator and the Electronic Valet's analysis capabilities. In this case, the data received from the integrated defibrillator will exceed predetermined safety thresholds, thus alerting the Electronic Valet that an emergency has occurred. Utilizing the Mobile Portal Platform, the Electronic Valet would then notify the appropriate emergency response unit, forward that heart data to the users physician, and notify the user's family.

In addition, the Electronic Valet forwards location coordinates, received from the integrated GPS receiver, to the emergency response unit allowing them to locate and rescue the user. After treatment at the hospital, the Mobile Portal Platform is able to coordinate the users after-care program, including tracking his diet and nutrition, as well as his exercise routine and medication.

Supporting Code in Accordance with a Preferred Embodiment

The following code is written and executed in the Microsoft Active Server Pages environment in accordance with a preferred embodiment. It consists primarily of Microsoft Jscript with some database calls embedded in the code to query and store information in the database.

Intention-Centric Interface

Create an Intention ASP Page ("intention_create.asp")

```
<%@ LANGUAGE = "JScript" %>
<%
Response.Buffer = true;
Response.Expires = 0;
%>
<html>
<head>
    <title>Create An Intention</title>
</head>
<body bgcolor="#FFE9D5" style="font-family: Arial" text="#000000">
<%
//Define some variables
upl = Server.CreateObject ("SoftArtisans.Fileup")
intention_name = upl.Form("intention_name")
intention_desc = upl.Form("intention_desc")
//intention_name = Reguest.Form("intention_name")
//intention_desc = Reguest.Form("intention_desc")
//intention_icon = Request.Form("intention_icon")
submitted = upl.Form("submitted")
items = new Enumerator(upl.Form)
%>
<%
//Establish connection to the database
objConnection = Server.CreateObject ("ADODB.Connection")
objConnection.Open ("Maelstrom")
%>
<%
//Check to see if the person hit the button and do the appropriate thing
if (submitted == "Add/Delete")
{
    flag = "false"
    //loop through all the inputs
    while(!items.atEnd())
    {
        i = items.item()
        //if items are checked then delete them
        if(upl.Form(i) == "on")
        {
            objConnection.Execute("delete from user_intention where intention_id =" +i);
            objConnection.Execute ("delete from intentions where
```

-continued

```
intention_id ="+ i);
                objconnection.Execute("delete from tools_to_intention where
intention_id ="+ i)
                flag = "true"
        }
        items.moveNext()
    }
    // if items were not deleted then insert whatever is in the text field in the
database
    if(flag == false")
    {
        intention_name_short = intention_name.replace(/ /gi,"")
        objConnection.Execute ("INSERT INTO intentions
(intention_name,intention_desc,intention_icon) values(" + intention_name + "', '" +
intention_desc + "', '" + intention_name_short + ".gif" +")")
        Response.write("the intention short name is " + intention_name_short);
        upl.SaveAs("E:development/asp_examples/"+ intention_name_short
+".gif")
    }
}
        // Query the database to show the most recent items.
        rsCustomersList = objConnection.Execute("SELECT * FROM intentions")
%>
<input type="Submit" name="return_to_mcp" value="Go to Main Control Panel"
onclick="location.href='default.asp'">
<form method="post" action="intention_create.asp" enctype="multipart/form-date" >
<TABLE border=0>
<tr><td colspan="2"><font face="Arial" size="+1"><b>Enter in a new
intention</b></font></td></tr>
<tr><td><font face="Arial">Name: </font></td><td><INPUT TYPE="text"
name="intention_name"></td></tr>
<tr><td><font face="Arial">Description:</font></td><td><TEXTAREA
name= "intention_desc"></TEXTAREA></td></tr>
<tr><td><font face="Arial">Icon Image:</font></td><td><INPUT TYPE="file"
NAME= "intention_icon" size=40></td></tr>
<tr><td colspan="2"><INPUT type="submit" name="submitted"
value="Add/Delete"></td></tr>
</TABLE>
<HR>
<font fece="Arial" size="+1"><b>Current Intentions</b></font>
<TABLE>
    <tr bgcolor=E69780 align="center">
    <td>
        <FONT color="white">Delete</FONT>
    </td>
    <TD>
        <FONT color="white">Intention</FONT>
    <TD>
    <TD>
        <FONT color="white">Description</FONT>
    </TD>
    <TD>
        <FONT color= "white">Image</FONT>
    </TD>
    </tr>
<%
// Loop over the intentions in the list
counter = 0;
while (!rsCustomersList.EOF)
{
%>
    <tr bgcolor="white" style="font-size: smaller">
        <td align=center>
            <INPUT type="checkbox"
name="<%=rsCustomersList("intention_id")%>">
        </TD>
        <td>
            <%= rsCustomersList("intention_name")%>
        </td>
        <td>
            <%= rsCustomersList ("intention_desc") %>
        </td>
        <td>
            <img src="../images/<%= rsCustomersList ("intention_icon")%>">
        </td>
    </tr>
<%
counter++
rsCustomersList.MoveNext ()}
```

-continued

```
%>
</TABLE>
<hr>
Avaliable Tools
</form>
</BODY>
</HTML>
```

Retrieve Intentions List ASP Page ("intentions_list.asp")

```
<!-- #include file="include/check_authentication.inc"-->
<HTML>
<HEAD>
    <TITLE>mySite!Intentions List</TITLE>
<SCRIPT LANCUAGE="JavaScript">
    function intentionsList () (
        this.internalArray = new Array();
        <%
        // establish connection to the database
        objConnection = Server.CreateObject ("ADODB.Connection");
        objConnection.Open ("Maelstrom");
        // create query
        intentionsQuery = objConnection.Execute("SELECT * FROM intentions
ORDER BY intention_name asc");
%>
        // write out the options
<%
        numOptions = 0
        while (!intentionsQuery.EDF) (
                intentionName = intentionsQuery("intention_name");
                intentionIcon = intentionsQuery("intention_icon");
%>
            this.internalArray[<%= numOptions%>] = new Array(2);
            this.internalArray[<%= nunOptions%>][0] = "<%= intentionName
%>";
            this.internalArray[<%= numOptions%>] [1] = "images/<%=
intentionIcon %>";
<%              numOptions++; intentionsQuery.moveNext();       %>
<%          }       %>
    }
    numIntentions = <%= nunOptions%>;
    intentionArray = new intentionsList () .internalArray;
    function selectIntention () {
        for (i=0;i<numIntentions;i++)    }
            if (IntentionsListSelect.options[i].selected) {
                intentionNameTextField.value = intentionArray[i] [0];
                //intentionPicture.src = intentionArray[i] [1];
                break;
            }
        }
    }
</SCRIPT>
</HEAD>
<BODY BGCOLOR="<%=Session("main_background")%>" style="font-family: Arial">
<CENTER>
<!--- <FORM.NAME="intention_list">--->
<TABLE FRAME="BOX" border=0 CELLPADDING="2" CELLSPACING="2">
<TR><TD COLSPAN="3" STYLE="font: 20pt arial" ALIGN="CENTER"><B>Add a mySite!
Intention</B></TD></TR>
<TR><TD COLSPAN="3"> </TD></TR>
<TR>
    <TD width="100"><font size="-1">Please Select An Intention You Would Like to
Add to Your List</font></TD>
    <TD colspan=2>
        <SELECT ID="IntentionsListSelect" NANE="IntentionsListSelect"
SIZE="10" style="font: 9pt Arial;" onClick="selectIntention))">
        <%
        intentionsQuery.moveFirst ();
        for(j=0;j<numOptions;j++) { %>
                <OPTION VALUE="<%= intentionsQuery("intention_id") %>" <% if
(j == 0) ( %>SELECTED <% ) %>>
                <%= intentionsQuery("intention_name") %>
                <% intentionsQuery.moveNext()
        }
        intentionsQuery.moveFirst ();
        %>
        </SELECT>
    </TD>
</TR>
<TR><TD COLSPAN="3">  </TD></TR>
```

-continued

```
<TR>
    <TD width="100"><font size="-1">Customize the Intention name</font></TD>
    <TD COLSPAN=2"><INPUT TYPE="text" NAME="intentionNameTextField"
ID="intentionNameTextField" SIZE="30" VALUE="<%= intentionsQuery("intention_name")
%>"></TD>
</TR>
<TR><TD COLSPAN="3"> </TD></TR>
<TR>
    <TD COLSPAN="3" ALIGN="CENTER">
        <INPUT TYPE="button" NAME="intentionOKButton" VALUE="    OK    "
SIZE="10" ID="intentionOKButton"
onClick="javeScript:top.opener.top.navframe.addAnIntention();">

<INPUT TYPE="button" NAME="intentionCancelButton" VALUE="Cancel"
SIZE="10" ID="intentionCancelButton" onClick="self.close();">
    </TD>
</TR>
</TABLE>
<!--- </FORM> --->
</CENTER>
<% objConnection.Close(); %>
</BODY>
</HTML>
```

Display User Intention List ASP Page (excerpted from "navigation.asp")

```
<DIV ID="intentionlist" style="position: absolute; width:210; height:95; left: 365pt;
top: -5; visibility: hidden; font-family: Arial; font-color: #000000; font: 8pt
Arial ; " >
<DIV style="position: absolute; top:7; left:7; height:78; width:210; z-index:2;
background: <%=Session("main_background")%>; border: solid 1pt #000000; padding: 3pt;
overflow: auto; alink: black; link: black;">
<body LINK="#000000" ALINK="#000000" vlink="black">
                <%
                // create query
                intentionsQuery = objConnection.Execute("SELECT
user_intention.* FROM user_intention, user_intention_to_persona WHERE
user_intention_to persona.user_persona_id = " + Session("currentUserPersona") +" AND
user_intention_to_persona.user_intention_id = user_intention.user_intention_id");
                numintentions = 0;
                Response.Write ("<SCRTPT>numintentions=" +
intentionsQuery.RecordCount + "</SCRIPT><TABLE cellpadding='0' width='100%'
cellspacing='0' >");
                while (!intentionsQuery.EOF)
                {
                %>
                <TR><TD><a     href="javascript:changeIntention('<%=
intentionsQuery("user_intention_id") %>', '<%=numintentions%>')
onmouseover="mouseOverTab()" onmouseout="mouseOutOfTab()"><font color="Black"
face="arial" size="-2"><%= intentionsQuery("intention_custom_name")
%></font></a></TD><TD><IMG align="right" SRC="images/delete.gif" alt="Delete this
intention" onClick="confirmDelete(<%= intentionsQuery("user_intention_id")
%>; "></TD></TR>
<%numintentions++; intentionsQuery.moveNext();
%>
                <%    }
Response.Write ("<SCRIPT>numintentions="+numintentions +"</SCRIPT>");
                %>
<tr><td colspan= "2"><hr></td></tr>
<TR><td colspan="2"><a href="javascript:changeIntention('add
...',<%=numintentions%>); "onmouseover="mouseOverTab()"
onmouseout="mouseOutOfTab()"><font color="Black" face="arial" size="-2">add
...</font></a></td></TR>
                </table>
</body>
</DIV>
<DIV style="position: absolute; top:0; left:-5; width: 230; height:105; z-index:1;
" onmouseout="intentionlist.style.visibility= 'hidden'"
onmouseout="intentionlist.style.visibility= 'hidden'"
onmouseover="intentionlist.style.visibility= 'hidden'"></DIV>
</DIV>
</DIV>
```

While various embodiments have been described above, it should be understood that they have been presented by way of example only, and not limitation. Thus, the breadth and scope of a preferred embodiment should not be limited by any of the above described exemplary embodiments, but should be defined only in accordance with the following claims and their equivalents.

What is claimed is:

1. A method for creating an information summary on a mobile computing environment, comprising the steps of:
    a) creating a query for an information summary based in part on a user input:
    b) querying a network of information having a content database utilizing a wireless communication device;
    c) receiving contents pertaining to the user from the network of information on the mobile computing environment; and
    d) parsing and summarizing the contents utilizing an application tool, wherein the application tool is a word-processor.

2. A method for creating an information summary on a mobile computing environment, comprising the steps of:
    a) creating a query for an information summary based in part on a user input:
    b) querying a network of information having a content database utilizing a wireless communication device;
    c) receiving contents pertaining to the user from the network of information on the mobile computing environment; and
    d) parsing and summarizing the contents utilizing an application tool, wherein the application tool provides healthcare services.

3. A computer program embodied on a computer-readable medium that creates an information summary, comprising:
    a) a code segment that creates a query for an information summary based in part on a user input;
    b) a code segment that queries a network of information having a content database utilizing a wireless communication device;
    c) a code segment that receives contents pertaining to the user from the network of information on the mobile computing environment; and
    d) a code segment that parses and summarizes the contents utilizing an application tool, wherein the application tool is a wordprocessor.

4. A computer program embodied on a computer-readable medium that creates an information summary, comprising:
    a) a code segment that creates a query for an information summary based in part on a user input;
    b) a code segment that queries a network of information having a content database utilizing a wireless communication device;
    c) a code segment that receives contents pertaining to the user from the network of information on the mobile computing environment; and
    d) a code segment that parses and summarizes the contents utilizing an application tool, wherein the application tool provides healthcare services.

5. An apparatus that creates an information summary, comprising:
    a) a processor;
    b) a memory that stores information under the control of a processor;
    c) logic that creates a query for an information summary based in part on a user input;
    d) logic that queries a network of information having a content database utilizing a wireless communication device;
    e) logic that receives contents pertaining to the user from the network of information on the mobile computing environment; and
    f) logic that parses and summarizes the contents utilizing an application tool, wherein the application tool is a wordprocessor.

6. An apparatus that creates an information summary, comprising:
    a) a processor;
    b) a memory that stores information under the control of a processor;
    c) logic that creates a query for an information summary based in part on a user input;
    d) logic that queries a network of information having a content database utilizing a wireless communication device;
    e) logic that receives contents pertaining to the user from the network of information on the mobile computing environment; and
    f) logic that parses and summarizes the contents utilizing an application tool, wherein the application tool provides healthcare services.

* * * * *